(12) United States Patent
Wang

(10) Patent No.: US 10,364,434 B2
(45) Date of Patent: Jul. 30, 2019

(54) COMPOSITIONS AND METHODS OF BIOSYNTHESIZING CAROTENOIDS AND THEIR DERIVATIVES

(71) Applicant: ARCH INNOTEK, LLC, St. Louis, MO (US)

(72) Inventor: Yechun Wang, St. Louis, MO (US)

(73) Assignee: ARCH INNOTEK, LLC, St. Louis, MO (US)

(*) Notice: Subject to any disclaimer, the term of this patent is extended or adjusted under 35 U.S.C. 154(b) by 0 days.

(21) Appl. No.: 15/560,951

(22) PCT Filed: Mar. 23, 2016

(86) PCT No.: PCT/US2016/023784
§ 371 (c)(1),
(2) Date: Sep. 22, 2017

(87) PCT Pub. No.: WO2016/154314
PCT Pub. Date: Sep. 29, 2016

(65) Prior Publication Data
US 2018/0080031 A1 Mar. 22, 2018

Related U.S. Application Data

(60) Provisional application No. 62/137,154, filed on Mar. 23, 2015.

(51) Int. Cl.
| | |
|---|---|
| *C12N 9/02* | (2006.01) |
| *C12N 9/10* | (2006.01) |
| *C12N 9/90* | (2006.01) |
| *C12P 5/02* | (2006.01) |
| *C12P 7/26* | (2006.01) |
| *C12N 15/52* | (2006.01) |
| *C12N 15/70* | (2006.01) |
| *C12N 15/81* | (2006.01) |
| *C12P 23/00* | (2006.01) |

(52) U.S. Cl.
CPC ............. *C12N 15/52* (2013.01); *C12N 9/001* (2013.01); *C12N 9/0069* (2013.01); *C12N 9/1085* (2013.01); *C12N 9/90* (2013.01); *C12N 15/70* (2013.01); *C12N 15/81* (2013.01); *C12N 15/815* (2013.01); *C12P 5/026* (2013.01); *C12P 7/26* (2013.01); *C12P 23/00* (2013.01); *C12Y 101/01034* (2013.01); *C12Y 103/99* (2013.01); *C12Y 113/11051* (2013.01); *C12Y 205/01* (2013.01); *C12Y 205/01001* (2013.01); *C12Y 205/0101* (2013.01); *C12Y 505/01018* (2013.01); *C12Y 505/01019* (2013.01)

(58) Field of Classification Search
CPC combination set(s) only.
See application file for complete search history.

(56) References Cited

U.S. PATENT DOCUMENTS

| | | | |
|---|---|---|---|
| 7,115,786 B2 | 10/2006 | Khackik et al. | |
| 2004/0191365 A1 | 9/2004 | Leuenberger et al. | |
| 2008/0124755 A1 | 5/2008 | Louie et al. | |
| 2009/0093015 A1 | 4/2009 | Louie et al. | |

FOREIGN PATENT DOCUMENTS

WO 2017036495 A1 3/2017

OTHER PUBLICATIONS

Barth G & Gaillardin C, Physiology and genetics of the dimorphic fungus Yarrowia lipolytica, 1997, FEMS Microbiol Rev., pp. 219-237, vol. 19, No. 4.
Kim et al, Cloning of the ribosomal protein L41 gene of Phaffia rhodozyma and its use a drug resistance marker for transformation, 1998, Appl Environ Microbiol, pp. 1947-1949, vol. 64, No. 5.
Madzak, C., Gaillardin, C. and Beckerich, J.M., Heterologous protein expression and secretion in the non-conventional yeast Yarrowia lipolytica: a review, J. Biotechnol., 2004, pp. 63-81, vol. 109.
Martinez et al, Genetic transformation of astaxanthin mutants of Phaffia rhodozyma, 1998, Antonie Van Leeuwenhoek, pp. 147-53, vol. 73, No. 2.
Perrut, M., Supercritical Fluid Applications: Industrial Developments and Economic Issues, 2000, Ind. Eng Chem Res, 2000, pp. 4531-4535, vol. 39, No. 12.
Verdoes et al, Metabolic engineering of the carotenoid biosynthetic pathway in the yeast Xanthophyllomyces dendrorhous (Phaffia rhodozyma). 2003, Appl Environ Microbiol, 2003, pp. 3728-3738, vol. 69, No. 7.
Visser et al, Metabolic engineering of the astaxanthin-biosynthetic pathway of Xanthophyllomyces dendrorhous, 2003, FEMS Yeast Res, pp. 221-231, vol. 4, No. 3.
Wery et al, High copy number integration into the ribosomal DNA of the yeast Phaffia rhodozyma, 1997, Gene, pp. 89-97, vol. 184, No. 1.
Altschul, S.F. et al, Basic Local Alignment Search Tool, J. Mol. Biol., 1990, pp. 403-410, vol. 215.
Altschul, S.F. et al, Gapped Blast and PSI-Blast: a new generation of protein database search programs, 1997, Nucleic Acids Research, pp. 3389-3402, vol. 25, No. 17.
Cunningham, F.X. et al, Functional Analysis of the β and ε Lycopene Cyclase Enzymes of *Arabidopsis* Reveals a Mechanism for Control of Cyclic Carotenoid Formation, 1996, The Plant Cell, pp. 1613-1626, vol. 8.
Pronk, J.T., Steensma, H.Y. and Van Dijken, J.P., Pyruvate Metabolism in *Saccharomyces cerevisiae*, 1996, Yeast, pp. 1607-1633, vol. 12.

(Continued)

*Primary Examiner* — Kagnew H Gebreyesus
(74) *Attorney, Agent, or Firm* — Polsinelli PC; Tara A. Nealey

(57) ABSTRACT

The present invention relates to compositions and methods of producing carotenoids and carotenoid derivatives.

7 Claims, 20 Drawing Sheets
(9 of 20 Drawing Sheet(s) Filed in Color)
Specification includes a Sequence Listing.

(56) References Cited

OTHER PUBLICATIONS

Reeck, G.R. et al, "Homology" in Proteins and Nucleic Acids: A Terminology Muddle and a Way out of It, 1987, Cell, pp 667, vol. 50.

Sherman, D. et al, Genolevures: comparative genomics and molecular evolution of hemiascomycetous yeasts, 2004, Nucleic Acids Research, pp. D315-D318, vol. 32.

Tai, M. and Stephanopoulos, G., Engineeringthepushandpulloflipidbiosynthesisinoleaginousyeast Yarrowia lipolytica for biofuelproduction, 2013, Metabolic Engineering, pp. 1-9, vol. 15.

SEQUENCE LISTING

<160> NUMBER OF SEQ ID NOS: 92

<210> SEQ ID NO 1
<211> LENGTH: 83
<212> TYPE: DNA
<213> ORGANISM: Artificial Sequence
<220> FEATURE:
<223> OTHER INFORMATION: SYNTHESIZED

<400> SEQUENCE: 1
tccatatgaa ttatgcatgc ataacttcgt ataatgtatg ctatacgaag ttataccaaa    60
atgccctcct acgaagctcg agc                                            83

<210> SEQ ID NO 2
<211> LENGTH: 80
<212> TYPE: DNA
<213> ORGANISM: Artificial Sequence
<220> FEATURE:
<223> OTHER INFORMATION: SYNTHESIZED

<400> SEQUENCE: 2
ccacatgtgg gaattcataa cttcgtatag catacattat acgaagttat cgagaaacac    60
aacaacatgc cccattggac                                                80

<210> SEQ ID NO 3
<211> LENGTH: 43
<212> TYPE: DNA
<213> ORGANISM: Artificial Sequence
<220> FEATURE:
<223> OTHER INFORMATION: SYNTHESIZED

<400> SEQUENCE: 3
ggaattccgg gtttaaacag agaccgggtt ggcggcgtat ttg                      43

<210> SEQ ID NO 4
<211> LENGTH: 60
<212> TYPE: DNA
<213> ORGANISM: Artificial Sequence
<220> FEATURE:
<223> OTHER INFORMATION: SYNTHESIZED

<400> SEQUENCE: 4
tagggtacct ctagacgtcc acccgggaag gatcctttga atgattctta tactcagaag    60

<210> SEQ ID NO 5
<211> LENGTH: 60
<212> TYPE: DNA
<213> ORGANISM: Artificial Sequence
<220> FEATURE:
<223> OTHER INFORMATION: SYNTHESIZED

<400> SEQUENCE: 5
cttctgagta taagaatcat tcaaaggatc cttcccgggt ggacgtctag aggtaccta     60

<210> SEQ ID NO 6
<211> LENGTH: 47
<212> TYPE: DNA
<213> ORGANISM: Artificial Sequence
<220> FEATURE:
<223> OTHER INFORMATION: SYNTHESIZED

<400> SEQUENCE: 6
ccacatgtgg acgtcgacgc cacctacaag ccagattttc tatttac                  47

<210> SEQ ID NO 7
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 7
atgcatgccg cctgagtcat catttattta ccag                          34

<210> SEQ ID NO 8
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 8
ttgtttaaac gaatatacag taacaagcta ccacc                         35

<210> SEQ ID NO 9
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 9
tccatatgcc agtctacact gattaatttt cggg                          34

<210> SEQ ID NO 10
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 10
ttgcatgcat aagctaaaag taactcgcag cgca                          34

<210> SEQ ID NO 11
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 11
ggtgatcaat ggccaattta ctgaccgtac acc                           33

<210> SEQ ID NO 12
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 12
ttcccgggtc aatcgccatc ttccagcagg cgcac                         35

<210> SEQ ID NO 13
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 13
tccatatggc ggccgcgggt ccggctgcca gttgcccagc cgccag    46

<210> SEQ ID NO 14
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 14
atgcatgctg gtggtagtag caaatattca aatg    34

<210> SEQ ID NO 15
<211> LENGTH: 44
<212> TYPE: DNA
<213> ORGANISM: Artificial Sequence
<220> FEATURE:
<223> OTHER INFORMATION: SYNTHESIZED

<400> SEQUENCE: 15
gcgtcgacgt tggcgcgcct gcttcggtat gataggaaga gccg    44

<210> SEQ ID NO 16
<211> LENGTH: 42
<212> TYPE: DNA
<213> ORGANISM: Artificial Sequence
<220> FEATURE:
<223> OTHER INFORMATION: SYNTHESIZED

<400> SEQUENCE: 16
ccacatgtgc ggccgcggca gacactgcgt cgctccgtcc ac    42

<210> SEQ ID NO 17
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 17
cgggatccat gtctaagaag catattgtga tt    32

<210> SEQ ID NO 18
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 18
ttcctaggct tagatgacgt tggagttgtg cac    33

<210> SEQ ID NO 19
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 19
cgggatccat gctgctgact tacatggagg ttc    33

<210> SEQ ID NO 20
<211> LENGTH: 33

<212> TYPE: DNA
<213> ORGANISM: Artificial Sequence
<220> FEATURE:
<223> OTHER INFORMATION: SYNTHESIZED

<400> SEQUENCE: 20
ttcctaggtt agatggtgtt caggtttcgc atc                           33

<210> SEQ ID NO 21
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 21
cgggatccat ggattataac agcgcggatt tc                            32

<210> SEQ ID NO 22
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 22
taaccgcagg attataacag cgcggatttc                               30

<210> SEQ ID NO 23
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 23
ttcctaggtc actgcgcatc ctcaaagtac tttc                          34

<210> SEQ ID NO 24
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 24
gcgtcgacag agaccgggtt ggcggcgtat ttg                           33

<210> SEQ ID NO 25
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 25
ttggcgcgcc agagaccggg ttggcggcgt atttg                         35

<210> SEQ ID NO 26
<211> LENGTH: 39
<212> TYPE: DNA
<213> ORGANISM: Artificial Sequence
<220> FEATURE:
<223> OTHER INFORMATION: SYNTHESIZED

<400> SEQUENCE: 26
ttggcgcgcc gccacctaca agccagattt tctatttac                    39

<210> SEQ ID NO 27
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 27
cgggatccat ggagtgcttt ggagctcgaa ac                           32

<210> SEQ ID NO 28
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 28
ggggtaccct atatagtgag atatgctttt acc                          33

<210> SEQ ID NO 29
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 29
cgggatccat gggagttacc gagcacgaga agtc                         34

<210> SEQ ID NO 30
<211> LENGTH: 27
<212> TYPE: DNA
<213> ORGANISM: Artificial Sequence
<220> FEATURE:
<223> OTHER INFORMATION: SYNTHESIZED

<400> SEQUENCE: 30
ggggtacctt acagcttagc ctgctcc                                 27

<210> SEQ ID NO 31
<211> LENGTH: 27
<212> TYPE: DNA
<213> ORGANISM: Artificial Sequence
<220> FEATURE:
<223> OTHER INFORMATION: SYNTHESIZED

<400> SEQUENCE: 31
cgggatccat gtccaaggcg aaattcg                                 27

<210> SEQ ID NO 32
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 32
taaccgcagt ccaaggcgaa attcgaaagc gtgt                         34

<210> SEQ ID NO 33
<211> LENGTH: 58
<212> TYPE: DNA
<213> ORGANISM: Artificial Sequence

```
<220> FEATURE:
<223> OTHER INFORMATION: SYNTHESIZED

<400> SEQUENCE: 33
aaatccgcgc tgttataatc catagaacca ccacccttct gtcgcttgta aatcttgg        58

<210> SEQ ID NO 34
<211> LENGTH: 58
<212> TYPE: DNA
<213> ORGANISM: Artificial Sequence
<220> FEATURE:
<223> OTHER INFORMATION: SYNTHESIZED

<400> SEQUENCE: 34
ccaagattta caagcgacag aagggtggtg gttctatgga ttataacagc gcggattt        58

<210> SEQ ID NO 35
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 35
gtccctctgg aggagtacat gttctt                                          26

<210> SEQ ID NO 36
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 36
aagaacatgt actcctccag agggac                                          26

<210> SEQ ID NO 37
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 37
gtcccccacc tgcccgtgga ggagtt                                          26

<210> SEQ ID NO 38
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 38
aactcctcca cgggcaggtg ggggac                                          26

<210> SEQ ID NO 39
<211> LENGTH: 27
<212> TYPE: DNA
<213> ORGANISM: Artificial Sequence
<220> FEATURE:
<223> OTHER INFORMATION: SYNTHESIZED

<400> SEQUENCE: 39
taaccgcagt ctaagaagca tattgtg                                         27
```

<210> SEQ ID NO 40
<211> LENGTH: 31
<212> TYPE: DNA
<213> ORGANISM: Artificial Sequence
<220> FEATURE:
<223> OTHER INFORMATION: SYNTHESIZED

<400> SEQUENCE: 40
taaccgcagc tgctgactta catggaggtt c                                    31

<210> SEQ ID NO 41
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 41
ggaattcatg agcaagaaac acattgtaat aa                                   32

<210> SEQ ID NO 42
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 42
gaagatcttt atatgacgtt ggagttatgc acc                                  33

<210> SEQ ID NO 43
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 43
cgggatccat gctattgaca tatatggagg tcc                                  33

<210> SEQ ID NO 44
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 44
ccctcgagtt atatagtgtt caaatttctc att                                  33

<210> SEQ ID NO 45
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 45
ggaattcatg gaccaattgg tgaaaactga agtc                                 34

<210> SEQ ID NO 46
<211> LENGTH: 32
<212> TYPE: DNA
<213> ORGANISM: Artificial Sequence
<220> FEATURE:
<223> OTHER INFORMATION: SYNTHESIZED

```
<400> SEQUENCE: 46
gactagttta ggatttaatg caggtgacgg ac                                32

<210> SEQ ID NO 47
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 47
cgggatccat ggcttcagaa aagaaatta gga                                33

<210> SEQ ID NO 48
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 48
ccctcgagtc acaattcgga taagtggtct att                               33

<210> SEQ ID NO 49
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 49
cgggatccat ggagtgcttc ggcgctagaa ata                               33

<210> SEQ ID NO 50
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 50
ccctcgagct aaatagtaag atatgccttg acc                               33

<210> SEQ ID NO 51
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 51
cgggatccat ggagtgtttt ggcgctcgta ata                               33

<210> SEQ ID NO 52
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 52
aactgcagct agatggtcaa atatgcctta acc                               33

<210> SEQ ID NO 53
```

<210> SEQ ID NO 53
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 53
ggaattcatg ggcgttacag aacatgagaa aag          33

<210> SEQ ID NO 54
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 54
gaagatctct acaatttagc ttgctcctgc agt          33

<210> SEQ ID NO 55
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 55
ggaattcatg ggagtcacgg agcacgagaa gt           32

<210> SEQ ID NO 56
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 56
ggaattcatg ggagtcacgg agcacgagaa gt           32

<210> SEQ ID NO 57
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 57
cgggatccta cgtactgcaa aaagtgctgg tc           32

<210> SEQ ID NO 58
<211> LENGTH: 1739
<212> TYPE: DNA
<213> ORGANISM: Mucor circinelloides

<400> SEQUENCE: 58
atgtccaaga aacacattgt cattatcggt gctggcgtgg gtggcacggc tacagctgct      60
cgtttggccc gcgaaggctt caaggtcact gtggtggaga aaacgacttt tggtggcggc     120
cgctgctcct tgatccatca ccagggccat cgctttgatc agggcccgtc gctctacctg     180
atgcccaagt actttgagga cgcctttgcc gatctggacg agcgcattca agaccacctg     240
gagctgctgc gatgcgacaa caactacaag gtgcactttg acgacggtga gtcgatccag     300
ctgtcgtctg acttgacacg catgaaggct gaattggacc gcgtggaggg cccccttggt     360
tttggccgat tcctggattt catgaaagag acacacatcc actacgaaag cggcaccctg     420

```
attgcgctca agaagaattt cgaatccatc tgggacctga ttcgcatcaa gtacgctcca      480
gagatctttc gcttgcacct gtttggcaag atctacgacc gcgcttccaa gtacttcaag      540
accaagaaga tgcgcatggc attcacgttt cagaccatgt atatgggcat gtcgccctac      600
gatgcgcctg ctgtctacag cctgttgcag tacaccgagt tcgctgaagg catctggtat      660
ccccgtggcg gcttcaacat ggtggttcag aagctagagg cgattgcaaa gcaaaagtac      720
gatgccgagt ttatctacaa tgcgcctgtt gccaagatta acaccgatga tgccaccaaa      780
caagtgacag gtgtaacctt ggaaaatggc cacatcatcg atgccgatgc ggttgtgtgt      840
aacgcagatc tggtctatgc ttatcacaat ctgttgcctc cctgccgatg gacgcaaaac      900
acactggctt ccaagaaatt gacgtcttct tccatttcct tctactggtc catgtccacc      960
aaggtgcctc aattggacgt gcacaacatc ttttttggccg aggcttatca ggagagcttt     1020
gacgaaatct tcaaggactt tggcctgcct tctgaagcct ccttctacgt caatgtgccc     1080
tctcgcatcg atccttctgc tgctcccgac ggcaaggact tgtcattgt cttggtgcct      1140 attggtcata tgaagagcaa gacgggcgat gcttccaccg agaactaccc ggccatggtg     1200
gacaaggcac gcaagatggt gctggctgtg attgagcgtc gtctgggcat gtcgaatttc     1260
gccgacttga ttgagcatga gcaagtcaat gatcccgctg tatggcagag caagttcaat     1320
ctgtggagag gctcaattct gggtttgtct catgatgtgc ttcaggtgct gtggttccgt     1380
cccagcacaa aggattctac cggtcgttat gataacctat tctttgtggg tgcaagcacg     1440
catcccggaa ctggtgttcc cattgtcctt gcaggaagca agctcacctc tgaccaagtt     1500
gtcaagagct ttggaaagac gcccaagcca agaaagatcg agatggagaa cacgcaagca     1560
cctttggagg agcctgatgc tgaatcgaca ttccctgtgt ggttctggtt gcgcgctgcc     1620
ttttgggtca tgtttatgtt cttttacttc ttccctcaat ccaatggcca aacgcccgca     1680 tctttatca ataatttgtt acctgaagta ttccgcgttc ataactctaa tgtcattta      1739
```

<210> SEQ ID NO 59
<211> LENGTH: 1740
<212> TYPE: DNA
<213> ORGANISM: Artificial Sequence
<220> FEATURE:
<223> OTHER INFORMATION: SYNTHESIZED

<400> SEQUENCE: 59

```
atgtctaaga agcatattgt gattattgga gccggagttg gaggcaccgc taccgccgcc       60
cgactggccc gagagggatt caaggttacc gtcgtggaga agaacgactt tggcggtgga      120
cgatgctctc tgatccacca tcagggacac cgattcgacc agggcccctc cctgtacctc      180
atgcctaagt actttgagga tgccttcgct gacctggatg agcgaatcca ggaccacctc      240
gagctgctcc gatgtgataa caactacaag gttcatttcg acgatggcga gtctattcag      300
ctgtcctctg acctcacccg aatgaaggcc gagctggatc gagtcgaggg tcccctggga      360
ttcggccgat ttctcgactt catgaaggag acccacatcc attacgagtc tggaactctg      420
attgctctca agaagaactt cgagtcgatt tgggacctga tccgaattaa gtacgccccc      480
gagattttcc gactgcacct cttcggcaaa atctacgatc gagcctccaa gtacttcaag      540
accaagaaga tgcgaatggc tttcaccttt cagactatgt acatgggcat gtccccctac      600 gacgccctg ctgtgtactc tctgctccag tacaccgagt tgccgagggg tatctggtat      660
ccccgaggcg gtttcaacat ggttgtccag aagctggagg ccattgccaa gcagaagtac      720
```

```
gacgctgagt tcatctacaa cgcccctgtg gctaagatta acaccgacga tgccactaag    780
caggtgaccg gtgttactct ggagaacgga cacatcattg acgccgatgc tgtggtttgc    840
aacgccgacc tcgtctacgc ttaccataac ctgctccccc cttgtcgatg acccagaac    900 actctggcct cgaagaagct cacttcgtcc tctatctcct tctactggtc gatgtccacc    960
aaggttcccc agctggacgt ccacaacatc tttctcgccg aggcttacca ggagtctttc   1020
gacgagattt ttaaggattt cggactgccc tctgaggctt cgttctacgt taacgtccct   1080
tctcgaattg accctcggc cgctcctgac ggcaaggatt ccgtgatcgt tctcgtcccc   1140
attggccata tgaagtcgaa gaccggtgac gcctccactg agaactaccc tgccatggtg   1200
gataaggctc gaaagatggt cctggccgtg atcgagcgac gactcggaat gtctaacttt   1260
gctgacctga ttgagcacga gcaggtgaac gatcccgccg tttggcagtc caagttcaac   1320
ctctggcgag gctccatcct gggtctctct catgacgttc tgcaggtcct ctggttccga   1380
ccttccacca aggactctac tggacgatac gataacctgt tctttgtcgg cgcttctacc   1440
caccccggta ctggagtgcc tatcgttctg gccggttcga agctcacctc cgaccaggtc   1500
gtgaagtcct tcggaaagac tcccaagcct cgaaagattg agatggagaa cacccaggct   1560
cctctggagg agcctgacgc tgagtctacc tttcccgtct ggttctggct ccgagccgct   1620
ttttgggtca tgttcatgtt cttttacttc tttccccagt ctaacggaca gacccctgcc   1680
tcgtttatca caacctgct ccccgaggtc ttccgagtgc acaactccaa cgtcatctaa   1740
```

<210> SEQ ID NO 60
<211> LENGTH: 1740
<212> TYPE: DNA
<213> ORGANISM: Artificial Sequence
<220> FEATURE:
<223> OTHER INFORMATION: SYNTHESIZED

<400> SEQUENCE: 60

```
atgagcaaga aacacattgt aataattggg gcaggggttg gggggaccgc taccgccgct     60
aggttggcta gagagggttt caaagttacg gtggtcgaga aaaatgattt tggcggtggt    120
agatgttccc tgatccatca ccaagggcat aggttcgacc agggtccgag cctttaccta    180
atgcccaaat attttgaaga tgccttcgcc gacctagatg aacgtattca ggatcatcta    240
gaattattac gttgtgataa caactataaa gttcatttcg acgacggcga atcaatacag    300
ctttcatccg atcttactag aatgaaggct gaacttgata gagtagaagg tcctctgggt    360
tttggaaggt tcctagattt catgaaggaa acgcatatac actacgagag tggtacttta    420
atcgcattga aaagaacctt tgaatctatc tgggacttaa taagaattaa gtacgccccc    480
gaaatattcc gtttgcatct gttcggaaag atttatgatc gtgcatctaa atattttaag    540
actaaaaaga tgaggatggc gtttacattc cagacgatgt acatgggtat gtcaccatat    600
gacgcaccag cagtctatag tctattgcaa tacaccgagt tcgccgaagg gatctggtac    660
ccacgtggcg ggttcaatat ggtagttcaa aaattggagg ccattgcgaa acaaaaatat    720
gatgcagagt tcatctataa tgcgccagtc gcaaagatta atactgacga cgcaacaaag    780
caagttaccg gggtgaccct tgaaaacggc catataatag acgcagacgc ggtagtgtgc    840
aatgccgatc tagtgtatgc ttaccataat ttgctgccgc cttgtagatg gactcaaaat    900
acattagctt ccaaaaagct aactagctca agcatttcat tctactggag tatgagcaca    960
aaggttcccc aactagatgt gcacaacatt ttccttgccg aggcttacca agagtctttt   1020
gatgaaatct ttaaagactt cgggctaccc tccgaggctt ccttctatgt aaatgtgcca   1080
```

-continued

```
agcaggattg acccttcagc cgcccccgac ggtaaggaca gtgtcatagt ccttgtaccc    1140
atcgggcata tgaagtctaa acgggggac gcatcaactg aaaattaccc cgcgatggtt     1200
gataaggcaa ggaagatggt tctagctgtt attgagagga gattaggtat gtctaatttt    1260
gcggacctga tcgagcacga gcaggttaac gaccctgctg tatggcagtc caagtttaac    1320
ttgtggcgtg ggagtatact ggggcttttcc cacgacgtat tacaagtact gtggtttcgt   1380
ccgtcaacaa aagatagtac ggggcgttat gacaatcttt tttttgttgg ggcttctact    1440
cacccgggta ccggtgtccc catcgtcctg gcggggagta aactgacgtc cgatcaggtt    1500
gtaaaatcat tgggaaaaac gccaaaacca aggaagatag agatggaaaa tacccaagcc    1560
ccgttagaag agcctgacgc cgaatccaca ttccccgtct ggttctggct acgtgcggcg    1620
ttctgggtaa tgtttatgtt tttctatttc ttcccccaat ctaatggaca gacaccggct    1680
agcttcatca acaacctgct tcccgaagtt ttcagggtgc ataactccaa cgtcatataa    1740
```

<210> SEQ ID NO 61
<211> LENGTH: 579
<212> TYPE: PRT
<213> ORGANISM: Yarrowia lipolytica

<400> SEQUENCE: 61

```
Met Ser Lys Lys His Ile Val Ile Ile Gly Ala Gly Val Gly Thr
1               5                   10                  15

Ala Thr Ala Ala Arg Leu Ala Arg Glu Gly Phe Lys Val Thr Val Val
            20                  25                  30

Glu Lys Asn Asp Phe Gly Gly Gly Arg Cys Ser Leu Ile His His Gln
        35                  40                  45

Gly His Arg Phe Asp Gln Gly Pro Ser Leu Tyr Leu Met Pro Lys Tyr
    50                  55                  60

Phe Glu Asp Ala Phe Ala Asp Leu Asp Glu Arg Ile Gln Asp His Leu
65                  70                  75                  80

Glu Leu Leu Arg Cys Asp Asn Asn Tyr Lys Val His Phe Asp Asp Gly
                85                  90                  95

Glu Ser Ile Gln Leu Ser Ser Asp Leu Thr Arg Met Lys Ala Glu Leu
            100                 105                 110

Asp Arg Val Glu Gly Pro Leu Gly Phe Gly Arg Phe Leu Asp Phe Met
        115                 120                 125

Lys Glu Thr His Ile His Tyr Glu Ser Gly Thr Leu Ile Ala Leu Lys
    130                 135                 140

Lys Asn Phe Glu Ser Ile Trp Asp Leu Ile Arg Ile Lys Tyr Ala Pro
145                 150                 155                 160

Glu Ile Phe Arg Leu His Leu Phe Gly Lys Ile Tyr Asp Arg Ala Ser
                165                 170                 175

Lys Tyr Phe Lys Thr Lys Lys Met Arg Met Ala Phe Thr Phe Gln Thr
            180                 185                 190

Met Tyr Met Gly Met Ser Pro Tyr Asp Ala Pro Ala Val Tyr Ser Leu
        195                 200                 205

Leu Gln Tyr Thr Glu Phe Ala Glu Gly Ile Trp Tyr Pro Arg Gly Gly
    210                 215                 220

Phe Asn Met Val Val Gln Lys Leu Glu Ala Ile Ala Lys Gln Lys Tyr
225                 230                 235                 240

Asp Ala Glu Phe Ile Tyr Asn Ala Pro Val Ala Lys Ile Asn Thr Asp
                245                 250                 255
```

Asp Ala Thr Lys Gln Val Thr Gly Val Thr Leu Glu Asn Gly His Ile
            260                 265                 270

Ile Asp Ala Asp Ala Val Val Cys Asn Ala Asp Leu Val Tyr Ala Tyr
        275                 280                 285

His Asn Leu Leu Pro Pro Cys Arg Trp Thr Gln Asn Thr Leu Ala Ser
    290                 295                 300

Lys Lys Leu Thr Ser Ser Ile Ser Phe Tyr Trp Ser Met Ser Thr
305                 310                 315                 320

Lys Val Pro Gln Leu Asp Val His Asn Ile Phe Leu Ala Glu Ala Tyr
                325                 330                 335

Gln Glu Ser Phe Asp Glu Ile Phe Lys Asp Phe Gly Leu Pro Ser Glu
            340                 345                 350

Ala Ser Phe Tyr Val Asn Val Pro Ser Arg Ile Asp Pro Ser Ala Ala
        355                 360                 365

Pro Asp Gly Lys Asp Ser Val Ile Val Leu Val Pro Ile Gly His Met
    370                 375                 380

Lys Ser Lys Thr Gly Asp Ala Ser Thr Glu Asn Tyr Pro Ala Met Val
385                 390                 395                 400

Asp Lys Ala Arg Lys Met Val Leu Ala Val Ile Glu Arg Arg Leu Gly
                405                 410                 415

Met Ser Asn Phe Ala Asp Leu Ile Glu His Glu Gln Val Asn Asp Pro
            420                 425                 430

Ala Val Trp Gln Ser Lys Phe Asn Leu Trp Arg Gly Ser Ile Leu Gly
        435                 440                 445

Leu Ser His Asp Val Leu Gln Val Leu Trp Phe Arg Pro Ser Thr Lys
    450                 455                 460

Asp Ser Thr Gly Arg Tyr Asp Asn Leu Phe Phe Val Gly Ala Ser Thr
465                 470                 475                 480

His Pro Gly Thr Gly Val Pro Ile Val Leu Ala Gly Ser Lys Leu Thr
                485                 490                 495

Ser Asp Gln Val Val Lys Ser Phe Gly Lys Thr Pro Lys Pro Arg Lys
            500                 505                 510

Ile Glu Met Glu Asn Thr Gln Ala Pro Leu Glu Glu Pro Asp Ala Glu
        515                 520                 525

Ser Thr Phe Pro Val Trp Phe Trp Leu Arg Ala Ala Phe Trp Val Met
    530                 535                 540

Phe Met Phe Phe Tyr Phe Pro Gln Ser Asn Gly Gln Thr Pro Ala
545                 550                 555                 560

Ser Phe Ile Asn Asn Leu Leu Pro Glu Val Phe Arg Val His Asn Ser
                565                 570                 575

Asn Val Ile

<210> SEQ ID NO 62
<211> LENGTH: 1845
<212> TYPE: DNA
<213> ORGANISM: Mucor circinelloides

<400> SEQUENCE: 62
atgctgctca cctacatgga agtccacctc tactacacgc tgcctgtgct gggcgtcctg      60
tcctggctgt cgcggccgta ctacacagcc accgatgcgc tcaaattcaa atttctgaca     120
ctggttgcct tcgcgaccgc ctccgcctgg gacaactaca ttgtctacca caaggcgtgg     180
tcctactgcc ccacctgcgt caccgctgtc attggctacg tgcccttgga ggagtacatg     240
ttcttcatca tcatgactct gttgaccgtg gcattcacca atctggtgat gcgctggcac     300

```
ctgcacagct tctttatcag gcctgaaacg cccgtcatgc agtccgtcct ggtccgtctt    360
gtccccataa cagccttatt aatcactgca tacaaggctt ggcatttggc ggtccctgga    420
aagccactgt tctacggatc atgcattttg tggtacgcct gtccggtttt ggccttattg    480
tggtttggtg ctggcgagta catgatgcgt cgtccgctgg cggtgctcgt ctccattgcg    540
ctgcccacgc tgtttctctg ctgggtcgat gtcgtcgcta ttggcgccgg cacatgggac    600
atttcgctgg ccacaagcac cggcaagttc gtcgtgcccc acctgccgt ggaggaattc    660 atgttctttg cgctaattaa taccgttttg gtatttggta cgtgtgcgat cgatcgcacg    720
atggcgatcc tccacctgtt caaaaacaag agtccttatc agcgcccata ccagcacagc    780
aagtcgttcc tccaccagat cctcgagatg acctgggcct ctgtttacc cgaccaagtg    840 ctgcattcag acacattcca cgacctgtcc gtcagctggg acatcctgcg caaggcctcc    900
aagtcctttt acacggcctc tgctgtcttt cccggcgacg tgcgccaaga gctcggtgtg    960
ctatacgcct tttgcagagc cacggacgat ctctgcgaca cgagcaggt ccctgtgcag   1020 acgcgaaagg agcagctgat actgacacat cagttcgtca gcgatctgtt tggccaaaag   1080
acaagcgcgc cgactgccat tgactgggac ttttacaacg accaactgcc tgcctcgtgc   1140
atctctgcct tcaagtcgtt cacccgtttg cgccatgtgc tggaagctgg agccatcaag   1200
gaactgctcg acgggtacaa gtgggatttg gagcgtcgct ccatcaggga tcaggaggat   1260
ctcagatatt actcagcttg tgtcgccagc agtgttggtg aaatgtgcac tcgcatcata   1320
ctggcccacg ccgacaagcc cgcctcccgc cagcaaacac agtggatcat tcagcgtgcg   1380
cgtgaaatgg gtctggtact ccaatataca aacattgcaa gagacattgt caccgacagc   1440
gaggaactgg gcagatgcta cctgcctcag gattggctta ccgagaagga ggtggcgctg   1500
attcaaggcg gccttgcccg agaaattggc gaggagcgat tgctctcact gtcgcatcgc   1560
ctcatctacc aggcagacga gctcatggtg gttgccaaca agggcatcga caagctgccc   1620
agccattgtc aaggcggcgt gcgtgcggcc tgcaacgtct atgcttccat ggcaccaag   1680 ctcaagtctt acaagcacca ctatcccagc agagcacatg tcggcaattc gaaacgagtg   1740
gaaattgctc ttcttagcgt atacaacctt tacaccgcgc caattgcgac tagtagtacc   1800
acacattgca gacagggaaa aatgagaaat ctaaatacca tttaa              1845
```

<210> SEQ ID NO 63
<211> LENGTH: 1845
<212> TYPE: DNA
<213> ORGANISM: Artificial Sequence
<220> FEATURE:
<223> OTHER INFORMATION: SYNTHESIZED

<400> SEQUENCE: 63

```
atgctgctga cttacatgga ggttcatctc tactacactc tgcctgttct gggcgttctg     60
tcttggctgt cccgacccta ctacactgcc actgacgctc tgaagttcaa gtttctgacc    120
ctcgttgcct tcaccactgc ctcggcttgg gataactaca tcgtctacca caaggcctgg    180
tcttactgcc ccacctgtgt tactgctgtc attggctacg tccctctgga ggagtacatg    240
ttctttatca ttatgaccct gctcactgtt gccttcacca acctcgtcat gcgatggcac    300
ctgcattcct tctttatccg acccgagacc cctgttatgc agtctgtcct ggtgcgactc    360
gtccccatca ccgccctgct cattactgcc tacaaggctt ggcacctcgc tgtgcccgga    420
aagcctctgt tctacggctc ctgcatcctc tggtacgcct gtcctgttct ggctctgctc    480
```

```
tggtttggtg ccggagagta catgatgcga cgacccctgg ccgttctcgt ctctattgct    540
ctgcctactc tgttcctctg ctgggtggac gtcgtggcta tcggagctgg cacctgggat    600
atttcgctcg ccacctccac tggcaagttc gttgtccccc acctgccgt ggaggagttt    660 atgttctttg ctctgatcaa caccgtgctc gttttcggta cttgcgccat cgaccgaacc    720
atggctattc tgcatctctt taagaacaag tctccctacc agcgacctta ccagcactct    780
aagtcgttcc tgcatcagat cctcgagatg acttgggcct tttgtctgcc cgaccaggtg    840
ctccactccg acaccttcca tgatctctcc gtttcttggg atattctgcg aaaggcctcg    900
aagtccttct acaccgcctc tgctgtcttt cccggtgacg tgcgacagga gctgggagtc    960
ctctacgcct tctgccgagc taccgacgat ctgtgtgaca acgagcaggt ccctgtgcag   1020
actcgaaagg agcagctgat cctcacccac cagttcgtgt cggacctctt tggtcagaag   1080
acctccgccc ccactgctat cgactgggat ttctacaacg accagctgcc tgcctcctgc   1140
atttctgctt tcaagtcctt tacccgactg cgacacgtcc tcgaggctgg agctatcaag   1200
gagctgctcg acggttacaa gtgggatctc gagcgacgat ctattcgaga ccaggaggat   1260
ctgcgatact actcggcctg cgtggcttcc tctgttggag agatgtgtac ccgaatcatt   1320
ctggctcacg ctgacaagcc tgcttcccga cagcagaccc agtggatcat tcagcgagct   1380
cgagagatgg gtctggtcct ccagtacact aacatcgccc gagacattgt gaccgattct   1440
gaggagctgg gacgatgtta cctccctcag gactggctga ccgagaagga ggtcgctctc   1500
atccagggag gtctggctcg agagattgga gaggagcgac tgctctctct gtcgcaccga   1560
ctcatctacc aggccgacga gctcatggtg gttgctaaca agggcattga taagctgcct   1620
tcccattgcc agggaggcgt gcgagccgct tgtaacgttt acgcctctat cggaaccaag   1680
ctgaagtcgt acaagcacca ttaccctcc cgagcccacg tcgcaactc taagcgagtg   1740 gagatcgctc tgctctctgt gtacaacctc tacaccgccc ctattgctac ttcgtccacc   1800
actcattgcc gacagggcaa gatgcgaaac ctgaacacca tctaa               1845
```

<210> SEQ ID NO 64
<211> LENGTH: 614
<212> TYPE: PRT
<213> ORGANISM: Mucor circinelloides

<400> SEQUENCE: 64

```
Met Leu Leu Thr Tyr Met Glu Val His Leu Tyr Tyr Thr Leu Pro Val
1               5                   10                  15

Leu Gly Val Leu Ser Trp Leu Ser Arg Pro Tyr Tyr Thr Ala Thr Asp
            20                  25                  30

Ala Leu Lys Phe Lys Phe Leu Thr Leu Val Ala Phe Thr Thr Ala Ser
        35                  40                  45

Ala Trp Asp Asn Tyr Ile Val Tyr His Lys Ala Trp Ser Tyr Cys Pro
    50                  55                  60

Thr Cys Val Thr Ala Val Ile Gly Tyr Val Pro Leu Glu Glu Tyr Met
65                  70                  75                  80

Phe Phe Ile Ile Met Thr Leu Leu Thr Val Ala Phe Thr Asn Leu Val
                85                  90                  95

Met Arg Trp His Leu His Ser Phe Phe Ile Arg Pro Glu Thr Pro Val
            100                 105                 110

Met Gln Ser Val Leu Val Arg Leu Val Pro Ile Thr Ala Leu Leu Ile
        115                 120                 125

Thr Ala Tyr Lys Ala Trp His Leu Ala Val Pro Gly Lys Pro Leu Phe
```

```
            130                 135                 140
Tyr Gly Ser Cys Ile Leu Trp Tyr Ala Cys Pro Val Leu Ala Leu Leu
145                 150                 155                 160

Trp Phe Gly Ala Gly Glu Tyr Met Met Arg Arg Pro Leu Ala Val Leu
                    165                 170                 175

Val Ser Ile Ala Leu Pro Thr Leu Phe Leu Cys Trp Val Asp Val Val
                180                 185                 190

Ala Ile Gly Ala Gly Thr Trp Asp Ile Ser Leu Ala Thr Ser Thr Gly
                195                 200                 205

Lys Phe Val Val Pro His Leu Pro Val Glu Glu Phe Met Phe Phe Ala
                210                 215                 220

Leu Ile Asn Thr Val Leu Val Phe Gly Thr Cys Ala Ile Asp Arg Thr
225                 230                 235                 240

Met Ala Ile Leu His Leu Phe Lys Asn Lys Ser Pro Tyr Gln Arg Pro
                245                 250                 255

Tyr Gln His Ser Lys Ser Phe Leu His Gln Ile Leu Glu Met Thr Trp
                260                 265                 270

Ala Phe Cys Leu Pro Asp Gln Val Leu His Ser Asp Thr Phe His Asp
                275                 280                 285

Leu Ser Val Ser Trp Asp Ile Leu Arg Lys Ala Ser Lys Ser Phe Tyr
                290                 295                 300

Thr Ala Ser Ala Val Phe Pro Gly Asp Val Arg Gln Glu Leu Gly Val
305                 310                 315                 320

Leu Tyr Ala Phe Cys Arg Ala Thr Asp Leu Cys Asp Asn Glu Gln
                325                 330                 335

Val Pro Val Gln Thr Arg Lys Glu Gln Leu Ile Leu Thr His Gln Phe
                340                 345                 350

Val Ser Asp Leu Phe Gly Gln Lys Thr Ser Ala Pro Thr Ala Ile Asp
                355                 360                 365

Trp Asp Phe Tyr Asn Asp Gln Leu Pro Ala Ser Cys Ile Ser Ala Phe
                370                 375                 380

Lys Ser Phe Thr Arg Leu Arg His Val Leu Glu Ala Gly Ala Ile Lys
385                 390                 395                 400

Glu Leu Leu Asp Gly Tyr Lys Trp Asp Leu Glu Arg Arg Ser Ile Arg
                405                 410                 415

Asp Gln Glu Asp Leu Arg Tyr Tyr Ser Ala Cys Val Ala Ser Ser Val
                420                 425                 430

Gly Glu Met Cys Thr Arg Ile Ile Leu Ala His Ala Asp Lys Pro Ala
                435                 440                 445

Ser Arg Gln Gln Thr Gln Trp Ile Ile Gln Arg Ala Arg Glu Met Gly
                450                 455                 460

Leu Val Leu Gln Tyr Thr Asn Ile Ala Arg Asp Ile Val Thr Asp Ser
465                 470                 475                 480

Glu Glu Leu Gly Arg Cys Tyr Leu Pro Gln Asp Trp Leu Thr Glu Lys
                485                 490                 495

Glu Val Ala Leu Ile Gln Gly Gly Leu Ala Arg Glu Ile Gly Glu Glu
                500                 505                 510

Arg Leu Leu Ser Leu Ser His Arg Leu Ile Tyr Gln Ala Asp Glu Leu
                515                 520                 525

Met Val Val Ala Asn Lys Gly Ile Asp Lys Leu Pro Ser His Cys Gln
                530                 535                 540

Gly Gly Val Arg Ala Ala Cys Asn Val Tyr Ala Ser Ile Gly Thr Lys
545                 550                 555                 560
```

```
Leu Lys Ser Tyr Lys His His Tyr Pro Ser Arg Ala His Val Gly Asn
            565                 570                 575

Ser Lys Arg Val Glu Ile Ala Leu Leu Ser Val Tyr Asn Leu Tyr Thr
        580                 585                 590

Ala Pro Ile Ala Thr Ser Ser Thr Thr His Cys Arg Gln Gly Lys Met
        595                 600                 605

Arg Asn Leu Asn Thr Ile
    610

<210> SEQ ID NO 65
<211> LENGTH: 1845
<212> TYPE: DNA
<213> ORGANISM: Artificial Sequence
<220> FEATURE:
<223> OTHER INFORMATION: SYNTHESIZED

<400> SEQUENCE: 65
```

| | | |
|---|---|---|
| atgctgctga cttacatgga ggttcatctc tactacactc tgcctgttct gggcgttctg | 60 |
| tcttggctgt cccgacccta ctacactgcc actgacgctc tgaagttcaa gtttctgacc | 120 |
| ctcgttgcct tcaccactgc ctcggcttgg gataactaca tcgtctacca caaggcctgg | 180 |
| tcttactgcc ccacctgtgt tactgctgtc attggctacg tccctctgga agtacatg | 240 |
| ttctttatca ttatgaccct gctcactgtt gccttcacca acctcgtcat gcgatggcac | 300 |
| ctgcattcct tctttatccg acccgagacc cctgttatgc agtctgtcct ggtgcgactc | 360 |
| gtccccatca ccgccctgct cattactgcc tacaaggctt ggcacctcgc tgtgcccgga | 420 |
| aagcctctgt tctacggctc ctgcatcctc tggtacgcct gtcctgttct ggctctgctc | 480 |
| tggtttggtg ccggagagta catgatgcga cgacccctgg ccgttctcgt ctctattgct | 540 |
| ctgcctactc tgttcctctg ctgggtggac gtcgtggcta tcggagctgg cacctgggat | 600 |
| atttcgctcg ccacctccac tggcaagttc gttgtccccc acctgtccgt ggaggagttt | 660 |
| atgttctttg ctctgatcaa caccgtgctc gtttttcggta cttgcgccat cgaccgaacc | 720 |
| atggctattc tgcatctctt taagaacaag tctccctacc agcgaccttac ccagcactct | 780 |
| aagtcgttcc tgcatcagat cctcgagatg acttgggcct tttgtctgcc cgaccaggtg | 840 |
| ctccactccg acaccttcca tgatctctcc gtttcttggg atattctgcg aaaggcctcg | 900 |
| aagtccttct acaccgcctc tgctgtcttt cccggtgacg tgcgacagga gctgggagtc | 960 |
| ctctacgcct ctgccgagc taccgacgat ctgtgtgaca cgagcaggt ccctgtgcag | 1020 |
| actcgaaagg agcagctgat cctcacccac cagttcgtgt cggacctctt tggtcagaag | 1080 |
| acctccgccc ccactgctat cgactgggat ttctacaacg accagctgcc tgcctcctgc | 1140 |
| atttctgctt tcaagtcctt taccccgactg cgacacgtcc tcgaggctgg agctatcaag | 1200 |
| gagctgctcg acggttacaa gtgggatctc gagcgacgat ctattcgaga ccaggaggat | 1260 |
| ctgcgatact actcggcctg cgtggcttcc tctgttggag agatgtgtac ccgaatcatt | 1320 |
| ctggctcacg ctgacaagcc tgcttcccga cagcagaccc agtggatcat tcagcgagct | 1380 |
| cgagagatgg gtctggtcct ccagtacact aacatcgccc gagacattgt gaccgattct | 1440 |
| gaggagctgg gacgatgtta cctccctcag gactggctga ccgagaagga ggtcgctctc | 1500 |
| atccagggag gtctggctcg agagattgga gaggagcgac tgctctctct gtcgcaccga | 1560 |
| ctcatctacc aggccgacga gctcatggtg gttgctaaca agggcattga taagctgcct | 1620 |
| tcccattgcc agggaggcgt gcgagccgct tgtaacgttt acgcctctat cggaaccaag | 1680 | ctgaagtcgt acaagcacca ttacccctcc cgagcccacg tcggcaactc taagcgagtg    1740 gagatcgctc tgctctctgt gtacaacctc tacaccgccc ctattgctac ttcgtccacc    1800 actcattgcc gacagggcaa gatgcgaaac ctgaacacca tctaa                    1845

<210> SEQ ID NO 66
<211> LENGTH: 1845
<212> TYPE: DNA
<213> ORGANISM: Artificial Sequence
<220> FEATURE:
<223> OTHER INFORMATION: SYNTHESIZED

<400> SEQUENCE: 66
atgctgctga cttacatgga ggttcatctc tactacactc tgcctgttct gggcgttctg     60
tcttggctgt cccgacccta ctacactgcc actgacgctc tgaagttcaa gtttctgacc    120
ctcgttgcct tcaccactgc ctcggcttgg gataactaca tcgtctacca caaggcctgg    180
tcttactgcc ccacctgtgt tactgctgtc attggctacg tccctctgga ggagtacatg    240
ttctttatca ttatgaccct gctcactgtt gccttcacca acctcgtcat gcgatggcac    300
ctgcattcct tctttatccg acccgagacc cctgttatgc agtctgtcct ggtgcgactc    360
gtccccatca ccgccctgct cattactgcc tacaaggctt ggcacctcgc tgtgcccgga    420
aagcctctgt tctacggctc ctgcatcctc tggtacgcct gtcctgttct ggctctgctc    480
tggtttggtg ccggagagta catgatgcga cgacccctgg ccgttctcgt ctctattgct    540
ctgcctactc tgttcctctg ctgggtggac gtcgtggcta tcggagctgg cacctgggat    600
atttcgctcg ccacctccac tggcaagttc gttgtccccc acctgcccgt ggaggagttt    660
atgttctttg ctctgatcaa caccgtgctc gttttcggta cttgcgccat cgaccgaacc    720
atggctattc tgcatctctt taagaacaag tctccctacc agcgacctta ccagcactct    780
aagtcgttcc tgcatcagat cctcgagatg acttgggcct tttgtctgcc cgaccaggtg    840
ctccactccg acaccttcca tgatctctcc gtttcttggg atattctgcg aaaggcctcg    900
aagtccttct acaccgcctc tgctgtcttt cccggtgacg tgcgacagga gctgggagtc    960
ctctacgcct ctgccgagc taccgacgat ctgtgtgaca cgagcaggt ccctgtgcag   1020 actcgaaagg agcagctgat cctcacccac cagttcgtgt cggacctctt tggtcagaag   1080
acctccgccc ccactgctat cgactgggat ttctacaacg accagctgcc tgcctcctgc   1140
atttctgctt tcaagtcctt tacccgactg cgacacgtcc tcgaggctgg agctatcaag   1200
gagctgctcg acggttacaa gtgggatctc gagcgacgat ctattcgaga ccaggaggat   1260
ctgcgatact actcggcctg cgtggcttcc tctgttggag agatgtgtac ccgaatcatt   1320
ctggctcacg ctgacaagcc tgcttcccga cagcagaccc agtggatcat tcagcgagct   1380
cgagagatgg gtctggtcct ccagtacact aacatcgccc gagacattgt gaccgattct   1440
gaggagctgg gacgatgtta cctccctcag gactggctga ccgagaagga ggtcgctctc   1500
atccagggag gtctggctcg agagattgga gaggagcgac tgctctctct gtcgcaccga   1560
ctcatctacc aggccgacga gctcatggtg gttgctaaca agggcattga taagctgcct   1620
tcccattgcc agggaggcgt gcgagccgct tgtaacgttt acgcctctat cggaaccaag   1680
ctgaagtcgt acaagcacca ttacccctcc cgagcccacg tcggcaactc taagcgagtg   1740
gagatcgctc tgctctctgt gtacaacctc tacaccgccc ctattgctac ttcgtccacc   1800
actcattgcc gacagggcaa gatgcgaaac ctgaacacca tctaa                   1845

<210> SEQ ID NO 67
<211> LENGTH: 1809
<212> TYPE: DNA
<213> ORGANISM: Phycomyces blakesleeanus

<400> SEQUENCE: 67

```
atgctgactt atatggaagt acatctgtac ttcaccctcc cggtgcttgc actgcttgcc      60
ttcctctaca agccattctt caccacaaag daccgcttca agtatatctt cctctgcact     120
gtcgcattcg ccactgcgtc tccctgggac aactacattg tataccacaa agcctggagc     180
tactgtccag agtgtgtcac ggctgtgatc ggatatgttc ctcttgaaga gtacatgttc     240
tttatcatca tgactctcat taccgtcaca tttactagtc tgacaatgcg ttggactctg     300
cccagtttct ttatcagacc agagaccccc gtattccagt ccgtttgtgt ccgctatatc     360
cctattgtcg gtttcttgac aatcgctgca aaggcctggg ccagcagtat ccccgattca     420
cacccctttt acggtgcttg tatcctctgg tacgtctgtc cagtccttgc ccttttgtgg     480
atcggctctg gtgaatacat gcttcgtcgc tggaaagcag tcctgttctc catcgctgtc     540
ccaaccatct tcttgtgctg ggttgaccaa tatgccattg cccgcggcac ctgggacatc     600
tccagacgca caagcactgg aatcatggtc ctgcccagtc ttcccttgga agaattcctc     660
ttcttcttgc tcatcgacac cgtacttgtg tttgcctcct gcgccaccga ccgtgcccac     720
gctatcgtcc atatctacat caccectatg aaccacaaca aggtcccac atggtacatg     780
gactttttct acctctgctg ggcattcctg cagaccgacc aggcactcag tggagaaacc     840
ctgagcgatc tcgatgccac atggcgtatt ccegtgaag cttcggcctc attctacact     900
gcctcttccg tgttctcctt tgaagcccgc caggacctcg gcgtgctcta tggcttctgc     960
cgtgccaccg atgaccttgc cgacaacaac gacgtgtccg tcccagaccg caagaagcag    1020
cttgaactcg tccgtggctt tgtgcgccag atgtttgata gcaagcacgg ccaccccgac    1080
atcgattgga cccagtacag cggcagcatt cctgactcgt ttatcgctgc cttccgcagc    1140
ttcacccgcc tccgggacgt tttggaaatc aaggccgtcg aggagctttt ggatggctac    1200
acctttgatc tcgaacagcg tgaggttaag aacgaagacg accttgtcta ctactctgcc    1260
tgcgtggcca gcagtgttgg cgagatgtgc accgtgtcc tgatggcttc tgagcccgga    1320
ggaaaccgca caatgctcaa gtggactgtg aacgtgcac gcgatatggg acttgccctc    1380
cagctcacca acattgcacg cgatatcgtg actgacagca aacagctcgg aagatcctac    1440
gtaccccgcg actggctgac cagccaagag tctgcattgc tcaaggctgg aaaggcccgc    1500
gagcttggtg acgagcgtct gcgccagatt gcactcaaga tggtctacac cgccgacgac    1560
ctcaacctga tggccagtcg tgcgatcgat tacttgcctc caagctctcg atgtggtgtc    1620
agagccgcct gcaacgtcta cactgccatt ggtgtctctc tccacaaggc taacggctat    1680
cccgatcgtg ctcacctgac caagctcgaa cgtatgaagg tcaccttcag atgcgtgtac    1740
ggcttccgga agggccacca gggtgttcaa ggtgatcgtg aaagtcaca ggcctttact    1800
gtcatttaa                                                            1809
```

<210> SEQ ID NO 68
<211> LENGTH: 1845
<212> TYPE: DNA
<213> ORGANISM: Artificial Sequence
<220> FEATURE:
<223> OTHER INFORMATION: SYNTHESIZED

<400> SEQUENCE: 68

| | |
|---|---|
| atgctattga catatatgga ggtccacctg tactacacct tacccgtttt aggagtgtta | 60 |
| tcttggctaa gtaggccata ctacactgcg actgacgcct tgaagtttaa gttcctgacg | 120 |
| cttgttgcat ttacgacggc atcagcttgg acaactata tcgtttacca caaagcctgg | 180 |
| agttattgtc cgacgtgtgt taccgccgtt ataggctacg ttcctttgga gaaatacatg | 240 |
| ttctttatca taatgacact actgacggtg gcatttacta acttggtaat gaggtggcac | 300 |
| cttcacagtt tctttattag accggaaact ccagtaatgc agtccgtctt agtaaggtta | 360 |
| gtgcctatca ccgccctact aataacggcg tataaagcgt ggcaccttgc cgtgcctgga | 420 |
| aaacccctat tctacggctc atgtatactt tggtatgctt gtcccgtctt ggctttgcta | 480 |
| tggttcgggg caggggagta catgatgcgt cgtcccttgg ctgttttagt aagcatagct | 540 |
| ttgcctactt tattcctgtg ttgggtcgat gtagtcgcca tcggcgccgg cacttgggat | 600 |
| atcagtttgg cgacgagtac tggtaaattt gtggtccccc atctatcagt agaggagttt | 660 |
| atgttttttg cattgataaa cacagtccta gtattcggta cctgtgcaat tgataggacg | 720 |
| atggctatat tgcacttatt caagaataaa agcccatatc agagacctta ccagcactca | 780 |
| aagagcttcc ttcaccaaat tctggagatg acttgggctt tttgtcttcc ggatcaggtg | 840 |
| cttcatagcg acaccttcca tgatctaagt gtatcctggg atatcctgag gaaggcttcc | 900 |
| aaaagcttct atacagccag cgcagtcttc cccggcgatg tgaggcagga gcttggggtc | 960 |
| ttgtacgcat tttgcagggc cacgatgac ttgtgtgaca atgagcaggt gcccgtacaa | 1020 |
| acccgtaaag agcaactgat actgacccat cagttcgtga gcgatttgtt cggacagaag | 1080 |
| acgtctgctc cgacagcaat cgactgggac ttctataatg accagttgcc ggcctcttgc | 1140 |
| attagcgctt tcaagtcatt tacgcgtcta agacatgtgc ttgaagcagg ggcaataaag | 1200 |
| gagcttcttg acggctacaa gtgggattta gaacgtagaa gcataagaga tcaagaagat | 1260 |
| ttgagatact acagtgcatg tgtcgcgtct tcagtaggtg aaatgtgcac taggattatt | 1320 |
| ctagcacatg ccgataaacc tgcttcacgt caacaaactc aatggatcat ccaaagagca | 1380 |
| agagaaatgg gtctggtgct tcagtatacg aatatagcac gtgacatagt aactgattcc | 1440 |
| gaggaattgg ggcgttgcta tctgccccag gactggttaa cggaaaagga agtcgcgtta | 1500 |
| atacaagggg gactggcgag agaaataggt gaagagcgtc tttttaagttt atctcataga | 1560 |
| ctaatctatc aagctgatga actaatggta gttgcaaata aggggataga caagctgccg | 1620 |
| agtcattgtc aaggggggtgt gcgtgcagca tgcaatgtgt acgcgagtat tggcacaaag | 1680 |
| ctaaagtcct acaaacacca ttatccgagc agagcccatg taggaaatag taagagggtg | 1740 |
| gagatagctc tattgagcgt ctacaatttg tatacggccc ctattgctac ctcatccacg | 1800 |
| acgcactgca ggcaaggtaa aatgagaaat tgaacacta tataa | 1845 |

<210> SEQ ID NO 69
<211> LENGTH: 614
<212> TYPE: PRT
<213> ORGANISM: Artificial Sequence
<220> FEATURE:
<223> OTHER INFORMATION: SYNTHESIZED

<400> SEQUENCE: 69

Met Leu Leu Thr Tyr Met Glu Val His Leu Tyr Tyr Thr Leu Pro Val
1               5                   10                  15

Leu Gly Val Leu Ser Trp Leu Ser Arg Pro Tyr Tyr Thr Ala Thr Asp
            20                  25                  30

Ala Leu Lys Phe Lys Phe Leu Thr Leu Val Ala Phe Thr Thr Ala Ser

```
                35                  40                  45
Ala Trp Asp Asn Tyr Ile Val Tyr His Lys Ala Trp Ser Tyr Cys Pro
 50                  55                  60

Thr Cys Val Thr Ala Val Ile Gly Tyr Val Pro Leu Glu Lys Tyr Met
 65                  70                  75                  80

Phe Phe Ile Ile Met Thr Leu Leu Thr Val Ala Phe Thr Asn Leu Val
                     85                  90                  95

Met Arg Trp His Leu His Ser Phe Phe Ile Arg Pro Gly Thr Pro Val
                    100                 105                 110

Met Gln Ser Val Leu Val Arg Leu Val Pro Ile Thr Ala Leu Leu Ile
                    115                 120                 125

Thr Ala Tyr Lys Ala Trp His Leu Ala Val Pro Gly Lys Pro Leu Phe
130                 135                 140

Tyr Gly Ser Cys Ile Leu Trp Tyr Ala Cys Pro Val Leu Ala Leu Leu
145                 150                 155                 160

Trp Phe Gly Ala Gly Glu Tyr Met Met Arg Arg Pro Leu Ala Val Leu
                    165                 170                 175

Val Ser Ile Ala Leu Pro Thr Leu Phe Leu Cys Trp Val Asp Val Val
                    180                 185                 190

Ala Ile Gly Ala Gly Thr Trp Asp Ile Ser Leu Ala Thr Ser Thr Gly
                    195                 200                 205

Lys Phe Val Val Pro His Leu Ser Val Glu Glu Phe Met Phe Phe Ala
210                 215                 220

Leu Ile Asn Thr Val Leu Val Phe Gly Thr Cys Ala Ile Asp Arg Thr
225                 230                 235                 240

Met Ala Ile Leu His Leu Phe Lys Asn Lys Ser Pro Tyr Gln Arg Pro
                    245                 250                 255

Tyr Gln His Ser Lys Ser Phe Leu His Gln Ile Leu Glu Met Thr Trp
                    260                 265                 270

Ala Phe Cys Leu Pro Asp Gln Val Leu His Ser Asp Thr Phe His Asp
                    275                 280                 285

Leu Ser Val Ser Trp Asp Ile Leu Arg Lys Ala Ser Lys Ser Phe Tyr
290                 295                 300

Thr Ala Ser Ala Val Phe Pro Gly Asp Val Arg Gln Glu Leu Gly Val
305                 310                 315                 320

Leu Tyr Ala Phe Cys Arg Ala Thr Asp Asp Leu Cys Asp Asn Glu Gln
                    325                 330                 335

Val Pro Val Gln Thr Arg Lys Glu Gln Leu Ile Leu Thr His Gln Phe
                    340                 345                 350

Val Ser Asp Leu Phe Gly Gln Lys Thr Ser Ala Pro Thr Ala Ile Asp
                    355                 360                 365

Trp Asp Phe Tyr Asn Asp Gln Leu Pro Ala Ser Cys Ile Ser Ala Phe
                    370                 375                 380

Lys Ser Phe Thr Arg Leu Arg His Val Leu Glu Ala Gly Ala Ile Lys
385                 390                 395                 400

Glu Leu Leu Asp Gly Tyr Lys Trp Asp Leu Glu Arg Arg Ser Ile Arg
                    405                 410                 415

Asp Gln Glu Asp Leu Arg Tyr Tyr Ser Ala Cys Val Ala Ser Ser Val
                    420                 425                 430

Gly Glu Met Cys Thr Arg Ile Ile Leu Ala His Ala Asp Lys Pro Ala
                    435                 440                 445

Ser Arg Gln Gln Thr Gln Trp Ile Ile Gln Arg Ala Arg Glu Met Gly
450                 455                 460
```

```
Leu Val Leu Gln Tyr Thr Asn Ile Ala Arg Asp Ile Val Thr Asp Ser
465                 470                 475                 480

Glu Glu Leu Gly Arg Cys Tyr Leu Pro Gln Asp Trp Leu Thr Glu Lys
                485                 490                 495

Glu Val Ala Leu Ile Gln Gly Gly Leu Ala Arg Glu Ile Gly Glu Glu
            500                 505                 510

Arg Leu Leu Ser Leu Ser His Arg Leu Ile Tyr Gln Ala Asp Glu Leu
            515                 520                 525

Met Val Val Ala Asn Lys Gly Ile Asp Lys Leu Pro Ser His Cys Gln
530                 535                 540

Gly Gly Val Arg Ala Ala Cys Asn Val Tyr Ala Ser Ile Gly Thr Lys
545                 550                 555                 560

Leu Lys Ser Tyr Lys His His Tyr Pro Ser Arg Ala His Val Gly Asn
                565                 570                 575

Ser Lys Arg Val Glu Ile Ala Leu Leu Ser Val Tyr Asn Leu Tyr Thr
            580                 585                 590

Ala Pro Ile Ala Thr Ser Ser Thr Thr His Cys Arg Gln Gly Lys Met
            595                 600                 605

Arg Asn Leu Asn Thr Ile
    610

<210> SEQ ID NO 70
<211> LENGTH: 984
<212> TYPE: DNA
<213> ORGANISM: Yarrowia lipolytica

<400> SEQUENCE: 70
atggattata acagcgcgga tttcaaggag atatggggca aggccgccga caccgcgctg      60
ctgggaccgt acaactacct cgccaacaac cggggccaca catcagaga cacttgatc      120 gcagcgttcg gagcggttat caaggtggac aagagcgatc tcgagaccat ttcgcacatc      180
accaagattt tgcataactc gtcgctgctt gttgatgacg tggaagacaa ctcgatgctc      240
cgacgaggcc tgccggcagc ccattgtctg tttggagtcc cccaaaccat caactccgcc      300
aactacatgt actttgtggc tctgcaggag gtgctcaagc tcaagtctta tgatgccgtc      360
tccattttca ccgaggaaat gatcaacttg catagaggtc agggtatgga tctctactgg      420
agagaaacac tcacttgccc ctcggaagac gagtatctgg agatggtggt gcacaagacc      480
ggtggactgt ttcggctggc tctgagactt atgctgtcgg tggcatcgaa acaggaggac      540
catgaaaaga tcaactttga tctcacacac cttaccgaca cactgggagt catttaccag      600
attctggatg attacctcaa cctgcagtcc acggaattga ccgagaacaa gggattctgc      660
gaagatatca gcgaaggaaa gtttcgtttt ccgctgattc acagcatacg caccaacccg      720
gataaccacg agattctcaa cattctcaaa cagcgaacaa gcgacgcttc actcaaaaag      780
tacgccgtgg actacatgag aacagaaacc aagagtttcg actactgcct caagaggata      840
caggccatgt cactcaaggc aagttcgtac attgatgatc tagcagcagc tggccacgat      900
gtctccaagc tacgagccat tttgcattat tttgtgtcca cctctgactg tgaggagaga      960
aagtactttg aggatgcgca gtga                                             984

<210> SEQ ID NO 71
<211> LENGTH: 327
<212> TYPE: PRT
<213> ORGANISM: Yarrowia lipolytica
```

<400> SEQUENCE: 71

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325
```

<210> SEQ ID NO 72
<211> LENGTH: 1035
<212> TYPE: DNA
<213> ORGANISM: Yarrowia lipolytica

<400> SEQUENCE: 72

```
atgtccaagg cgaaattcga aagcgtgttc ccccgaatct ccgaggagct ggtgcagctg      60
ctgcgagacg agggtctgcc ccaggatgcc gtgcagtggt tttccgactc acttcagtac    120
aactgtgtgg gtggaaagct caaccgaggc ctgtctgtgg tcgacaccta ccagctactg    180
```

| | |
|---|---|
| accggcaaga aggagctcga tgacgaggag tactaccgac tcgcgctgct cggctggctg | 240 |
| attgagctgc tgcaggcgtt tttcctcgtg tcggacgaca ttatggatga gtccaagacc | 300 |
| cgacgaggcc agccctgctg gtacctcaag cccaaggtcg gcatgattgc catcaacgat | 360 |
| gctttcatgc tagagagtgg catctacatt ctgcttaaga agcatttccg acaggagaag | 420 |
| tactacattg accttgtcga gctgttccac gacatttcgt tcaagaccga gctgggccag | 480 |
| ctggtggatc ttctgactgc ccccgaggat gaggttgatc tcaaccggtt ctctctggac | 540 |
| aagcactcct ttattgtgcg atacaagact gcttactact ccttctacct gcccgttgtt | 600 |
| ctagccatgt acgtggccgg cattaccaac cccaaggacc tgcagcaggc catggatgtg | 660 |
| ctgatccctc tcggagagta cttccaggtc caggacgact accttgacaa ctttggagac | 720 |
| cccgagttca ttggtaagat cggcaccgac atccaggaca caagtgctc ctggctcgtt | 780 |
| aacaaagccc ttcagaaggc cacccccgag cagcgacaga tcctcgagga caactacggc | 840 |
| gtcaaggaca agtccaagga gctcgtcatc aagaaactgt atgatgacat gaagattgag | 900 |
| caggactacc ttgactacga ggaggaggtt gttggcgaca tcaagaagaa gatcgagcag | 960 |
| gttgacgaga gccgaggctt caagaaggag gtgctcaacg ctttcctcgc caagatttac | 1020 |
| aagcgacaga agtag | 1035 |

<210> SEQ ID NO 73
<211> LENGTH: 2028
<212> TYPE: DNA
<213> ORGANISM: Artificial Sequence
<220> FEATURE:
<223> OTHER INFORMATION: SYNTHESIZED

<400> SEQUENCE: 73

| | |
|---|---|
| atgtccaagg cgaaattcga aagcgtgttc ccccgaatct ccgaggagct ggtgcagctg | 60 |
| ctgcgagacg agggtctgcc ccaggatgcc gtgcagtggt tttccgactc acttcagtac | 120 |
| aactgtgtgg gtgaaagct caaccgaggc ctgtctgtgg tcgacaccta ccagctactg | 180 |
| accggcaaga aggagctcga tgacgaggag tactaccgac tcgcgctgct cggctggctg | 240 |
| attgagctgc tgcaggcgtt tttcctcgtg tcggacgaca ttatggatga gtccaagacc | 300 |
| cgacgaggcc agccctgctg gtacctcaag cccaaggtcg gcatgattgc catcaacgat | 360 |
| gctttcatgc tagagagtgg catctacatt ctgcttaaga agcatttccg acaggagaag | 420 |
| tactacattg accttgtcga gctgttccac gacatttcgt tcaagaccga gctgggccag | 480 |
| ctggtggatc ttctgactgc ccccgaggat gaggttgatc tcaaccggtt ctctctggac | 540 |
| aagcactcct ttattgtgcg atacaagact gcttactact ccttctacct gcccgttgtt | 600 |
| ctagccatgt acgtggccgg cattaccaac cccaaggacc tgcagcaggc catggatgtg | 660 |
| ctgatccctc tcggagagta cttccaggtc caggacgact accttgacaa ctttggagac | 720 |
| cccgagttca ttggtaagat cggcaccgac atccaggaca caagtgctc ctggctcgtt | 780 |
| aacaaagccc ttcagaaggc cacccccgag cagcgacaga tcctcgagga caactacggc | 840 |
| gtcaaggaca agtccaagga gctcgtcatc aagaaactgt atgatgacat gaagattgag | 900 |
| caggactacc ttgactacga ggaggaggtt gttggcgaca tcaagaagaa gatcgagcag | 960 |
| gttgacgaga gccgaggctt caagaaggag gtgctcaacg ctttcctcgc caagatttac | 1020 |
| aagcgacaga agggtggtgg ttctatggat tataacagcg cggatttcaa ggagatatgg | 1080 |
| ggcaaggccc ccgacaccgc gctgctggga ccgtacaact acctcgccaa caccgggggc | 1140 |
| cacaacatca gagaacactt gatcgcagcg ttcggagcgg ttatcaaggt ggacaagagc | 1200 |

```
gatctcgaga ccatttcgca catcaccaag attttgcata actcgtcgct gcttgttgat  1260
gacgtggaag acaactcgat gctccgacga ggcctgccgg cagcccattg tctgtttgga  1320
gtcccccaaa ccatcaactc cgccaactac atgtactttg tggctctgca ggaggtgctc  1380
aagctcaagt cttatgatgc cgtctccatt ttcaccgagg aaatgatcaa cttgcataga  1440
ggtcagggta tggatctcta ctggagagaa acactcactt gcccctcgga agacgagtat  1500
ctggagatgg tggtgcacaa gaccggtgga ctgtttcggc tggctctgag acttatgctg  1560
tcggtggcat cgaaacagga ggaccatgaa aagatcaact ttgatctcac acaccttacc  1620
gacacactgg gagtcattta ccagattctg gatgattacc tcaacctgca gtccacggaa  1680
ttgaccgaga acaagggatt ctgcgaagat atcagcgaag gaaagttttc gtttccgctg  1740
attcacagca tacgcaccaa cccggataac cacgagattc tcaacattct caaacagcga  1800
acaagcgacg cttcactcaa aaagtacgcc gtggactaca tgagaacaga accaagagt   1860
ttcgactact gcctcaagag gatacaggcc atgtcactca aggcaagttc gtacattgat  1920
gatctagcag cagctggcca cgatgtctcc aagctacgag ccattttgca ttattttgtg  1980
tccacctctg actgtgagga gagaaagtac tttgaggatg cgcagtga               2028
```

<210> SEQ ID NO 74
<211> LENGTH: 675
<212> TYPE: PRT
<213> ORGANISM: Artificial Sequence
<220> FEATURE:
<223> OTHER INFORMATION: SYNTHESIZED

<400> SEQUENCE: 74

```
Met Ser Lys Ala Lys Phe Glu Ser Val Phe Pro Arg Ile Ser Glu Glu
1               5                   10                  15

Leu Val Gln Leu Leu Arg Asp Glu Gly Leu Pro Gln Asp Ala Val Gln
            20                  25                  30

Trp Phe Ser Asp Ser Leu Gln Tyr Asn Cys Val Gly Gly Lys Leu Asn
        35                  40                  45

Arg Gly Leu Ser Val Val Asp Thr Tyr Gln Leu Leu Thr Gly Lys Lys
    50                  55                  60

Glu Leu Asp Asp Glu Glu Tyr Tyr Arg Leu Ala Leu Leu Gly Trp Leu
65                  70                  75                  80

Ile Glu Leu Leu Gln Ala Phe Phe Leu Val Ser Asp Asp Ile Met Asp
                85                  90                  95

Glu Ser Lys Thr Arg Arg Gly Gln Pro Cys Trp Tyr Leu Lys Pro Lys
            100                 105                 110

Val Gly Met Ile Ala Ile Asn Asp Ala Phe Met Leu Glu Ser Gly Ile
        115                 120                 125

Tyr Ile Leu Leu Lys Lys His Phe Arg Gln Glu Lys Tyr Tyr Ile Asp
    130                 135                 140

Leu Val Glu Leu Phe His Asp Ile Ser Phe Lys Thr Glu Leu Gly Gln
145                 150                 155                 160

Leu Val Asp Leu Leu Thr Ala Pro Glu Asp Glu Val Asp Leu Asn Arg
                165                 170                 175

Phe Ser Leu Asp Lys His Ser Phe Ile Val Arg Tyr Lys Thr Ala Tyr
            180                 185                 190

Tyr Ser Phe Tyr Leu Pro Val Val Leu Ala Met Tyr Val Ala Gly Ile
        195                 200                 205

Thr Asn Pro Lys Asp Leu Gln Gln Ala Met Asp Val Leu Ile Pro Leu
```

-continued

```
            210                 215                 220
Gly Glu Tyr Phe Gln Val Gln Asp Asp Tyr Leu Asp Asn Phe Gly Asp
225                 230                 235                 240

Pro Glu Phe Ile Gly Lys Ile Gly Thr Asp Ile Gln Asp Asn Lys Cys
                    245                 250                 255

Ser Trp Leu Val Asn Lys Ala Leu Gln Lys Ala Thr Pro Glu Gln Arg
                260                 265                 270

Gln Ile Leu Glu Asp Asn Tyr Gly Val Lys Asp Lys Ser Lys Glu Leu
                275                 280                 285

Val Ile Lys Lys Leu Tyr Asp Asp Met Lys Ile Glu Gln Asp Tyr Leu
            290                 295                 300

Asp Tyr Glu Glu Val Val Gly Asp Ile Lys Lys Ile Glu Gln
305                 310                 315                 320

Val Asp Glu Ser Arg Gly Phe Lys Lys Glu Val Leu Asn Ala Phe Leu
                    325                 330                 335

Ala Lys Ile Tyr Lys Arg Gln Lys Gly Gly Ser Met Asp Tyr Asn
                    340                 345                 350

Ser Ala Asp Phe Lys Glu Ile Trp Gly Lys Ala Ala Asp Thr Ala Leu
                355                 360                 365

Leu Gly Pro Tyr Asn Tyr Leu Ala Asn Asn Arg Gly His Asn Ile Arg
            370                 375                 380

Glu His Leu Ile Ala Ala Phe Gly Ala Val Ile Lys Val Asp Lys Ser
385                 390                 395                 400

Asp Leu Glu Thr Ile Ser His Ile Thr Lys Ile Leu His Asn Ser Ser
                    405                 410                 415

Leu Leu Val Asp Asp Val Glu Asp Asn Ser Met Leu Arg Arg Gly Leu
                420                 425                 430

Pro Ala Ala His Cys Leu Phe Gly Val Pro Gln Thr Ile Asn Ser Ala
                435                 440                 445

Asn Tyr Met Tyr Phe Val Ala Leu Gln Glu Val Leu Lys Leu Lys Ser
            450                 455                 460

Tyr Asp Ala Val Ser Ile Phe Thr Glu Glu Met Ile Asn Leu His Arg
465                 470                 475                 480

Gly Gln Gly Met Asp Leu Tyr Trp Arg Glu Thr Leu Thr Cys Pro Ser
                    485                 490                 495

Glu Asp Glu Tyr Leu Glu Met Val Val His Lys Thr Gly Gly Leu Phe
                500                 505                 510

Arg Leu Ala Leu Arg Leu Met Leu Ser Val Ala Ser Lys Gln Glu Asp
            515                 520                 525

His Glu Lys Ile Asn Phe Asp Leu Thr His Leu Thr Asp Thr Leu Gly
            530                 535                 540

Val Ile Tyr Gln Ile Leu Asp Asp Tyr Leu Asn Leu Gln Ser Thr Glu
545                 550                 555                 560

Leu Thr Glu Asn Lys Gly Phe Cys Glu Asp Ile Ser Glu Gly Lys Phe
                    565                 570                 575

Ser Phe Pro Leu Ile His Ser Ile Arg Thr Asn Pro Asp Asn His Glu
                580                 585                 590

Ile Leu Asn Ile Leu Lys Gln Arg Thr Ser Asp Ala Ser Leu Lys Lys
            595                 600                 605

Tyr Ala Val Asp Tyr Met Arg Thr Glu Thr Lys Ser Phe Asp Tyr Cys
            610                 615                 620

Leu Lys Arg Ile Gln Ala Met Ser Leu Lys Ala Ser Ser Tyr Ile Asp
625                 630                 635                 640
```

Asp Leu Ala Ala Ala Gly His Asp Val Ser Lys Leu Arg Ala Ile Leu
                645                 650                 655

His Tyr Phe Val Ser Thr Ser Asp Cys Glu Glu Arg Lys Tyr Phe Glu
            660                 665                 670

Asp Ala Gln
        675

<210> SEQ ID NO 75
<211> LENGTH: 1059
<212> TYPE: DNA
<213> ORGANISM: Saccharomyces cerevisiae

<400> SEQUENCE: 75

```
atggcttcag aaaagaaat taggagagag agattcttga acgttttccc taaattagta      60
gaggaattga acgcatcgct tttggcttac ggtatgccta aggaagcatg tgactggtat    120
gcccactcat tgaactacaa cactccaggc ggtaagctaa atagaggttt gtccgttgtg    180
gacacgtatg ctattctctc caacaagacc gttgaacaat tggggcaaga agaatacgaa    240
aaggttgcca ttctaggttg gtgcattgag ttgttgcagg cttacttctt ggtcgccgat    300
gatatgatgg acaagtccat taccagaaga ggccaaccat gttggtacaa ggttcctgaa    360
gttggggaaa ttgccatcaa tgacgcattc atgttagagg ctgctatcta caagcttttg    420
aaatctcact tcagaaacga aaatactac atagatatca ccgaattgtt ccatgaggtc    480
accttccaaa ccgaattggg ccaattgatg gacttaatca ctgcacctga agacaaagtc    540
gacttgagta agttctccct aaagaagcac tccttcatag ttactttcaa gactgcttac    600
tattctttct acttgcctgt cgcattggcc atgtacgttg ccggtatcac ggatgaaaag    660
gatttgaaac aagccagaga tgtcttgatt ccattgggtg aatacttcca aattcaagat    720
gactacttag actgcttcgg taccccagaa cagatcggta agatcggtac agatatccaa    780
gataacaaat gttcttgggt aatcaacaag gcattggaac ttgcttccgc agaacaaaga    840
aagactttag acgaaaatta cggtaagaag gactcagtcg cagaagccaa atgcaaaaag    900
attttcaatg acttgaaaat tgaacagcta taccacgaat atgaagagtc tattgccaag    960
gatttgaagg ccaaaatttc tcaggtcgat gagtctcgtg gcttcaaagc tgatgtctta   1020
actgcgttct tgaacaaagt ttacaagaga agcaaatag                         1059
```

<210> SEQ ID NO 76
<211> LENGTH: 352
<212> TYPE: PRT
<213> ORGANISM: Saccharomyces cerevisiae

<400> SEQUENCE: 76

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
                100                 105                 110

Pro Cys Trp Tyr Lys Val Pro Glu Val Gly Glu Ile Ala Ile Asn Asp
            115                 120                 125

Ala Phe Met Leu Glu Ala Ala Ile Tyr Lys Leu Leu Lys Ser His Phe
130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350

<210> SEQ ID NO 77
<211> LENGTH: 1008
<212> TYPE: DNA
<213> ORGANISM: Saccharomyces cerevisiae

<400> SEQUENCE: 77
atggaggcca agatagatga gctgatcaat aatgatcctg tttggtccag ccaaaatgaa      60
agcttgattt caaaacctta taatcacatc cttttgaaac ctggcaagaa ctttagacta     120
aatttaatag ttcaaattaa cagagttatg aatttgccca agaccagct ggccatagtt      180 tcgcaaattg ttgagctctt gcataattcc agccttttaa tcgacgatat agaagataat     240
gctcccttga aaggggaca gaccacttct cacttaatct tcggtgtacc ctccactata     300
aacaccgcaa attatatgta tttcagagcc atgcaacttg tatcgcagct aaccacaaaa     360
gagcctttgt atcataattt gattacgatt tcaacgaag aattgatcaa tctacatagg      420
ggacaaggct tggatatata ctggagagac tttctgcctg aaatcatacc tactcaggag     480
atgtatttga atatggttat gaataaaaca ggcggccttt tcagattaac gttgagactc     540
atggaagcgc tgtctccttc ctcacaccac ggccattcgt tggttccttt cataaatctt     600
ctgggtatta tttatcagat tagagatgat tacttgaatt tgaaagattt ccaaatgtcc     660

```
agcgaaaaag gctttgctga ggacattaca gaggggaagt tatctttcc catcgtccac      720 gcccttaact tcactaaaac gaaaggtcaa actgagcaac acaatgaaat tctaagaatt      780
ctcctgttga ggacaagtga taaagatata aaactaaagc tgattcaaat actggaattc      840
gacaccaatt cattggccta caccaaaaat tttattaatc aattagtgaa tatgataaaa      900
aatgataatg aaaataagta tttacctgat ttggcttcgc attccgacac cgccaccaat      960
ttacatgacg aattgttata tataatagac cacttatccg aattgtga                  1008
```

```
<210> SEQ ID NO 78
<211> LENGTH: 335
<212> TYPE: PRT
<213> ORGANISM: Saccharomyces cerevisiae

<400> SEQUENCE: 78

Met Glu Ala Lys Ile Asp Glu Leu Ile Asn Asn Asp Pro Val Trp Ser
1               5                   10                  15

Ser Gln Asn Glu Ser Leu Ile Ser Lys Pro Tyr Asn His Ile Leu Leu
                20                  25                  30

Lys Pro Gly Lys Asn Phe Arg Leu Asn Leu Ile Val Gln Ile Asn Arg
        35                  40                  45

Val Met Asn Leu Pro Lys Asp Gln Leu Ala Ile Val Ser Gln Ile Val
    50                  55                  60

Glu Leu Leu His Asn Ser Ser Leu Leu Ile Asp Asp Ile Glu Asp Asn
65                  70                  75                  80

Ala Pro Leu Arg Arg Gly Gln Thr Thr Ser His Leu Ile Phe Gly Val
                85                  90                  95

Pro Ser Thr Ile Asn Thr Ala Asn Tyr Met Tyr Phe Arg Ala Met Gln
            100                 105                 110

Leu Val Ser Gln Leu Thr Thr Lys Glu Pro Leu Tyr His Asn Leu Ile
        115                 120                 125

Thr Ile Phe Asn Glu Glu Leu Ile Asn Leu His Arg Gly Gln Gly Leu
    130                 135                 140

Asp Ile Tyr Trp Arg Asp Phe Leu Pro Glu Ile Ile Pro Thr Gln Glu
145                 150                 155                 160

Met Tyr Leu Asn Met Val Met Asn Lys Thr Gly Gly Leu Phe Arg Leu
                165                 170                 175

Thr Leu Arg Leu Met Glu Ala Leu Ser Pro Ser Ser His His Gly His
            180                 185                 190

Ser Leu Val Pro Phe Ile Asn Leu Leu Gly Ile Ile Tyr Gln Ile Arg
        195                 200                 205

Asp Asp Tyr Leu Asn Leu Lys Asp Phe Gln Met Ser Ser Glu Lys Gly
    210                 215                 220

Phe Ala Glu Asp Ile Thr Glu Gly Lys Leu Ser Phe Pro Ile Val His
225                 230                 235                 240

Ala Leu Asn Phe Thr Lys Thr Lys Gly Gln Thr Glu Gln His Asn Glu
                245                 250                 255

Ile Leu Arg Ile Leu Leu Leu Arg Thr Ser Asp Lys Asp Ile Lys Leu
            260                 265                 270

Lys Leu Ile Gln Ile Leu Glu Phe Asp Thr Asn Ser Leu Ala Tyr Thr
        275                 280                 285

Lys Asn Phe Ile Asn Gln Leu Val Asn Met Ile Lys Asn Asp Asn Glu
    290                 295                 300

Asn Lys Tyr Leu Pro Asp Leu Ala Ser His Ser Asp Thr Ala Thr Asn
305                 310                 315                 320
```

Leu His Asp Glu Leu Leu Tyr Ile Ile Asp His Leu Ser Glu Leu
            325                 330                 335

<210> SEQ ID NO 79
<211> LENGTH: 2076
<212> TYPE: DNA
<213> ORGANISM: Artificial Sequence
<220> FEATURE:
<223> OTHER INFORMATION: SYNTHESIZED

<400> SEQUENCE: 79

| | | | | | |
|---|---|---|---|---|---|
| atggcttcag | aaaagaaat | taggagagag | agattcttga | acgttttccc | taaattagta | 60 |
| gaggaattga | acgcatcgct | tttggcttac | ggtatgccta | aggaagcatg | tgactggtat | 120 |
| gcccactcat | tgaactacaa | cactccaggc | ggtaagctaa | atagaggttt | gtccgttgtg | 180 |
| gacacgtatg | ctattctctc | caacaagacc | gttgaacaat | ggggcaaga | agaatacgaa | 240 |
| aaggttgcca | ttctaggttg | gtgcattgag | ttgttgcagg | cttacttctt | ggtcgccgat | 300 |
| gatatgatgg | acaagtccat | taccagaaga | ggccaaccta | gttggtacaa | ggttcctgaa | 360 |
| gttggggaaa | ttgccatcaa | tgacgcattc | atgttagagg | ctgctatcta | caagcttttg | 420 |
| aaatctcact | tcagaaacga | aaaatactac | atagatatca | ccgaattgtt | ccatgaggtc | 480 |
| accttccaaa | ccgaattggg | ccaattgatg | gacttaatca | ctgcacctga | agacaaagtc | 540 |
| gacttgagta | agttctccct | aaagaagcac | tccttcatag | ttactttcaa | gactgcttac | 600 |
| tattctttct | acttgcctgt | cgcattggcc | atgtacgttg | ccggtatcac | ggatgaaaag | 660 |
| gatttgaaac | aagccagaga | tgtcttgatt | ccattgggtg | aatacttcca | aattcaagat | 720 |
| gactacttag | actgcttcgg | taccccagaa | cagatcggta | agatcggtac | agatatccaa | 780 |
| gataacaaat | gttcttgggt | aatcaacaag | gcattggaac | ttgcttccgc | agaacaaaga | 840 |
| aagactttag | acgaaaatta | cggtaagaag | gactcagtcg | cagaagccaa | atgcaaaaag | 900 |
| attttcaatg | acttgaaaat | tgaacagcta | taccacgaat | atgaagagtc | tattgccaag | 960 |
| gatttgaagg | ccaaaatttc | tcaggtcgat | gagtctcgtg | gcttcaaagc | tgatgtctta | 1020 |
| actgcgttct | tgaacaaagt | ttacaagaga | agcaaaggtg | gtggttctat | ggaggccaag | 1080 |
| atagatgagc | tgatcaataa | tgatcctgtt | tggtccagcc | aaaatgaaag | cttgatttca | 1140 |
| aaaccttata | tcacatcct | tttgaaacct | ggcaagaact | ttagactaaa | tttaatagtt | 1200 |
| caaattaaca | gagttatgaa | tttgcccaaa | gaccagctgg | ccatagtttc | gcaaattgtt | 1260 |
| gagctcttgc | ataattccag | ccttttaatc | gacgatatag | aagataatgc | tcccttgaga | 1320 |
| aggggacaga | ccacttctca | cttaatcttc | ggtgtaccct | ccactataaa | caccgcaaat | 1380 |
| tatatgtatt | tcagagccat | gcaacttgta | tcgcagctaa | ccacaaaaga | gcctttgtat | 1440 |
| cataatttga | ttacgatttt | caacgaagaa | ttgatcaatc | tacatagggg | acaaggcttg | 1500 |
| gatatatact | ggagagactt | tctgcctgaa | atcataccta | ctcaggagat | gtatttgaat | 1560 |
| atggttatga | ataaaacagg | cggcctttc | agattaacgt | tgagactcat | ggaagcgctg | 1620 |
| tctccttcct | cacaccacgg | ccattcgttg | gttcctttca | taaatcttct | gggtattatt | 1680 |
| tatcagatta | gagatgatta | cttgaatttg | aaagatttcc | aaatgtccag | cgaaaaaggc | 1740 |
| tttgctgagg | acattacaga | ggggaagtta | tcttttccca | tcgtccacgc | ccttaacttc | 1800 |
| actaaaacga | aggtcaaac | tgagcaacac | aatgaaattc | taagaattct | cctgttgagg | 1860 |
| acaagtgata | aagatataaa | actaaagctg | attcaaatac | tggaattcga | caccaattca | 1920 |
| ttggcctaca | ccaaaaattt | tattaatcaa | ttagtgaata | tgataaaaaa | tgataatgaa | 1980 |

```
aataagtatt tacctgattt ggcttcgcat tccgacaccg ccaccaattt acatgacgaa    2040
ttgttatata taatagacca cttatccgaa ttgtga                              2076
```

<210> SEQ ID NO 80
<211> LENGTH: 691
<212> TYPE: PRT
<213> ORGANISM: Artificial Sequence
<220> FEATURE:
<223> OTHER INFORMATION: SYNTHESIZED

<400> SEQUENCE: 80

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
```

```
                    340                 345                 350
Gly Gly Gly Ser Met Glu Ala Lys Ile Asp Glu Leu Ile Asn Asn Asp
            355                 360                 365

Pro Val Trp Ser Ser Gln Asn Glu Ser Leu Ile Ser Lys Pro Tyr Asn
        370                 375                 380

His Ile Leu Leu Lys Pro Gly Lys Asn Phe Arg Leu Asn Leu Ile Val
385                 390                 395                 400

Gln Ile Asn Arg Val Met Asn Leu Pro Lys Asp Gln Leu Ala Ile Val
                405                 410                 415

Ser Gln Ile Val Glu Leu Leu His Asn Ser Ser Leu Leu Ile Asp Asp
            420                 425                 430

Ile Glu Asp Asn Ala Pro Leu Arg Arg Gly Gln Thr Thr Ser His Leu
        435                 440                 445

Ile Phe Gly Val Pro Ser Thr Ile Asn Thr Ala Asn Tyr Met Tyr Phe
    450                 455                 460

Arg Ala Met Gln Leu Val Ser Gln Leu Thr Thr Lys Glu Pro Leu Tyr
465                 470                 475                 480

His Asn Leu Ile Thr Ile Phe Asn Glu Glu Leu Ile Asn Leu His Arg
                485                 490                 495

Gly Gln Gly Leu Asp Ile Tyr Trp Arg Asp Phe Leu Pro Glu Ile Ile
            500                 505                 510

Pro Thr Gln Glu Met Tyr Leu Asn Met Val Met Asn Lys Thr Gly Gly
        515                 520                 525

Leu Phe Arg Leu Thr Leu Arg Leu Met Glu Ala Leu Ser Pro Ser Ser
    530                 535                 540

His His Gly His Ser Leu Val Pro Phe Ile Asn Leu Leu Gly Ile Ile
545                 550                 555                 560

Tyr Gln Ile Arg Asp Asp Tyr Leu Asn Leu Lys Asp Phe Gln Met Ser
                565                 570                 575

Ser Glu Lys Gly Phe Ala Glu Asp Ile Thr Glu Gly Lys Leu Ser Phe
            580                 585                 590

Pro Ile Val His Ala Leu Asn Phe Thr Lys Thr Lys Gly Gln Thr Glu
        595                 600                 605

Gln His Asn Glu Ile Leu Arg Ile Leu Leu Leu Arg Thr Ser Asp Lys
    610                 615                 620

Asp Ile Lys Leu Lys Leu Ile Gln Ile Leu Glu Phe Asp Thr Asn Ser
625                 630                 635                 640

Leu Ala Tyr Thr Lys Asn Phe Ile Asn Gln Leu Val Asn Met Ile Lys
                645                 650                 655

Asn Asp Asn Glu Asn Lys Tyr Leu Pro Asp Leu Ala Ser His Ser Asp
            660                 665                 670

Thr Ala Thr Asn Leu His Asp Glu Leu Leu Tyr Ile Ile Asp His Leu
        675                 680                 685

Ser Glu Leu
    690

<210> SEQ ID NO 81
<211> LENGTH: 1578
<212> TYPE: DNA
<213> ORGANISM: Artificial Sequence
<220> FEATURE:
<223> OTHER INFORMATION: SYNTHESIZED

<400> SEQUENCE: 81
atggaccaat tggtgaaaac tgaagtcacc aagaagtctt ttactgctcc tgtacaaaag      60
```

```
gcttctacac cagttttaac caataaaaca gtcatttctg gatcgaaagt caaaagttta      120
tcatctgcgc aatcgagctc atcaggacct tcatcatcta gtgaggaaga tgattcccgc      180
gatattgaaa gcttggataa gaaaatacgt cctttagaag aattagaagc attattaagt      240
agtggaaata caaaacaatt gaagaacaaa gaggtcgctg ccttggttat tcacggtaag      300
ttacctttgt acgctttgga gaaaaaatta ggtgatacta cgagagcggt tgcggtacgt      360
aggaaggctc tttcaatttt ggcagaagct cctgtattag catctgatcg tttaccatat      420
aaaaattatg actacgaccg cgtatttggc gcttgttgtg aaaatgttat aggttacatg      480
cctttgcccg ttggtgttat aggccccttg gttatcgatg gtacatctta tcatatacca      540
atggcaacta cagagggttg tttggtagct tctgccatgc gtggctgtaa ggcaatcaat      600
gctggcggtg gtgcaacaac tgttttaact aaggatggta tgacaagagg cccagtagtc      660
cgtttcccaa ctttgaaaag atctggtgcc tgtaagatat ggttagactc agaagaggga      720
caaaacgcaa ttaaaaaagc ttttaactct acatcaagat ttgcacgtct gcaacatatt      780
caaacttgtc tagcaggaga tttactcttc atgagattta gaacaactac tggtgacgca      840
atgggtatga atatgatttc taaaggtgtc gaatactcat taaagcaaat ggtagaagag      900
tatggctggg aagatatgga ggttgtctcc gtttctggta actactgtac cgacaaaaaa      960
ccagctgcca tcaactggat cgaaggtcgt ggtaagagtg tcgtcgcaga agctactatt     1020
cctggtgatg ttgtcagaaa agtgttaaaa agtgatgttt ccgcattggt tgagttgaac     1080
attgctaaga atttggttgg atctgcaatg gctgggtctg ttggtggatt taacgcacat     1140
gcagctaatt tagtgacagc tgtttttctg gcattaggac aagatcctgc acaaaatgtt     1200
gaaagttcca actgtataac attgatgaaa gaagtggacg tgatttgag aatttccgta     1260 tccatgccat ccatcgaagt aggtaccatc ggtggtggta ctgttctaga accacaaggt     1320
gccatgttgg acttattagg tgtaagaggc ccgcatgcta ccgctcctgg taccaacgca     1380
cgtcaattag caagaatagt tgcctgtgcc gtcttggcag gtgaattatc cttatgtgct     1440
gccctagcag ccggccattt ggttcaaagt catatgaccc acaacaggaa acctgctgaa     1500
ccaacaaaac ctaacaattt ggacgccact gatataaatc gtttgaaaga tgggtccgtc     1560
acctgcatta aatcctaa                                                   1578
```

<210> SEQ ID NO 82
<211> LENGTH: 525
<212> TYPE: PRT
<213> ORGANISM: Artificial Sequence
<220> FEATURE:
<223> OTHER INFORMATION: SYNTHESIZED

<400> SEQUENCE: 82

Met Asp Gln Leu Val Lys Thr Glu Val Thr Lys Lys Ser Phe Thr Ala
1               5                   10                  15

Pro Val Gln Lys Ala Ser Thr Pro Val Leu Thr Asn Lys Thr Val Ile
            20                  25                  30

Ser Gly Ser Lys Val Lys Ser Leu Ser Ala Gln Ser Ser Ser Ser
        35                  40                  45

Gly Pro Ser Ser Ser Glu Glu Asp Asp Ser Arg Asp Ile Glu Ser
    50                  55                  60

Leu Asp Lys Lys Ile Arg Pro Leu Glu Glu Leu Glu Ala Leu Leu Ser
65                  70                  75                  80

Ser Gly Asn Thr Lys Gln Leu Lys Asn Lys Glu Val Ala Ala Leu Val

```
                     85                  90                  95
Ile His Gly Lys Leu Pro Leu Tyr Ala Leu Glu Lys Lys Leu Gly Asp
                100                 105                 110

Thr Thr Arg Ala Val Ala Val Arg Arg Lys Ala Leu Ser Ile Leu Ala
                115                 120                 125

Glu Ala Pro Val Leu Ala Ser Asp Arg Leu Pro Tyr Lys Asn Tyr Asp
                130                 135                 140

Tyr Asp Arg Val Phe Gly Ala Cys Cys Glu Asn Val Ile Gly Tyr Met
145                 150                 155                 160

Pro Leu Pro Val Gly Val Ile Gly Pro Leu Val Ile Asp Gly Thr Ser
                165                 170                 175

Tyr His Ile Pro Met Ala Thr Thr Glu Gly Cys Leu Val Ala Ser Ala
                180                 185                 190

Met Arg Gly Cys Lys Ala Ile Asn Ala Gly Gly Gly Ala Thr Thr Val
                195                 200                 205

Leu Thr Lys Asp Gly Met Thr Arg Gly Pro Val Val Arg Phe Pro Thr
                210                 215                 220

Leu Lys Arg Ser Gly Ala Cys Lys Ile Trp Leu Asp Ser Glu Glu Gly
225                 230                 235                 240

Gln Asn Ala Ile Lys Lys Ala Phe Asn Ser Thr Ser Arg Phe Ala Arg
                245                 250                 255

Leu Gln His Ile Gln Thr Cys Leu Ala Gly Asp Leu Leu Phe Met Arg
                260                 265                 270

Phe Arg Thr Thr Thr Gly Asp Ala Met Gly Met Asn Met Ile Ser Lys
                275                 280                 285

Gly Val Glu Tyr Ser Leu Lys Gln Met Val Glu Glu Tyr Gly Trp Glu
                290                 295                 300

Asp Met Glu Val Val Ser Val Ser Gly Asn Tyr Cys Thr Asp Lys Lys
305                 310                 315                 320

Pro Ala Ala Ile Asn Trp Ile Glu Gly Arg Gly Lys Ser Val Val Ala
                325                 330                 335

Glu Ala Thr Ile Pro Gly Asp Val Val Arg Lys Val Leu Lys Ser Asp
                340                 345                 350

Val Ser Ala Leu Val Glu Leu Asn Ile Ala Lys Asn Leu Val Gly Ser
                355                 360                 365

Ala Met Ala Gly Ser Val Gly Gly Phe Asn Ala His Ala Ala Asn Leu
                370                 375                 380

Val Thr Ala Val Phe Leu Ala Leu Gly Gln Asp Pro Ala Gln Asn Val
385                 390                 395                 400

Glu Ser Ser Asn Cys Ile Thr Leu Met Lys Glu Val Asp Gly Asp Leu
                405                 410                 415

Arg Ile Ser Val Ser Met Pro Ser Ile Glu Val Gly Thr Ile Gly Gly
                420                 425                 430

Gly Thr Val Leu Glu Pro Gln Gly Ala Met Leu Asp Leu Leu Gly Val
                435                 440                 445

Arg Gly Pro His Ala Thr Ala Pro Gly Thr Asn Ala Arg Gln Leu Ala
                450                 455                 460

Arg Ile Val Ala Cys Ala Val Leu Ala Gly Glu Leu Ser Leu Cys Ala
465                 470                 475                 480

Ala Leu Ala Ala Gly His Leu Val Gln Ser His Met Thr His Asn Arg
                485                 490                 495

Lys Pro Ala Glu Pro Thr Lys Pro Asn Asn Leu Asp Ala Thr Asp Ile
                500                 505                 510
```

Asn Arg Leu Lys Asp Gly Ser Val Thr Cys Ile Lys Ser
        515                 520                 525

<210> SEQ ID NO 83
<211> LENGTH: 1602
<212> TYPE: DNA
<213> ORGANISM: Lactuca sativa

<400> SEQUENCE: 83

```
atggagtgct ttggagctcg aaacatgacg gcaacaatgg cggtttttac gtgccctaga      60
ttcacggact gtaatatcag gcacaaattt tcgttactga acaacgaag atttactaat     120
ttatcagcat cgtcttcgtt gcgtcaaatt aagtgcagcg ctaaaagcga ccgttgtgta    180
gtggataaac aagggatttc cgtagcagac gaagaagatt atgtgaaggc cggtggatcg    240
gagctgtttt ttgttcaaat gcagcggact aagtccatga aaagccagtc taaactttcc    300
gaaaagctag cacagatacc aattggaaat tgcatacttg atctggttgt aatcggttgt    360
ggccctgctg gccttgctct tgctgcagag tcagccaaac tagggttgaa cgttggactc    420
attggccctg atcttccttt tacaaacaat tatggtgttt ggcaggatga atttataggt    480
cttgacttga aggatgcat tgaacattct tggaaagata ctcttgtata ccttgatgat    540
gctgatccca tccgcatagg tcgtgcatat ggcagagttc atcgtgattt acttcatgaa    600
gagttgttaa aaggtgtgt ggaatcaggt gtttcatatc taagctccaa agtagaaaga    660
atcactgaag ctccaaatgg ctatagtctc attgaatgtg aaggcaatat caccattcca    720
tgcaggcttg ctactgttgc atcaggggca gcttcaggga aatttctgga gtatgaactt    780
gggggtcccc gtgtttgtgt ccaaacagct tatggtatag aggttgaggt tgaaaacaac    840
ccctatgatc cagatctaat ggtgttcatg gattatagac cttctcaaa acataaaccg    900
gaatctttag aagcaaaata tccgactttc ctctatgtca tggccatgtc tccaacaaaa    960
atattcttcg aggaaacttg tttagcttca agagaagcca tgccttttcaa tcttctaaag   1020
tccaaactca tgtcacgatt aaaggcaatg ggtatccgaa taacaagaac gtacgaagag   1080
gaatggtcgt atatccccgt aggtggatcg ttacctaata cagaacaaaa gaatctcgca   1140
tttggtgctg cagctagtat ggtgcaccct gccacagggt attcagttgt tcgatctttg   1200
tcagaagctc ctaattatgc agcagtcatt gctaagattt taagacaaga tcaatctaaa   1260
gagatgattt ctcttggaaa atacactaac atttcaaaac aagcatggga aacattgtgg   1320
ccacttgaaa ggaaaagaca gcgagccttc tttctattcg gactatcaca catcgtgcta   1380
atggatctag agggaacacg tacatttttc cgtactttct ttcgtttgcc caaatggatg   1440
tggtggggat ttttgggtc ttctttatct tcaacggatt tgataatatt tgcgctttat   1500
atgtttgtga tagcacctca cagcttgaga atggaactgg ttagacatct actttctgat   1560
ccgacagggg caactatggt aaaagcatat ctcactatat ag                       1602
```

<210> SEQ ID NO 84
<211> LENGTH: 1602
<212> TYPE: DNA
<213> ORGANISM: Artificial Sequence
<220> FEATURE:
<223> OTHER INFORMATION: SYNTHESIZED

<400> SEQUENCE: 84

```
atggagtgct ttggagcccg aaacatgact gctactatgg ccgttttac ctgcccccga      60
ttcaccgact gcaacatccg acacaagttc tctctgctca agcagcgacg attcaccaac    120
```

```
ctgtccgctt cctcttcgct ccgacagatc aagtgctctg ccaagtcgga ccgatgtgtc      180
gtggataagc agggtatttc tgtcgctgac gaggaggatt acgtgaaggc cggcggttcc      240
gagctgttct tgtgcagat gcagcgaacc aagtccatgg agtcccagtc taagctgtct       300
gagaagctcg ctcagatccc cattggaaac tgcatcctgg acctcgttgt cattggatgt      360
ggtcctgctg gactggctct cgctgctgag tctgctaagc tgggcctcaa cgtgggtctg      420
atcggacccg acctcccttt caccaacaac tacgagtttt ggcaggatga gtttatcgga      480
ctgggcctcg agggctgcat tgagcactcc tggaaggaca ctctggtcta cctcgacgat      540
gctgatccca tccgaattgg acgagcctac ggccgagtgc accgagacct gctccatgag      600
gagctgctcc gacgatgtgt ggagtccggc gtttcttacc tgtcctctaa ggtggagcga      660
atcaccgagg cccccaacgg ctactctctg attgagtgcg agggtaacat caccattcct      720
tgccgactgg ctactgtcgc ttcgggtgct gcttccggaa agttcctgga gtacgagctc      780
ggaggacccc gagtctgcgt gcagaccgct acggtatcg aggttgaggt cgagaacaac      840
ccctacgacc ctgatctgat ggttttcatg gactaccgag attttccgaa gcacaagccc      900
gagtccctgg aggctaagta ccctaccttc tctctacgtca tggccatgtc tcccaccaag     960 atttttcttcg aggagacttg tctggcttcc cgagaggcca tgcctttcaa cctgctcaag    1020
tctaagctga tgtcgcgact caaggccatg ggaatccgaa ttcccgaac ttacgaggag      1080 gagtggtctt acattcccgt tggtggatcg ctgcctaaca ccgagcagaa gaacctcgct    1140
ttcggtgccg ctgcctcgat ggtccatcct gccactggat actccgtggt tcgatcgctg    1200
tccgaggctc ctaactacgc tgccgtgatc gccaagattc tgcgacagga ccagtccaag    1260
gagatgatct ctctcggcaa gtacaccaac atttctaagc aggcttggga gactctgtgg    1320
cccctcgagc gaaagcgaca gcgagccttc tttctgttcg gcctctccca catcgtcctg    1380
atggacctcg agggtacccg aactttcttt cgaaccttct ttcgactgcc caagtggatg    1440
tggtggggct tcctgggttc gtccctctct tcgactgacc tgatcatttt cgctctctac    1500
atgtttgtta ttgcccctca ttccctgcga atggagctcg tccgacatct gctctccgac    1560
cctactggtg ctactatggt gaaggcttac ctgactatct aa                        1602

<210> SEQ ID NO 85
<211> LENGTH: 1602
<212> TYPE: DNA
<213> ORGANISM: Artificial Sequence
<220> FEATURE:
<223> OTHER INFORMATION: SYNTHESIZED

<400> SEQUENCE: 85
atggagtgct cggcgctag aaatatgact gccacaatgg cggttttttac gtgccccagg      60 ttcacagact gtaacattcg tcacaagttt agccttctga acaaagaag gttcactaat      120 ttgtctgcaa gcagttcact aaggcaaata aagtgttcag ctaaatctga ccgttgcgtt     180
gttgacaagc aaggtatttc cgttgcagac gaggaagact acgtcaaggc gggtggctcc    240
gagttatttt tgttcagat gcagagaaca aaaagcatgg aaagccagtc aaagcttagt    300
gagaaattag cacagatacc tatcgggaat tgtatcttgg atttagtggt cataggatgt    360
ggcccggcgg gcttgcgct tgccgccgag tccgcgaaac tgggccttaa cgtaggccta    420
ataggcccgg acttgccttt cactaacaac tatggggtat ggcaggacga atttatcggc    480
ctgggcttgg aggggtgtat agaacacagt tggaaggaca cgcttgttta cttggacgat    540
```

```
gctgatccga tccgtatagg tcgtgcttac ggtagggtgc accgtgacct actgcacgag    600
gagctactaa gacgttgtgt tgagagcggg gtgtcatatt tatcctcaaa ggtcgaaagg    660
attaccgaag cgcctaacgg gtactctctt atagaatgtg aaggaaacat cacgatccct    720
tgtaggcttg caacggtggc gtccggagca gcttctggca agttttttaga atacgagtta   780 ggaggaccga gagtttgcgt tcaaacggcg tatgggatag aggtggaggt ggagaataac    840
ccgtatgatc cggacctaat ggtattcatg gattatagag acttttctaa gcacaaaccg    900
gagagtcttg aagcgaaata cccgaccttc ttatacgtaa tggcaatgag cccaaccaag    960
atattctttg aggagacttg cctggcgagc agagaagcga tgccatttaa cctgctgaaa   1020
agcaagttga tgagcaggct aaagctatg ggtataagaa taacaagaac ctacgaggag    1080
gaatggagct acattccggt gggagggtca ttaccgaata ctgagcagaa aaacctggct   1140
ttcggcgcgg cggcgagtat ggttcacccg gccacgggat attctgtcgt aaggtctttg   1200
agcgaagcac cgaactatgc agcggtgatc gccaagattt taagacagga ccaaagtaag   1260
gaaatgatca gcctgggcaa gtacgcgaat attagcaagc aggcatggga aactttatgg   1320
cctctagaaa gaaaacgtca gagagctttt ttccttttcg gcctttcaca catagtgttg   1380
atggatttgg aaggcacgag aacatttttc aggaccttct ttagattgcc aaagtggatg   1440 tggtggggt tcctgggatc ttctttgtct agtacggatt taatcatctt gcgctatac    1500 atgtttgtga ttgccccgca ctccctaagg atggagctgg tgagacatct attaagtgat   1560
cccacgggtg cgactatggt caaggcatat cttactattt ag                      1602
```

```
<210> SEQ ID NO 86
<211> LENGTH: 1602
<212> TYPE: DNA
<213> ORGANISM: Artificial Sequence
<220> FEATURE:
<223> OTHER INFORMATION: SYNTHESIZED

<400> SEQUENCE: 86
```

```
atggagtgtt ttggcgctcg taatatgacc gcgacaatgg ccgtcttcac ttgtccgcgc     60
tttactgatt gtaacattcg tcacaaattt agtttgctga gcaacgtcg tttcactaac     120 ttgagtgctt cctcgtcgct gcgccaaatc aagtgttctg ccaagtcaga ccgctgtgtc    180
gttgacaaac agggtattag tgtagctgat gaagaggatt acgtcaaagc aggcggaagc    240
gaattatttt tcgttcaaat gcaacgtacc aagtcaatgg agagccaaag taagttatct    300
gagaaattgg cacagatccc aattgggaac tgtatcttag acttagtggt aattgggtgt    360
ggacccgctg gactggctct tgcggcagag tccgcgaagc ttggtctgaa tgtcggtttg    420
attggacccg acttaccttt caccaataat tacggtgtct ggcaggacga attcattgga    480
cttggattag aaggttgtat cgagcattcg tggaaagaca cgttagtata tttagatgac    540
gctgacccta tccgtatcgg tcgtgcatac ggacgtgtgc accgtgactt attgcatgag    600
gaattattgc gccgctgtgt tgaatctggc gtcagctact tatccagcaa agttgaacgt    660
attacagaag caccaaatgg ctattccttg atcgaatgcg aaggaaacat tacaattcct    720
tgccgcctgg caaccgtcgc ttccggagcc gcatccggaa aattcttaga atatgagctt    780
ggtgggcctc gcgtttgcgt ccaaacagcc tacggcattg aggtcgaagt agaaaataat    840
ccctatgacc ctgacttgat ggtgttcatg gattatcgtg acttctcaaa gcataaacca    900
gagagcctga agcaaaaata cccaactttc ttgtacgtta tggctatgag ccccaccaag    960
atcttctttg aggaaacatg cttagctagc cgcgaggcca tgcccttcaa cttgcttaag   1020
```

```
tccaaattaa tgtcacgctt gaaggcaatg ggtatccgta ttacccgcac ctatgaggag      1080
gaatggtcct acattcccgt tggtggctcg ctgccaaata cggagcagaa aaacttagct      1140
tttggtgctg cggcttcgat ggtgcaccca gcaacagggt atagtgtcgt tcgtagtttg      1200
tccgaagctc ctaattacgc ggccgttatc gcgaaaattc ttcgtcaaga tcaatctaaa      1260
gagatgatca gtttgggcaa gtacacaaac atttcaaaac aagcgtggga cgttgtggg      1320 ccgttagagc gcaaacgtca acgtgcattc tttttgttcg gtttgagtca cattgtctta      1380
atggatttgg aaggaactcg tactttcttc cgcacctttt tccgcttacc aaaatggatg      1440
tggtggggct tcctgggatc atcccttagt tcgacggacc tgattatctt cgcattgtac      1500
atgtttgtta tcgctccgca ctcattacgc atggaactgg tccgtcattt attgtccgat      1560
ccgactggag cgactatggt taaggcatat ttgaccatct ag                         1602
```

<210> SEQ ID NO 87
<211> LENGTH: 533
<212> TYPE: PRT
<213> ORGANISM: Lactuca sativa

<400> SEQUENCE: 87

```
Met Glu Cys Phe Gly Ala Arg Asn Met Thr Ala Thr Met Ala Val Phe
1               5                   10                  15

Thr Cys Pro Arg Phe Thr Asp Cys Asn Ile Arg His Lys Phe Ser Leu
            20                  25                  30

Leu Lys Gln Arg Arg Phe Thr Asn Leu Ser Ala Ser Ser Ser Leu Arg
        35                  40                  45

Gln Ile Lys Cys Ser Ala Lys Ser Asp Arg Cys Val Val Asp Lys Gln
    50                  55                  60

Gly Ile Ser Val Ala Asp Glu Asp Tyr Val Lys Ala Gly Gly Ser
65                  70                  75                  80

Glu Leu Phe Phe Val Gln Met Gln Arg Thr Lys Ser Met Glu Ser Gln
                85                  90                  95

Ser Lys Leu Ser Glu Lys Leu Ala Gln Ile Pro Ile Gly Asn Cys Ile
            100                 105                 110

Leu Asp Leu Val Val Ile Gly Cys Gly Pro Ala Gly Leu Ala Leu Ala
        115                 120                 125

Ala Glu Ser Ala Lys Leu Gly Leu Asn Val Gly Leu Ile Gly Pro Asp
    130                 135                 140

Leu Pro Phe Thr Asn Asn Tyr Gly Val Trp Gln Asp Glu Phe Ile Gly
145                 150                 155                 160

Leu Gly Leu Glu Gly Cys Ile Glu His Ser Trp Lys Asp Thr Leu Val
                165                 170                 175

Tyr Leu Asp Asp Ala Asp Pro Ile Arg Ile Gly Arg Ala Tyr Gly Arg
            180                 185                 190

Val His Arg Asp Leu Leu His Glu Glu Leu Leu Arg Arg Cys Val Glu
        195                 200                 205

Ser Gly Val Ser Tyr Leu Ser Ser Lys Val Glu Arg Ile Thr Glu Ala
    210                 215                 220

Pro Asn Gly Tyr Ser Leu Ile Cys Glu Gly Asn Ile Thr Ile Pro
225                 230                 235                 240

Cys Arg Leu Ala Thr Val Ala Ser Gly Ala Ala Ser Gly Lys Phe Leu
                245                 250                 255

Glu Tyr Glu Leu Gly Gly Pro Arg Val Cys Val Gln Thr Ala Tyr Gly
            260                 265                 270
```

```
Ile Glu Val Glu Val Glu Asn Asn Pro Tyr Asp Pro Asp Leu Met Val
            275                 280                 285

Phe Met Asp Tyr Arg Asp Phe Ser Lys His Lys Pro Glu Ser Leu Glu
        290                 295                 300

Ala Lys Tyr Pro Thr Phe Leu Tyr Val Met Ala Met Ser Pro Thr Lys
305                 310                 315                 320

Ile Phe Phe Glu Glu Thr Cys Leu Ala Ser Arg Glu Ala Met Pro Phe
                325                 330                 335

Asn Leu Leu Lys Ser Lys Leu Met Ser Arg Leu Lys Ala Met Gly Ile
            340                 345                 350

Arg Ile Thr Arg Thr Tyr Glu Glu Trp Ser Tyr Ile Pro Val Gly
            355                 360                 365

Gly Ser Leu Pro Asn Thr Glu Gln Lys Asn Leu Ala Phe Gly Ala Ala
        370                 375                 380

Ala Ser Met Val His Pro Ala Thr Gly Tyr Ser Val Val Arg Ser Leu
385                 390                 395                 400

Ser Glu Ala Pro Asn Tyr Ala Ala Val Ile Ala Lys Ile Leu Arg Gln
                405                 410                 415

Asp Gln Ser Lys Glu Met Ile Ser Leu Gly Lys Tyr Thr Asn Ile Ser
            420                 425                 430

Lys Gln Ala Trp Glu Thr Leu Trp Pro Leu Glu Arg Lys Arg Gln Arg
        435                 440                 445

Ala Phe Phe Leu Phe Gly Leu Ser His Ile Val Leu Met Asp Leu Glu
450                 455                 460

Gly Thr Arg Thr Phe Phe Arg Thr Phe Phe Arg Leu Pro Lys Trp Met
465                 470                 475                 480

Trp Trp Gly Phe Leu Gly Ser Ser Leu Ser Ser Thr Asp Leu Ile Ile
                485                 490                 495

Phe Ala Leu Tyr Met Phe Val Ile Ala Pro His Ser Leu Arg Met Glu
            500                 505                 510

Leu Val Arg His Leu Leu Ser Asp Pro Thr Gly Ala Thr Met Val Lys
        515                 520                 525

Ala Tyr Leu Thr Ile
        530

<210> SEQ ID NO 88
<211> LENGTH: 1644
<212> TYPE: DNA
<213> ORGANISM: Daucus carota

<400> SEQUENCE: 88 atggggtga cagagcacga gaaaagcgaa caagtggaga gaatcaaaga tgttgtgatt      60
gttaatccca agccaagcaa aggattgacg tccaaggcta ttgattggat tgagagcttg    120
attgtcaagt tgatgtatga cgcttctgtg cctcatcatt ggctggctgg gaactttgcg    180
cctgtggatg agacgcctcc tgctcgtgat cttccagtta ttggttctat tccggagtgt    240
ctgaatggtg agtttgtcag ggttggtcca aatccaaaat tctcccctgt tgctggctat    300
cactggtttg atgagatgg catgattcat ggattacgca tcaaagatgg gaaagctacc    360
tatgtctccc gctatgtgag acatctcgt ctaaagcaag aagagacttt tggtggagct    420
aagttcatga agattggaga tctcaaggga ctatttggat tacttatggt caatatgcaa    480
atgctcagag gaaagttgaa tgtactagat atgtcatatg gaatggaac agctaacact    540 gccatgatat atcatcatgg aagactcttg gctctttcag aagccgataa accatatgcc    600
```

```
attaaagtgt tggaagatgg agatctacaa actcttggat tgttggatta tgacaaaagg    660
ctgacacatt ctttcactgc ccatccaaag gtcgacccat ttaccggtga aatgtttacc    720
tttggctatt cacacacacc tccatatata acatacagag tgatttccaa ggatggtgtt    780
atgaatgatc cagtgccaat aacattagca gaccctataa tgatgcacga ctttgccatc    840
actgaaaatt atgcaattat aatggacctg ccgttatact ttaaacccaa ggaaatggtc    900
aaggaaaaga agctgatttt cacatttgat gcaactaaaa aggcccgttt tggtgtcctt    960
ccacgatatg caaagaatga gctgctgatt aaatggtttg agctcccaaa ttgctttata   1020
tttcacaatg ccaacgcttg ggaagaagga gacgaagttg ttctgatcac ttgccgcctt   1080
gagaatccag acttagatat ggttaatggg agtatgaaag agaagctcga gaatttcaac   1140
aatgaactgt atgagatgag attcaacatg aagagtggtc tagcttcaca gaaaaagctc   1200
tcagcatctg ctgttgattt tcctaggata aatgagagct atactgggag gaaacaacgt   1260
tatgtttatg ccacttcact ggacagcatt gcgaaggtca ctgggattgt caaattcgat   1320
ttgcacatgg aaccagagat cgggaaaaag aagctggaag ttggaggaaa catacaaggt   1380
atctttgatc ttggagttgg tagatttggt tcagaggcca tttttgtacc tcgccagcca   1440
ggcactacat ctgaagaaga tgatggctac ttgattcatt ttttacatga tgagagcacc   1500
ggaaaatctg ctgcaaatat aattgatgca aaaacaatgt cacctgatcc tgttgcagtt   1560
gttgaattac cacacagagt tccgtatggg ttccatgcct tttttgtgac tgaggaacaa   1620
cttcaagaac aagccaaact gtag                                          1644

<210> SEQ ID NO 89
<211> LENGTH: 1644
<212> TYPE: DNA
<213> ORGANISM: Artificial Sequence
<220> FEATURE:
<223> OTHER INFORMATION: SYNTHESIZED

<400> SEQUENCE: 89
atgggagtta ccgagcacga gaagtccgag caggtggagc gaatcaagga tgtggtcatt     60
gtgaacccca gccctctaa gggtctgacc tctaaggcca tcgactggat tgagtcgctg    120
atcgtcaagc tcatgtacga tgcttccgtg ccccaccatt ggctggccgg aaacttcgct    180
cctgtggacg agacccctcc tgcccgagac ctgcccgtta tcggctctat tcctgagtgc    240
ctgaacggcg agttcgtgcg agttggtccc aaccctaagt tttcgcctgt ggctggctac    300
cactggttcg acggcgacgg aatgatccat ggactgcgaa ttaaggacgg caaggctacc    360
tacgtctcgc gatacgtgcg aacttcccga ctcaagcagg aggagacctt cggcggtgcc    420
aagtttatga agattggtga cctgaagggt ctcttcggac tgctcatggt caacatgcag    480
atgctgcgag gaaagctgaa cgtgctcgac atgtcctacg caacggcac cgccaacact    540
gctatgatct accaccatgg ccgactgctc gccctctctg aggctgacaa gccctacgct    600
attaaggtcc tggaggacgg cgacctgcag accctcggac tgctcgacta cgataagcga    660
ctgacccact cttttactgc ccatcccaag gtggacccct tcaccggcga gatgttcact    720
tttggttact cccacacccc cccttacatc acttaccgag tcatttctaa ggacggcgtg    780
atgaacgatc ccgttcctat cactctggct gaccccatta tgatgcacga ttttgccatc    840
accgagaact acgctatcat tatggacctg ccctctact tcaagcctaa ggagatggtg    900
aaggagaaga agctcatttt cacctttgat gccactaaga aggctcgatt tggtgttctg    960
```

```
ccccgatacg ccaagaacga gctgctcatc aagtggttcg agctccctaa ctgcttcatt    1020
tttcacaacg ccaacgcttg ggaggagggc gacgaggtcg tgctgatcac ctgccgactg    1080
gagaaccccg acctggatat ggtgaacggt tccatgaagg agaagctgga gactttaac     1140 aacgagctgt acgagatgcg attcaacatg aagtctggac tcgcctcgca gaagaagctg    1200
tccgcctctg ctgttgactt cccccgaatc aacgagtctt acaccggccg aaagcagcga    1260
tacgtctacg ccacttcgct ggactccatc gctaaggtta ccggcattgt caagtttgat    1320
ctccacatgg agcctgagat tggcaagaag aagctggagg tcggaggcaa catccagggt    1380
attttcgacc tcggagttgg ccgattcgga tcggaggcca tctttgtccc ccgacagcct    1440
ggaaccactt ccgaggagga cgatggctac ctgattcact tcctccatga cgagtccact    1500
ggcaagtctg ccgctaacat cattgacgcc aagaccatgt cccccgatcc tgttgctgtt    1560
gtcgagctgc cccaccgagt cccttacgga ttccatgcct tctttgtgac cgaggagcag    1620
ctccaggagc aggctaagct gtaa                                           1644
```

<210> SEQ ID NO 90
<211> LENGTH: 1644
<212> TYPE: DNA
<213> ORGANISM: Artificial Sequence
<220> FEATURE:
<223> OTHER INFORMATION: SYNTHESIZED

<400> SEQUENCE: 90

```
atgggcgtta cagaacatga gaaaagcgaa caagtcgagc gtataaaaga tgttgttatt      60
gtcaatccca aacccagtaa gggtctaacg agtaaagcta ttgactggat tgagagctta    120
attgtaaagt taatgtatga cgcaagtgtg ccacaccact ggttagcagg gaatttcgcc    180
cccgtggaca aaaccccgcc agccagagat ttgcccgtta tcggttccat acctgagtgc    240
ttgaatggag agttcgtgcg tgtttgggcct aacccaaagt ttagtccagt tgccggctat    300
cactggtttg acgggacggg catgattcac ggcttaagaa ttaaggatgg caaagcaacg    360
tatgttagtc gttatgtgag gacgtctcgt ctaaagcagg aagagacatt tggggggggct    420 aaattcatga aaataggaga ccttaagggc ctttttggtc tgttaatggt taatatgcag    480
atgctgcgtg gaaaacttaa cgtgcttgat atgagttatg gaaacggaac tgcaaatacg    540
gcgatgattt accatcatgg ccgtttgcta gctcttccg aggctgataa acccctatgcg    600 atcaaagtgt tagaagacgg ggacttacag acgctgggtt tactggatta cgataaacgt    660
ttgacccact cttttacagc tcatcctaaa gtggacccat ttactgggga tgtgttact     720 ttcggttact ctcacactcc cccatacatc acgtatagg tcatctcaaa agacggtgtt    780
atgaatgatc cagttcctat caccttagcg gatcccatta tgatgcacga tttcgcaatt    840
acggaaaatt acgcaatcat tatggaactg ccctgtact tcaagcaaa ggagatggta     900 aaagagaaga aactgatttt cacatttgac gctaccaaga aggcaaggtt tggcgtattg    960
ccaagatatg caaaaaatga gttactaatt aaatggtttg agctgccaaa ttgttttcata    1020 ttccacaacg cgaacgcgtg ggaagaggg gatgaagttg tgttaattac ctgtcgtctt    1080
gaaaacccag acctagacat ggtgaacgga tccatgaaag aaaaactaga aatttcaat    1140 aacgagcttt acgaaatgag gttcaatatg aaagcggcc tggcttctca gaagaaattg    1200
agtgcctctg cagtcgattt cccgaggatc aacgagtcct atactggacg taaacagagg    1260
tatgtatatg ctacgagtct ggatagcatt gcgaaggta cgggcatcgt aaaatttgac    1320
ttacacatgg agccagagat tggaaagaag aaattggaag ttgggggtaa tatccaaggg    1380
```

| | |
|---|---|
| atattcgact taggggttgg gcgtttcggt agtgaggcaa tctttgtacc ccgtcaacca | 1440 |
| ggaaccacct cagaagagga cgacgggtac ctgatccatt ttctacatga cgagagtact | 1500 |
| gggaaaagcg cagcgaacat cattgacgca aaaacaatgt ctcctgaccc tgtagcagtt | 1560 |
| gtcgaattgc cgcatcgtgt cccatatggc ttccatgctt tttttgtgac ggaagaacaa | 1620 |
| ctgcaggagc aagctaaatt gtag | 1644 |

<210> SEQ ID NO 91
<211> LENGTH: 1644
<212> TYPE: DNA
<213> ORGANISM: Artificial Sequence
<220> FEATURE:
<223> OTHER INFORMATION: SYNTHESIZED

<400> SEQUENCE: 91

| | |
|---|---|
| atgggagtca cggagcacga gaagtccgag caagtagaac gcatcaaaga cgtcgtaatc | 60 |
| gtgaatccca aaccttcgaa gggtttgaca agtaaagcta tcgattggat cgaaagtttg | 120 |
| atcgtgaaat tgatgtacga tgcttcggtc ccgcaccatt ggctggccgg aaatttcgcc | 180 |
| cccgtcgaca aacccccccc cgctcgcgac ttaccggtga ttggctccat tccggaatgt | 240 |
| cttaatggcg agttcgtccg tgtaggtcca aatccgaaat ttagtcccgt ggcgggatac | 300 |
| cattggttcg acggtgatgg gatgattcat ggcttacgta ttaaggatgg taaggccacg | 360 |
| tatgtatcac gttacgtgcg tacaagtcgc ttgaaacaag aagagacgtt tggaggagca | 420 |
| aagtttatga aaattggcga cctgaagggt ttatttggac tgttgatggt gaacatgcag | 480 |
| atgcttcgcg ggaaacttaa tgttcttgat atgtcctatg ggaacgggac ggccaacaca | 540 |
| gcaatgattt tcaccatgg acgcttgtta gcgctttccg aggcggataa gccctacgca | 600 |
| attaaagtgt tagaagatgg ggaccttcaa acacttgggc ttttagacta cgataagcgc | 660 |
| ctgacgcact catttaccgc gcacccaaaa gtagatccat tcacgggtga atgttcacg | 720 |
| ttcgggtatt ctcacacgcc gccgtatatt acgtaccgtg tcatttccaa agacggcgtt | 780 |
| atgaacgatc cagtacctat tacgttagcg gacccaatca tgatgcatga ctttgcaatc | 840 |
| accgagaact atgctattat tatggatttg cccttgtact ttaagccgaa ggagatggtg | 900 |
| aaagagaaga aattgatctt tacgtttgat gctacgaaaa aagcgcgttt cggagtcttg | 960 |
| ccgcgctatg ctaaaaacga gctgttgatt aagtggttcg aattgcctaa ctgcttcatt | 1020 |
| tttcacaatg ctaatgcatg gaagaaggt gatgaggtgg ttctgatcac ctgccgtttg | 1080 |
| gaaaacccag acttagacat ggtcaatggg agtatgaagg agaaactgga gactttaat | 1140 |
| aatgaacttt atgagatgcg tttcaacatg aaaagcggat tagcgagcca gaagaagttg | 1200 |
| agcgcatcag ccgtagattt tcctcgcatc aacgagtcct acacaggacg caaacagcgc | 1260 |
| tatgtatatg cgactagttt ggactctatt gctaaggtaa ctggaattgt aaaattcgac | 1320 |
| cttcatatgg aaccagaaat tgggaaaaaa agcttgaggt tggaggtaa cattcaaggt | 1380 |
| atcttcgact tgggggttgg gcgctttggg agtgaggcaa ttttttgtccc tcgccaaccg | 1440 |
| ggtacaacct cggaagaaga tgatggctat ttgatccatt ttctgcatga cgagtcaacg | 1500 |
| ggaaagtcag cagctaacat tattgacgct aagaccatgt cccccgaccc tgtcgccgta | 1560 |
| gtagaactgc cgcatcgtgt tccttatggc tttcacgcat tttttgttac ggaagaacag | 1620 |
| cttcaggagc aggcaaaact ttag | 1644 |

<210> SEQ ID NO 92

```
<211> LENGTH: 547
<212> TYPE: PRT
<213> ORGANISM: Daucus carota

<400> SEQUENCE: 92
```

| | | | | | | | | | | | | | | | |
|---|---|---|---|---|---|---|---|---|---|---|---|---|---|---|---|
| Met | Gly | Val | Thr | Glu | His | Glu | Lys | Ser | Glu | Gln | Val | Glu | Arg | Ile | Lys |
| 1 | | | | 5 | | | | | 10 | | | | | 15 | |
| Asp | Val | Val | Ile | Val | Asn | Pro | Lys | Pro | Ser | Lys | Gly | Leu | Thr | Ser | Lys |
| | | | 20 | | | | | 25 | | | | | 30 | | |
| Ala | Ile | Asp | Trp | Ile | Glu | Ser | Leu | Ile | Val | Lys | Leu | Met | Tyr | Asp | Ala |
| | | 35 | | | | | 40 | | | | | 45 | | | |
| Ser | Val | Pro | His | His | Trp | Leu | Ala | Gly | Asn | Phe | Ala | Pro | Val | Asp | Glu |
| | 50 | | | | | 55 | | | | | 60 | | | | |
| Thr | Pro | Pro | Ala | Arg | Asp | Leu | Pro | Val | Ile | Gly | Ser | Ile | Pro | Glu | Cys |
| 65 | | | | | 70 | | | | | 75 | | | | | 80 |
| Leu | Asn | Gly | Glu | Phe | Val | Arg | Val | Gly | Pro | Asn | Pro | Lys | Phe | Ser | Pro |
| | | | | 85 | | | | | 90 | | | | | 95 | |
| Val | Ala | Gly | Tyr | His | Trp | Phe | Asp | Gly | Asp | Gly | Met | Ile | His | Gly | Leu |
| | | | 100 | | | | | 105 | | | | | 110 | | |
| Arg | Ile | Lys | Asp | Gly | Lys | Ala | Thr | Tyr | Val | Ser | Arg | Tyr | Val | Arg | Thr |
| | | 115 | | | | | 120 | | | | | 125 | | | |
| Ser | Arg | Leu | Lys | Gln | Glu | Thr | Phe | Gly | Gly | Ala | Lys | Phe | Met | Lys | |
| | 130 | | | | | 135 | | | | | 140 | | | | |
| Ile | Gly | Asp | Leu | Lys | Gly | Leu | Phe | Gly | Leu | Leu | Met | Val | Asn | Met | Gln |
| 145 | | | | | 150 | | | | | 155 | | | | | 160 |
| Met | Leu | Arg | Gly | Lys | Leu | Asn | Val | Leu | Asp | Met | Ser | Tyr | Gly | Asn | Gly |
| | | | | 165 | | | | | 170 | | | | | 175 | |
| Thr | Ala | Asn | Thr | Ala | Met | Ile | Tyr | His | His | Gly | Arg | Leu | Leu | Ala | Leu |
| | | | 180 | | | | | 185 | | | | | 190 | | |
| Ser | Glu | Ala | Asp | Lys | Pro | Tyr | Ala | Ile | Lys | Val | Leu | Glu | Asp | Gly | Asp |
| | | 195 | | | | | 200 | | | | | 205 | | | |
| Leu | Gln | Thr | Leu | Gly | Leu | Leu | Asp | Tyr | Asp | Lys | Arg | Leu | Thr | His | Ser |
| | 210 | | | | | 215 | | | | | 220 | | | | |
| Phe | Thr | Ala | His | Pro | Lys | Val | Asp | Pro | Phe | Thr | Gly | Glu | Met | Phe | Thr |
| 225 | | | | | 230 | | | | | 235 | | | | | 240 |
| Phe | Gly | Tyr | Ser | His | Thr | Pro | Pro | Tyr | Ile | Thr | Tyr | Arg | Val | Ile | Ser |
| | | | | 245 | | | | | 250 | | | | | 255 | |
| Lys | Asp | Gly | Val | Met | Asn | Asp | Pro | Val | Pro | Ile | Thr | Leu | Ala | Asp | Pro |
| | | | 260 | | | | | 265 | | | | | 270 | | |
| Ile | Met | Met | His | Asp | Phe | Ala | Ile | Thr | Glu | Asn | Tyr | Ala | Ile | Ile | Met |
| | | 275 | | | | | 280 | | | | | 285 | | | |
| Asp | Leu | Pro | Leu | Tyr | Phe | Lys | Pro | Lys | Glu | Met | Val | Lys | Glu | Lys | Lys |
| | 290 | | | | | 295 | | | | | 300 | | | | |
| Leu | Ile | Phe | Thr | Phe | Asp | Ala | Thr | Lys | Lys | Ala | Arg | Phe | Gly | Val | Leu |
| 305 | | | | | 310 | | | | | 315 | | | | | 320 |
| Pro | Arg | Tyr | Ala | Lys | Asn | Glu | Leu | Leu | Ile | Lys | Trp | Phe | Glu | Leu | Pro |
| | | | | 325 | | | | | 330 | | | | | 335 | |
| Asn | Cys | Phe | Ile | Phe | His | Asn | Ala | Asn | Ala | Trp | Glu | Glu | Gly | Asp | Glu |
| | | | 340 | | | | | 345 | | | | | 350 | | |
| Val | Val | Leu | Ile | Thr | Cys | Arg | Leu | Glu | Asn | Pro | Asp | Leu | Asp | Met | Val |
| | | 355 | | | | | 360 | | | | | 365 | | | |
| Asn | Gly | Ser | Met | Lys | Glu | Lys | Leu | Glu | Asn | Phe | Asn | Asn | Glu | Leu | Tyr |
| | 370 | | | | | 375 | | | | | 380 | | | | |
| Glu | Met | Arg | Phe | Asn | Met | Lys | Ser | Gly | Leu | Ala | Ser | Gln | Lys | Lys | Leu |

-continued

```
385              390              395              400
Ser Ala Ser Ala Val Asp Phe Pro Arg Ile Asn Glu Ser Tyr Thr Gly
            405              410              415

Arg Lys Gln Arg Tyr Val Tyr Ala Thr Ser Leu Asp Ser Ile Ala Lys
            420              425              430

Val Thr Gly Ile Val Lys Phe Asp Leu His Met Glu Pro Glu Ile Gly
            435              440              445

Lys Lys Lys Leu Glu Val Gly Gly Asn Ile Gln Gly Ile Phe Asp Leu
    450              455              460

Gly Val Gly Arg Phe Gly Ser Glu Ala Ile Phe Val Pro Arg Gln Pro
465              470              475              480

Gly Thr Thr Ser Glu Glu Asp Asp Gly Tyr Leu Ile His Phe Leu His
            485              490              495

Asp Glu Ser Thr Gly Lys Ser Ala Ala Asn Ile Ile Asp Ala Lys Thr
            500              505              510

Met Ser Pro Asp Pro Val Ala Val Val Glu Leu Pro His Arg Val Pro
            515              520              525

Tyr Gly Phe His Ala Phe Phe Val Thr Glu Glu Gln Leu Gln Glu Gln
    530              535              540

Ala Lys Leu
545
```

COMPOSITIONS AND METHODS OF BIOSYNTHESIZING CAROTENOIDS AND THEIR DERIVATIVES

FIELD OF THE INVENTION

The present disclosure provides recombinant microorganisms and methods for production of carotenoids and carotenoid derivatives.

BACKGROUND OF THE INVENTION

Carotenoids, the basic source of yellow, orange and red, are among the most common, naturally occurring pigments. Carotenoids are naturally biosynthesized by bacteria, algae, fungi, and plants. Carotenoids have numerous benefits for human health and commercial utility as food flavorings, colorants, nutrient supplements, cosmetics and animal feed additives and supplements. The global market for carotenoids is growing, from $1.2 billion in 2010 to an estimated $1.4 billion by 2018 with CAGR of 2.3%. For example, β-carotene is used extensively in dietary supplements and as a colorant in food, beverage, and pharmaceutical formulations, and accounted for $261 million in 2010 and will be worth $334 million in 2018; lycopene is used for food color and food additive, dietary supplements, and accounted for $66 million in 2010 and will be worth $84 million in 2018. Carotenoids are produced commercially by chemical synthesis, extraction from natural sources, or microbial fermentation. Currently, over 90% of the market is covered by chemically synthesized carotenoids.

Products of carotenoid degradation such as α-ionone and β-ionone also have commercial importance. For instance, α-ionone and β-ionone are important fragrance chemicals that are used extensively in the perfumes and fragrance industry. In particular, α-ionone has a variety of applications, ranging from flavor and fragrance to cosmetics and pharmaceutical industries. α-ionone is an unsaturated ketone with a pleasant floral scent, and is naturally found in a variety of oils of flowers of *Boronia Megastigma* (Nees), renna, in violet moss and in oil of costus root, black currants, blackberries, raspberries, black tea, plum and peach. It is commonly used as a flavor agent, including in non-alcoholic beverages, ice cream, candy, gelatins and puddings, chewing gum, and as a fragrance agent in decorative cosmetics, and in nearly all perfumes.

There are three basic methods for obtaining α-ionone: 1) chemical synthesis; 2) direct extraction from a natural source; or 3) de novo biotechnological transformation, which includes microbial and enzymatic biotransformation. None of the currently available methods of producing α-ionone are satisfactory. Chemical synthesis currently dominates the global market. However, as α-ionone is a chiral compound, chemical synthesis produces a racemic mixture, (R)(+)-α-ionone and (S)(−)-α-ionone, which have different sensorial properties, and which are too costly to separate. In nature, α-ionone is found as an almost optically pure (R)(+)-enantiomer (>99%). As such, the sensorial properties of chemically produced α-ionone are not equivalent to the natural (R)(+)-α-ionone enantiomer. Additionally, chemical synthesis is environmentally unfriendly and is not accepted by consumers who like natural products.

Direct extraction from a natural source is also not very feasible. In general, the biological systems that naturally produce carotenoids are industrially intractable and/or produce the compounds at such low levels that commercial scale isolation is not practicable. For instance, plants have been an important source of natural ionones, but they carry ionones in such low amounts that the extraction is tedious and costly. The content of α-ionone is extremely low in plants, about 1.3-81 µg/kg in raspberry and blackberry. Additionally, there are no known natural biological systems capable of producing α-ionone alone. All known natural biological systems that produce ionones either produce β-ionone or a mixture of α- and β-ionone.

De novo synthesis of α-ionone is an attractive alternative for the production of α-ionone because it yields only the desirable enantiomer, is less damaging to the environment, and does not generate toxic waste. Most importantly, α-ionone produced by this method is defined as "natural" and demands a high market value. However, currently known de novo systems use enzymes from potentially harmful bacteria. Two exogenous genes (crtB and crtI) from *Pantoea ananatis* were used for lycopene production in *Yarrowia lipolytica*. *Pantoea ananatis* is an unconventional plant pathogen bacterium implicated in diseases of a wide range of host crops, including maize and onion, *Eucalyptus*, sudangrass and honeydew melons. Its implication in human infections reveals its capacity for proliferation and potential to cause disease in a vertebrate host. As such, the bacterium carries potential risks for humans and the environment, and enzymes from such bacteria that are to be used in food or medical applications are not accorded GRAS status (generally regarded as safe) for use in food or medical applications.

Therefore, there is a need for improved biological systems capable of efficiently providing natural, non-synthetic alternatives for carotenoids, and in particular the α-ionone carotenoid derivative, at a lower cost.

SUMMARY OF THE INVENTION

In one aspect, the present disclosure provides a recombinant microorganism comprising at least one nucleic acid construct encoding a lycopene cyclase enzyme selected from lycopene ε-cyclase and lycopene β-cyclase and a carotenoid cleavage dioxygenase enzyme. The nucleic acid sequences are operably linked to one or more expression control sequences. The lycopene ε-cyclase enzyme may be from *Lactuca sativa*. The lycopene β-cyclase may be a lycopene cyclase enzyme of a bifunctional lycopene cyclase/phytoene synthase enzyme encoded by carRP of *M. circinelloides*. Alternatively, the lycopene β-cyclase may be a lycopene cyclase enzyme of a bifunctional lycopene cyclase/phytoene synthase enzyme encoded by carRA of *Phycomyces blakesleeanus*. The carotenoid cleavage dioxygenase enzyme may be CCD1 from *Daucus carota*. One or more of the nucleic acid sequences of the at least one nucleic acid construct may be operably linked to an intron-containing transcriptional elongation factor TEF promoter (TEFIN). One or more of the nucleic acid sequences of the at least one nucleic acid construct may be operably linked to an export protein promoter (EXP1). One or more of the nucleic acid sequences of the at least one nucleic acid construct may be codon-optimized for expression in the microorganism. The recombinant microorganism may comprise lycopene ε-cyclase and α-ionone. Alternatively, the recombinant microorganism may comprise lycopene β-cyclase and β-ionone.

The microorganism may be *Yarrowia lipolytica*. When the microorganism is *Yarrowia lipolytica*, the at least one nucleic acid construct may further comprise a nucleic acid sequence encoding a phytoene synthase enzyme, wherein the nucleic acid sequence is operably linked to one or more expression control sequences. The phytoene synthase enzyme may be phytoene synthase of lycopene cyclase/ phytoene synthase from *Mucor circinelloides*. The phytoene synthase enzyme may be phytoene synthase of lycopene cyclase/phytoene synthase from *Phycomyces blakesleeanus*. When the phytoene synthase enzyme is phytoene synthase of lycopene cyclase/phytoene synthase, the lycopene cyclase/phytoene synthase enzyme is modified to decrease lycopene cyclase activity. When the microorganism is *Yarrowia lipolytica*, the at least one nucleic acid construct may further comprise a nucleic acid sequence encoding a geranylgeranyl diphosphate synthase enzyme from *Yarrowia lipolytica*, wherein the nucleic acid sequence is operably linked to one or more expression control sequences. When the microorganism is *Yarrowia lipolytica*, the at least one nucleic acid construct may further comprise a nucleic acid sequence encoding a geranylgeranyl diphosphate synthase enzyme from *Xanthophyllomyces dendrorhous*, wherein the nucleic acid sequence is operably linked to one or more expression control sequences.

The microorganism may be *Saccharomyces cerevisiae*. When the microorganism is *Saccharomyces cerevisiae*, the at least one nucleic acid construct may further comprise a nucleic acid sequence encoding a phytoene synthase enzyme, wherein the nucleic acid sequence is operably linked to one or more expression control sequences. The phytoene synthase enzyme may be phytoene synthase of lycopene cyclase/phytoene synthase from *Mucor circinelloides*. The phytoene synthase enzyme may be phytoene synthase of lycopene cyclase/phytoene synthase from *Phycomyces blakesleeanus*. When the phytoene synthase enzyme is phytoene synthase of lycopene cyclase/phytoene synthase, the lycopene cyclase/phytoene synthase enzyme is modified to decrease lycopene cyclase activity. When the microorganism is *Saccharomyces cerevisiae*, the at least one nucleic acid construct may further comprise a nucleic acid sequence encoding a farnesyl diphosphate synthase enzyme from *S. cerevisiae*, wherein the nucleic acid sequence is operably linked to one or more expression control sequences. When the microorganism is *Saccharomyces cerevisiae*, the at least one nucleic acid construct may further comprise a nucleic acid sequence encoding a geranylgeranyl diphosphate synthase enzyme from *S. cerevisiae*, wherein the nucleic acid sequence is operably linked to one or more expression control sequences.

The microorganism may be *E. coli*. When the microorganism is *E. coli*, the at least one nucleic acid construct may further comprise a nucleic acid sequence encoding a phytoene synthase enzyme from *Erwinia herbicola*, wherein the nucleic acid sequence is operably linked to one or more expression control sequences. When the microorganism is *E. coli*, the at least one nucleic acid construct may further comprise a nucleic acid sequence encoding a phytoene desaturase enzyme from *Erwinia herbicola*, wherein the nucleic acid sequence is operably linked to one or more expression control sequences. When the microorganism is *E. coli*, the at least one nucleic acid construct may further comprise a nucleic acid sequence encoding a lycopene cyclase enzyme from *Erwinia herbicola*, wherein the nucleic acid sequence is operably linked to one or more expression control sequences. When the microorganism is *E. coli*, the at least one nucleic acid construct may further comprise a nucleic acid sequence encoding a geranylgeranyl diphosphate synthase enzyme from *Erwinia herbicola*, wherein the nucleic acid sequence is operably linked to one or more expression control sequences. When the microorganism is *E. coli*, the at least one nucleic acid construct may further comprise a nucleic acid sequence encoding a truncated 3-hydroxy-3-methyl-glutaryl-CoA reductase enzyme, wherein the nucleic acid sequence is operably linked to one or more expression control sequences.

The at least one nucleic acid construct may further comprise a nucleic acid sequence encoding a phytoene dehydrogenase enzyme, wherein the nucleic acid sequence is operably linked to one or more expression control sequences. The at least one nucleic acid construct may further comprise a nucleic acid sequence encoding a phytoene dehydrogenase enzyme from *Mucor circinelloides*, wherein the nucleic acid sequence is operably linked to one or more expression control sequences. The at least one nucleic acid construct may further comprise a nucleic acid sequence encoding a phytoene dehydrogenase enzyme from *Phycomyces blakesleeanus*, wherein the nucleic acid sequence is operably linked to one or more expression control sequences. The at least one nucleic acid construct may further comprise a nucleic acid sequence encoding a farnesyl diphosphate synthase enzyme, wherein the nucleic acid sequence is operably linked to one or more expression control sequences. The at least one nucleic acid construct may further comprise a nucleic acid sequence encoding a farnesyl diphosphate synthase enzyme from *Yarrowia lipolytica*, wherein the nucleic acid sequence is operably linked to one or more expression control sequences. The at least one nucleic acid construct may further comprise a nucleic acid sequence encoding a geranylgeranyl diphosphate synthase enzyme, wherein the nucleic acid sequence is operably linked to one or more expression control sequences. The at least one nucleic acid construct may further comprise a nucleic acid sequence encoding a geranylgeranyl diphosphate synthase enzyme from *Yarrowia lipolytica*, wherein the nucleic acid sequence is operably linked to one or more expression control sequences. The at least one nucleic acid construct may further comprise a nucleic acid sequence encoding a geranylgeranyl diphosphate synthase enzyme from *Xanthophyllomyces dendrorhous*, wherein the nucleic acid sequence is operably linked to one or more expression control sequences. The at least one nucleic acid construct may further comprise a nucleic acid sequence encoding a farnesyl diphosphate synthase enzyme and a geranylgeranyl diphosphate synthase enzyme, wherein the nucleic acid sequence is operably linked to one or more expression control sequences. When the microorganism is *Yarrowia lipolytica* or *Saccharomyces cerevisiae*, the at least one nucleic acid construct may further comprise a nucleic acid sequence encoding a geranylgeranyl diphosphate synthase enzyme and a farnesyl diphosphate synthase enzyme, wherein the nucleic acid sequence is operably linked to one or more expression control sequences. When the microorganism is *Yarrowia lipolytica* or *Saccharomyces cerevisiae*, the at least one nucleic acid construct may further comprise a nucleic acid sequence encoding a geranylgeranyl diphosphate synthase enzyme fused in frame with a farnesyl diphosphate synthase enzyme, wherein the nucleic acid sequence is operably linked to one or more expression control sequences. The at least one nucleic acid construct may further comprise a nucleic acid sequence encoding an acetyl-coA acetyltransferase enzyme, wherein the nucleic acid sequence is operably linked to one or more expression control sequences. The at least one nucleic acid construct may further comprise a nucleic acid sequence encoding a 3-hydroxy-3-methyl-glutaryl-CoA reductase enzyme, wherein the nucleic acid sequence is operably linked to one or more expression control sequences. The at least one nucleic acid construct may further comprise a nucleic acid sequence encoding an isopentenyl diphosphate isomerase enzyme, wherein the nucleic acid sequence is operably linked to one or more expression control sequences. The at least one nucleic acid construct may further comprise a nucleic acid sequence encoding a geranyl pyrophosphate synthase enzyme, wherein the nucleic acid sequence is operably linked to one or more expression control sequences.

In another aspect, the present disclosure provides a recombinant microorganism comprising at least one nucleic acid construct comprising a nucleic acid sequence encoding a farnesyl diphosphate synthase enzyme, a nucleic acid sequence encoding a geranylgeranyl diphosphate synthase enzyme, a nucleic acid sequence encoding a lycopene cyclase/phytoene synthase enzyme modified to decrease lycopene cyclase activity, a nucleic acid sequence encoding a phytoene dehydrogenase enzyme, a nucleic acid sequence encoding an enzyme selected from lycopene ε-cyclase and lycopene β-cyclase, and a nucleic acid sequence encoding a carotenoid cleavage dioxygenase enzyme. The geranylgeranyl diphosphate synthase enzyme may be fused in frame with the farnesyl diphosphate synthase enzyme. The recombinant microorganism may comprise lycopene ε-cyclase and α-ionone. Alternatively, the recombinant microorganism may comprise lycopene β-cyclase and β-ionone.

In yet another aspect, the present disclosure provides a recombinant microorganism comprising a nucleic acid sequence encoding a nucleic acid an acetyl-coA acetyltransferase enzyme, a nucleic acid sequence encoding a HMG-CoA reductase enzyme, a nucleic acid sequence encoding an isopentenyl diphosphate isomerase, a nucleic acid sequence encoding a geranyl pyrophosphate synthase enzyme, a nucleic acid sequence encoding a farnesyl diphosphate synthase enzyme, a nucleic acid sequence encoding a geranylgeranyl diphosphate synthase enzyme, a nucleic acid sequence encoding a lycopene cyclase/phytoene synthase enzyme modified to decrease lycopene cyclase activity, a nucleic acid sequence encoding a phytoene dehydrogenase enzyme, a nucleic acid sequence encoding a lycopene ε-cyclase enzyme, and a nucleic acid sequence encoding a carotenoid cleavage dioxygenase enzyme. The nucleic acid sequences are operably linked to one or more expression control sequences. The recombinant microorganism may comprise lycopene ε-cyclase and α-ionone. The geranylgeranyl diphosphate synthase enzyme may be fused in frame with a farnesyl diphosphate synthase enzyme.

In another aspect, the disclosure provides a recombinant microorganism comprising at least one nucleic acid construct comprising a nucleic acid sequence encoding an acetyl-coA acetyltransferase enzyme, a nucleic acid sequence encoding an HMG-CoA reductase enzyme, a nucleic acid sequence encoding an isopentenyl diphosphate isomerase, a nucleic acid sequence encoding a geranyl pyrophosphate synthase enzyme, a nucleic acid sequence encoding a farnesyl diphosphate synthase enzyme, a nucleic acid sequence encoding a geranylgeranyl diphosphate synthase enzyme, a nucleic acid sequence encoding a geranylgeranyl diphosphate synthase enzyme, a nucleic acid sequence encoding a lycopene cyclase/phytoene synthase enzyme modified to decrease lycopene cyclase activity, a nucleic acid sequence encoding a phytoene dehydrogenase enzyme, a nucleic acid sequence encoding a lycopene ε-cyclase enzyme, and a nucleic acid sequence encoding a carotenoid cleavage dioxygenase enzyme. The nucleic acid sequences are operably linked to one or more expression control sequences. The microorganism may comprise lycopene α-ionone. The geranylgeranyl diphosphate synthase enzyme may be fused in frame with a farnesyl diphosphate synthase enzyme.

In an additional aspect, the disclosure provides a recombinant microorganism comprising at least one nucleic acid construct comprising a nucleic acid sequence encoding an acetyl-coA acetyltransferase enzyme, a nucleic acid sequence encoding an HMG-CoA reductase enzyme, a nucleic acid sequence encoding an isopentenyl diphosphate isomerase, a nucleic acid sequence encoding a geranyl pyrophosphate synthase enzyme, a nucleic acid sequence encoding a farnesyl diphosphate synthase enzyme, a nucleic acid sequence encoding a geranylgeranyl diphosphate synthase enzyme, a nucleic acid sequence encoding a lycopene cyclase/phytoene synthase enzyme, a nucleic acid sequence encoding a phytoene dehydrogenase enzyme, and a nucleic acid sequence encoding a carotenoid cleavage dioxygenase enzyme. The nucleic acid sequences are operably linked to one or more expression control sequences. The microorganism may comprise β-ionone. The geranylgeranyl diphosphate synthase enzyme may be fused in frame with a farnesyl diphosphate synthase enzyme.

In another aspect, the present disclosure also provides a recombinant microorganism comprising at least one nucleic acid construct comprising a nucleic acid sequence encoding a fusion protein comprising a farnesyl diphosphate synthase enzyme fused in frame with a geranylgeranyl diphosphate synthase enzyme, a nucleic acid sequence encoding a lycopene cyclase/phytoene synthase enzyme modified to decrease lycopene cyclase activity, a nucleic acid sequence encoding a phytoene dehydrogenase enzyme, and a nucleic acid sequence encoding a lycopene ε-cyclase enzyme. The nucleic acid sequences are operably linked to one or more expression control sequences. Additionally, the farnesyl diphosphate synthase and geranylgeranyl diphosphate synthase enzymes are from *Yarrowia lipolytica*, the lycopene cyclase/phytoene synthase and phytoene dehydrogenase enzymes are from *Mucor circinelloides*, and the lycopene ε-cyclase enzyme is from *Lactuca sativa*. One or more of the enzymes are overexpressed in the microorganism by operably linking the at least one nucleic acid sequence to an intron-containing transcriptional elongation factor TEF promoter (TEFIN).

The microorganism may comprise ε-carotene. The at least one nucleic acid construct may further comprise a nucleic acid sequence encoding an acetyl-coA acetyltransferase enzyme, wherein the nucleic acid sequence is operably linked to one or more expression control sequences. The at least one nucleic acid construct may further comprise a nucleic acid sequence encoding an HMG-CoA reductase enzyme, wherein the nucleic acid sequence is operably linked to one or more expression control sequences. The at least one nucleic acid construct may further comprise a nucleic acid sequence encoding an isopentenyl diphosphate isomerase enzyme, wherein the nucleic acid sequence is operably linked to one or more expression control sequences. The at least one nucleic acid construct may further comprise a nucleic acid sequence encoding a geranyl pyrophosphate synthase enzyme, wherein the nucleic acid sequence is operably linked to one or more expression control sequences.

In another aspect, the disclosure provides a recombinant microorganism comprising at least one nucleic acid construct comprising a nucleic acid sequence encoding a fusion protein comprising a farnesyl diphosphate synthase enzyme fused in frame with a geranylgeranyl diphosphate synthase enzyme, a nucleic acid sequence encoding a lycopene cyclase/phytoene synthase enzyme, and a nucleic acid sequence encoding a phytoene dehydrogenase enzyme. The nucleic acid sequences are operably linked to one or more expression control sequences. The farnesyl diphosphate synthase and geranylgeranyl diphosphate synthase enzymes are from *Yarrowia lipolytica*, and the lycopene cyclase/phytoene synthase and phytoene dehydrogenase enzymes are from *Mucor circinelloides*. One or more of the enzymes are overexpressed in the microorganism by operably linking the at least one nucleic acid sequence to an intron-containing transcriptional elongation factor TEF promoter (TEFIN).

The microorganism may comprise β-carotene. The lycopene cyclase enzyme may be lycopene cyclase of bifunctional lycopene cyclase/phytoene synthase of *M. circinelloides*. The at least one nucleic acid construct may further comprise a nucleic acid sequence encoding an acetyl-coA acetyltransferase enzyme, wherein the nucleic acid sequence is operably linked to one or more expression control sequences. The at least one nucleic acid construct may further comprise a nucleic acid sequence encoding an HMG-CoA reductase enzyme, wherein the nucleic acid sequence is operably linked to one or more expression control sequences. The at least one nucleic acid construct may further comprise a nucleic acid sequence encoding an isopentenyl diphosphate isomerase, wherein the nucleic acid sequence is operably linked to one or more expression control sequences. The at least one nucleic acid construct further encodes a geranyl pyrophosphate synthase enzyme.

In another aspect, the disclosure provides a recombinant microorganism comprising at least one nucleic acid construct comprising a nucleic acid sequence encoding a lycopene cyclase/phytoene synthase enzyme modified to decrease lycopene cyclase activity and a nucleic acid sequence encoding a phytoene dehydrogenase enzyme, wherein the nucleic acid sequences are operably linked to one or more expression control sequences. The microorganism may comprise lycopene.

In another aspect, the disclosure provides a method of producing α-ionone, the method comprising cultivating a recombinant microorganism of any of the recombinant microorganisms described above capable of producing α-ionone under conditions sufficient for the production of α-ionone. The method may further comprise isolating α-ionone from the recombinant microorganism.

In another aspect, the disclosure provides a method of producing β-ionone, the method comprising cultivating a recombinant microorganism of any of the recombinant microorganisms described above capable of producing α-ionone under conditions sufficient for the production of β-ionone. The method may further comprise isolating β-ionone from the recombinant microorganism.

In another aspect, the disclosure provides a method of producing ε-carotene, the method comprising cultivating a recombinant microorganism of any of the recombinant microorganisms described above capable of producing α-ionone under conditions sufficient for the production of ε-carotene. The method may further comprise isolating ε-carotene from the recombinant microorganism.

In another aspect, the disclosure provides a method of producing β-carotene, the method comprising cultivating a recombinant microorganism of any of the recombinant microorganisms described above capable of producing α-ionone under conditions sufficient for the production of β-carotene. The method may further comprise isolating β-carotene from the recombinant microorganism.

In another aspect, the disclosure provides a method of producing lycopene, the method comprising cultivating a recombinant microorganism of any of the recombinant microorganisms described above capable of producing α-ionone under conditions sufficient for the production of lycopene. The method may further comprise isolating lycopene from the recombinant microorganism.

In another aspect, the disclosure provides a nucleic acid construct comprising a nucleic acid sequence encoding a lycopene cyclase enzyme selected from lycopene ε-cyclase and lycopene β-cyclase, and a nucleic acid sequence encoding a carotenoid cleavage dioxygenase enzyme. The nucleic acid sequences are operably linked to one or more expression control sequences. The lycopene ε-cyclase enzyme may be from *Lactuca sativa*. The lycopene β-cyclase enzyme is lycopene cyclase of a bifunctional lycopene cyclase/phytoene synthase of *M. circinelloides*. Alternatively, the lycopene β-cyclase enzyme may be lycopene cyclase of bifunctional lycopene cyclase/phytoene synthase of *Phycomyces blakesleeanus*. The carotenoid cleavage dioxygenase enzyme may be CCD1 from *Daucus carota*. The nucleic acid construct may further comprise a nucleic acid sequence encoding a phytoene dehydrogenase enzyme. The phytoene dehydrogenase enzyme may be from *Mucor circinelloides*. The phytoene dehydrogenase enzyme may also be from *Phycomyces blakesleeanus*. The nucleic acid construct may further comprise a nucleic acid sequence encoding a phytoene synthase enzyme. The phytoene synthase enzyme may be phytoene synthase of lycopene cyclase/phytoene synthase from *Mucor circinelloides*. Alternatively, the phytoene synthase enzyme may be phytoene synthase of lycopene cyclase/phytoene synthase from *Phycomyces blakesleeanus*. When the phytoene synthase enzyme is phytoene synthase of lycopene cyclase/phytoene synthase enzyme, the lycopene cyclase/phytoene synthase enzyme is modified to decrease lycopene cyclase activity. The phytoene synthase enzyme may also be from *Erwinia herbicola*. The nucleic acid construct may further comprise a nucleic acid sequence encoding a phytoene desaturase enzyme from *Erwinia herbicola*. The nucleic acid construct may further comprise a nucleic acid sequence encoding a lycopene cyclase enzyme from *Erwinia herbicola*. The nucleic acid construct may further comprise a nucleic acid sequence encoding a farnesyl diphosphate synthase enzyme. The nucleic acid construct may further comprise a nucleic acid sequence encoding a farnesyl diphosphate synthase enzyme from *Yarrowia lipolytica*. The nucleic acid construct may further comprise a nucleic acid sequence encoding a farnesyl diphosphate synthase enzyme from *S. cerevisiae*. The nucleic acid construct may further comprise a nucleic acid sequence encoding a geranylgeranyl diphosphate synthase enzyme. The nucleic acid construct may further comprise a nucleic acid sequence encoding a geranylgeranyl diphosphate synthase enzyme from *Yarrowia lipolytica*. The nucleic acid construct may further comprise a nucleic acid sequence encoding a geranylgeranyl diphosphate synthase enzyme from *Xanthophyllomyces dendrorhous*. The nucleic acid construct may further comprise a nucleic acid sequence encoding a geranylgeranyl diphosphate synthase enzyme from *S. cerevisiae*. The nucleic acid construct may further comprise a nucleic acid sequence encoding a geranylgeranyl diphosphate synthase enzyme from *Erwinia herbicola*. The nucleic acid construct may further comprise a nucleic acid sequence encoding a farnesyl diphosphate synthase enzyme and a geranylgeranyl diphosphate synthase enzyme. The nucleic acid construct may further comprise a nucleic acid sequence encoding a geranylgeranyl diphosphate synthase enzyme fused in frame with a farnesyl diphosphate synthase enzyme. The nucleic acid construct may further comprise a nucleic acid sequence encoding an acetyl-coA acetyltransferase enzyme. The nucleic acid construct may further comprise a nucleic acid sequence encoding a 3-hydroxy-3-methyl-glutaryl-CoA reductase enzyme. The nucleic acid construct may further comprise a nucleic acid sequence encoding a truncated 3-hydroxy-3-methyl-glutaryl-CoA reductase enzyme. The nucleic acid construct may further comprise a nucleic acid sequence encoding an isopentenyl diphosphate isomerase. The nucleic acid construct may further comprise a nucleic acid sequence encoding a geranyl pyrophosphate synthase enzyme.

The nucleic acid sequences are operably linked to one or more expression control sequences. One or more of the nucleic acid sequences may be operably linked to an intron-containing transcriptional elongation factor TEF promoter (TEFIN). Alternatively, one or more of the nucleic acid sequences may be operably linked to an export protein promoter (EXP1). The nucleic acid construct may be codon-optimized for expression in a heterologous microorganism.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

The following drawings form part of the present disclosure and are included to further demonstrate certain aspects of the present disclosure. The disclosure may be better understood by reference to one or more of these drawings in combination with the detailed description of specific aspects presented herein.

DETAILED DESCRIPTION

Figure 1:
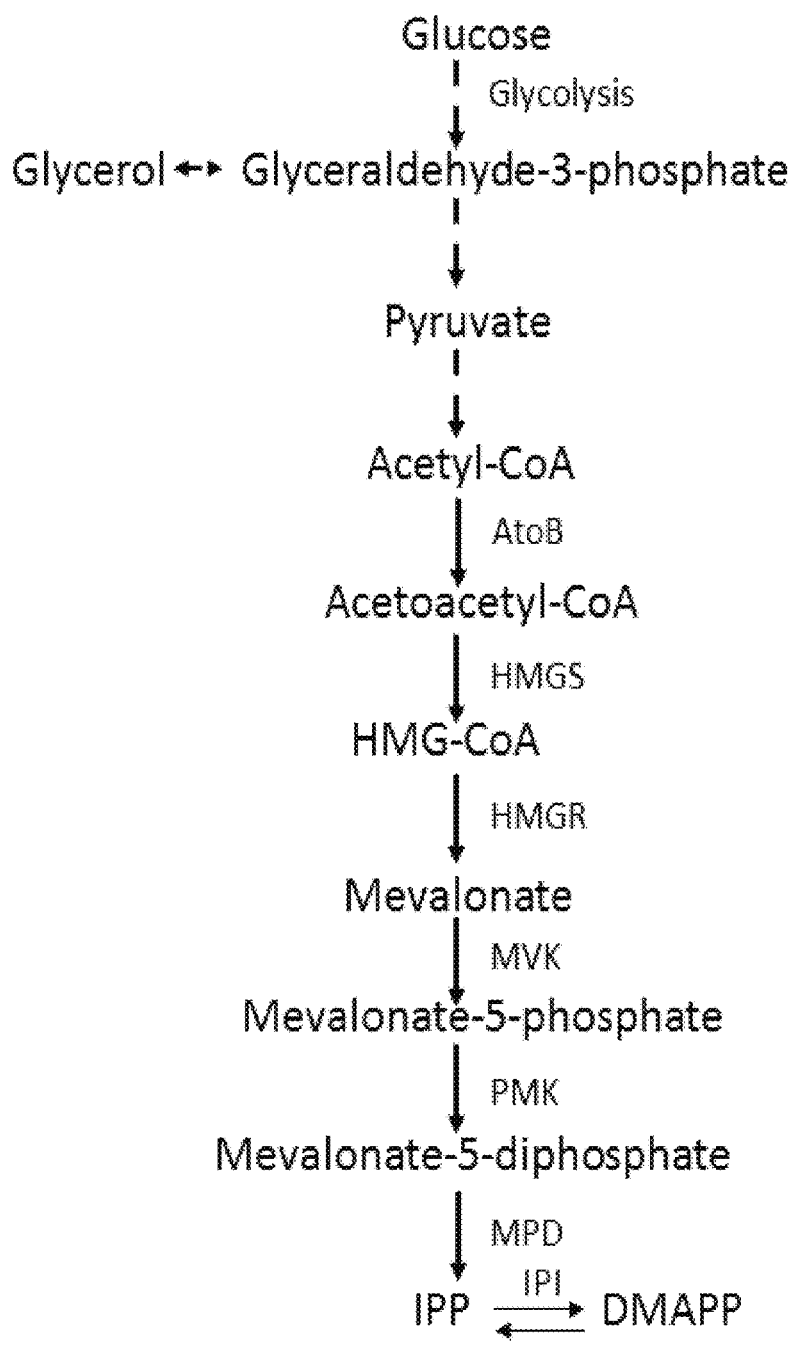
FIG. 1. Schematic depicting the metabolic pathway from glucose to IPP and DMAPP in yeast. The pathway consists of the glycolytic pathway and mevalonate pathway. AtoB, acetoacetyl-CoA thiolase; HMGS, HMG-CoA synthase; HMGR, HMG-CoA reductase; MVK, Mevalonate kinase; PMK, Phosphomevalonate kinase, MPD, Mevalonate-5-pyrophosphate decarboxylase; IPP, Isopentenyl-pyrophosphate; DMAPP, Dimethylallyl diphosphate; IPI, IPP isomerase.

The present disclosure is based in part on the discovery that industrially significant quantities of carotenoids and carotenoid products for commercial uses can desirably be produced in genetically modified microorganisms. Described herein is an engineered pathway capable of producing enatiomerically pure (R)(+)-α-ionone, which can be constructed in microorganisms. Advantageously, such a pathway produces enatiomerically pure α-ionone without the concomitant production of β-ionone. Additionally, the pathway can be constructed using nucleic acids encoding enzymes from microorganisms that do not carry any risk for humans and the environment, thereby providing a natural, safe alternative to chemical synthesis, and greater ease of isolation. As such, the present disclosure provides recombinant microorganisms encoding enzymes in a pathway for producing enatiomerically pure (R)(+)-α-ionone, and methods of using the recombinant microorganisms for producing enatiomerically pure (R)(+)-α-ionone. The invention also provides methods of producing carotenoids and carotenoid products, and methods of harvesting the carotenoids and carotenoid products.

I. Recombinant Microorganism

In one aspect, the present disclosure provides a recombinant microorganism capable of biosynthesizing one or more carotenoid or carotenoid derivatives. A recombinant microorganism of the invention comprises at least one nucleic acid construct encoding carotenoid biosynthetic enzymes. In particular, a recombinant microorganism of the present disclosure is capable of biosynthesizing industrially tractable quantities of lycopene, ε-carotenoid, β-ionone, and enantiomerically pure (R)(+)-α-ionone. The microorganism, carotenoid biosynthetic enzymes, and the genetic engineering of microorganism to produce carotenoids and carotenoid derivatives are discussed in more detail below.

(a) Microorganisms

A recombinant microorganism of the present disclosure may be any microorganism provided the microorganism is generally regarded as safe for use in food or medical applications. In general, a microorganism of the disclosure is a bacterium, a fungus, or an alga. Preferably, a microorganism of the disclosure is a bacterium or a fungus. When selecting a particular microorganism for use in accordance with the present invention, it will generally be desirable to select a microorganism whose cultivation characteristics are amendable to commercial scale production. In general, any modifiable and cultivatable microorganism may be employed.

A microorganism may be naturally capable of producing carotenoids or their derivatives. When a microorganism is naturally capable of producing carotenoids or their derivatives, the microorganism may be genetically engineered to alter expression of one or more endogenous enzymes to enhance production of carotenoids or their derivatives. In addition, when a microorganism is naturally capable of producing carotenoids or their derivatives, the microorganism may be genetically engineered to express one or more exogenous enzymes to enhance production of carotenoids or their derivatives. A microorganism may also be genetically engineered to alter expression of one or more endogenous genes, and to express one or more exogenous genes to enhance production of carotenoids or their derivatives.

A suitable microorganism may be a fungal microorganism capable of producing carotenoids or their derivatives. Fungal microorganisms that are naturally capable of producing carotenoids or their derivatives are known in the art. Non-limiting examples of genera of fungi that are naturally capable of producing carotenoids or their derivatives may include *Blakeslea, Candida, Cryptococcus, Cunninghamella, Lipomyces, Marlierella, Mucor, Phycomyces, Pythium, Rhodosporidium, Rhodotorula, Trichosporon,* and *Yarrowia.* Any fungus belonging to these genera may be utilized as host fungi according to the present invention, and may be engineered or otherwise manipulated to generate inventive, carotenoid and derivative producing fungal strains. Organisms of species that include, but are not limited to, *Blakeslea trispora, Candida utilis, Candidapulcherrima, C. revkauji, C. tropicalis, Cryptococcus curvatus, Cunninghamella echinulata, C. elegans, C. japonica, Lipomyces starkeyi, L. lipoferus, Mortierella alpina, M. isabellina, M. ramanniana, M. vinacea, Mucor circinelloides, Phycomyces blakesleanus, Pythium irregulare, Rhodosporidium toruloides, Rhodotorula glutin is, R. gracilis, R. graminis, R. mucilaginosa, R. pinicola, Schizosaccharomyces pombe, Trichosporon pullans, T. cutaneum, Yarrowia lipolytica,* and *Xanthophyllomyces dendrorhous,* may be used.

Alternatively, the fungus may not be naturally capable of producing carotenoids and derivatives of carotenoids. When the fungus is not naturally capable of producing carotenoids or their derivatives, the fungus is generally recombinant to express one or more exogenous genes to reconstruct a carotenoid biosynthetic pathway for production of carotenoids or their derivatives. Non-limiting examples of genera of fungi that are not naturally capable of producing carotenoids or their derivatives, but that may be suitable for use in the present disclosure, may include *Aspergillus, Botrytis, Cercospora, Fusarium (Gibberella), Kluyveromyces, Neurospora, Penicillium, Pichia (Hansenula), Puccinia, Saccharomyces, Schizosaccharomyces, Sclerotium, Trichoderma,* and *Xanthophyllomyces (Phaffia).* Organisms of species that include, but are not limited to, *Aspergillus nidulans, A. niger, A. terreus, Botrytis cinerea, Cercospora nicotianae, Fusarium fujikuroi (Gibberella zeae), Kluyveromyces lactis, K. lactis, Neurospora crassa, Pichia pastoris, Puccinia distincta, Saccharomyces cerevisiae, Sclerotium rolfsii, Schizosaccharomyces pombe, Trichoderma reesei,* and *Xanthophyllomyces dendrorhous (Phaffia rhodozyma),* may be used.

A fungal microorganism of the disclosure may be *Yarrowia lipolytica.* Advantages of *Y. lipolytica* include, for example, tractable genetics and molecular biology, availability of genomic sequence (see, for example, Sherman et al., *Nucleic Acids Res.* 32 (Database issue):D315-8, 2004), suitability to various cost-effective growth conditions, and ability to grow to high cell density. Furthermore, there is already extensive commercial experience with *Y. lipolytica.*

*Saccharomyces cerevisiae* is also a useful host cell in accordance with the present invention, particularly due to its experimental tractability and the extensive experience that researchers have accumulated with the organism. Although cultivation of *Saccharomyces* under high carbon conditions may result in increased ethanol production, this can generally be managed by process and/or genetic alterations.

Other preferred fungal microorganisms of the disclosure may be *Candida utilis, Pichia pastoris, Schizosaccharomyces pombe, Blakeslea trispora,* and *Xanthophyllomyces dendrorhous.* The edible yeast *C. utilis* is an industrially important microorganism approved by the U.S. Food and Drug Administration as a safe substance. Through its large-scale production, *C. utilis* has become a promising source of single-cell protein as well as a host for the production of several chemicals, such as glutathione. *P. pastoris* is another non-carotenogenic yeast that has also been studied to production of carotenoids, and it is able to grow in organic materials.

A suitable microorganism may be a bacterial microorganism capable of producing carotenoids or their derivatives. Bacterial microorganisms that are naturally capable of producing carotenoids or their derivatives are known in the art. Non-limiting examples of a bacterial microorganism capable of producing carotenoids or their derivatives may include *Erwinia* species, and *Agrobacterium aurantiacum.*

Alternatively, the bacterium may not be naturally capable of producing carotenoids and derivatives of carotenoids.

Non-limiting examples of genera of bacteria that are not naturally capable of producing carotenoids or their derivatives, but that may be suitable for use in the present disclosure, may include *Escherichia coli* and *Zymomonas mobilis*. *Escherichia coli* and *Zymomonas mobilis* do not naturally synthesize carotenoids, but by using carotenogenic genes, recombinant strains of such bacteria capable of accumulating lycopene, beta-carotene, and astaxanthin have been produced.

A bacterial microorganism of the disclosure may be *Escherichia coli*, an intensively studied microorganism with tractable genetics that is also extensively used in industrial manufacturing for its suitability to various cost-effective growth conditions, and its ability to grow to high cell density.

(b) Enzymes and Pathways

The genes and enzymes of the carotenoid biosynthetic pathway are almost completely elucidated in plant, algae, bacteria, and fungi. In brief, carotenoid biosynthesis originates from the mevalonate (MVA) pathway shown in FIG. 1 and produces isopentenyl phosphate (IPP) and dimethylallyl pyrophosphate (DMAPP) using acetyl-CoA as a starting compound. The pyruvate is converted into acetyl-CoA by the action of pyruvate decarboxylase (PDC), cytosolic acetyldehyde dehydrogenase (ALD), and acetyl-CoA synthetase (ACS) (Pronk et al. *Yeast*. 12: 1607-1633, 1996). In the cytosol, acetyl-CoA is also generated through the action of ATP-citrate lyase (ACL) from citrate. Citrate is synthesized in the mitochondria through tricarboxylic acid (TCA) cycle, and can be moved into the cytosol (in exchange for malate) by citrate/malate translocase. Carotenoid biosynthesis requires the enzymes of the mevalonate pathway, of which acetyl-CoA acetyltransferase (AtoB), HMG-CoA reductase enzyme (HMGR), and isopentenyl diphosphate isomerase (IPI) are step-limiting. As such, any recombinant microorganism of the present disclosure may be further genetically modified to express enzymes of the mevalonate pathway. In particular, a microorganism may be genetically modified to express step-limiting enzymes of the mevalonate pathway. As it will be recognized in the art, expressing step-limiting enzymes, including expressing step-limiting enzymes of the mevalonate pathway, may improve production of any metabolites dependent from compounds produced by the mevalonate pathway.

Figure 2:
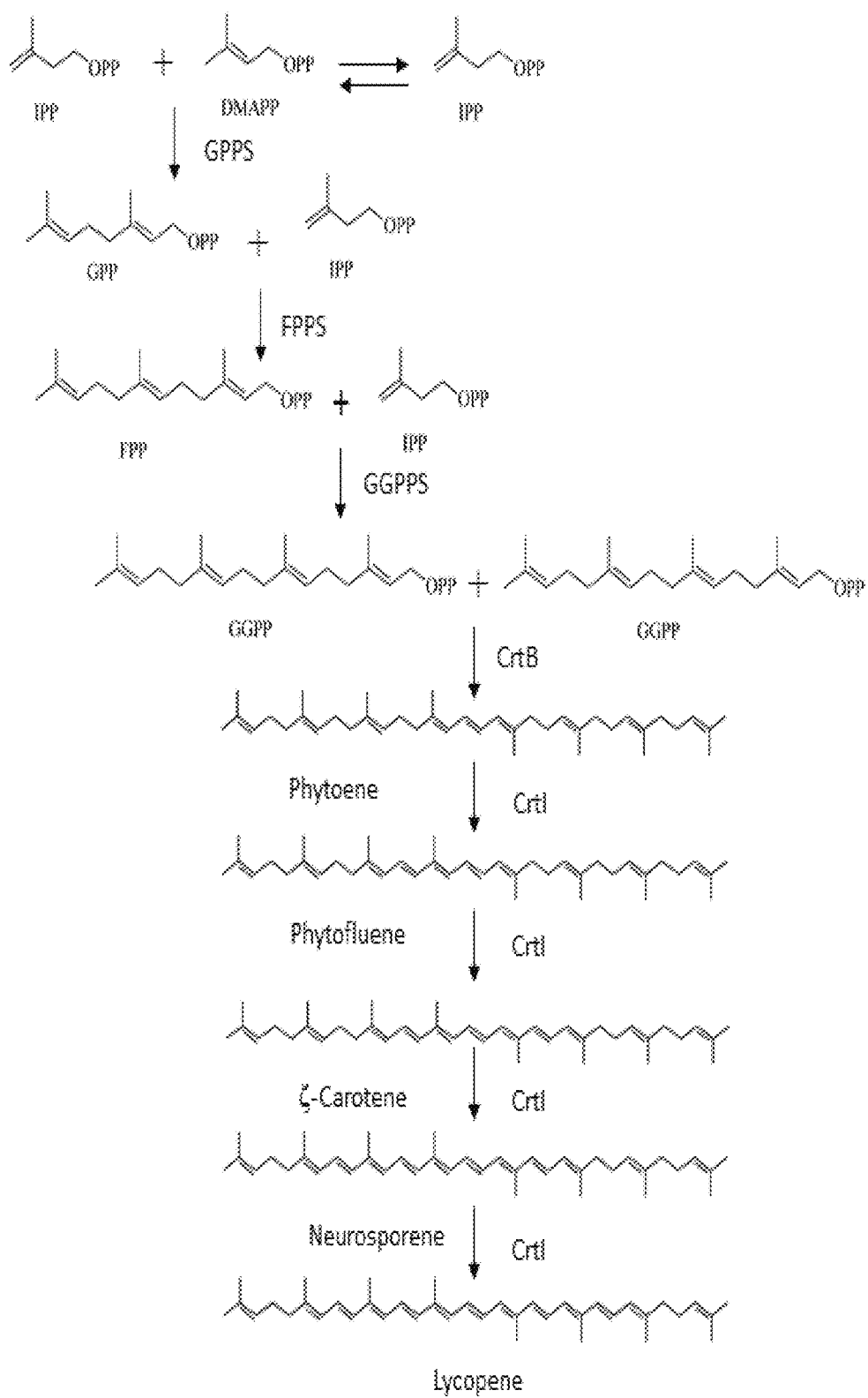
FIG. 2. Pathway for synthesis of lycopene from IPP and DMAPP in bacteria. GPP, Geranyl diphosphate; GPPS, Geranyl diphosphate synthase; FPP, Farnesyl diphosphate; FPPS, Farnesyl diphosphate synthase; GGPP, geranylgeranyl diphosphate; GGPPS, geranylgeranyl diphosphate synthase; crtB, Phytoene synthase; crtI, Phytoene desaturase.
Figure 3:
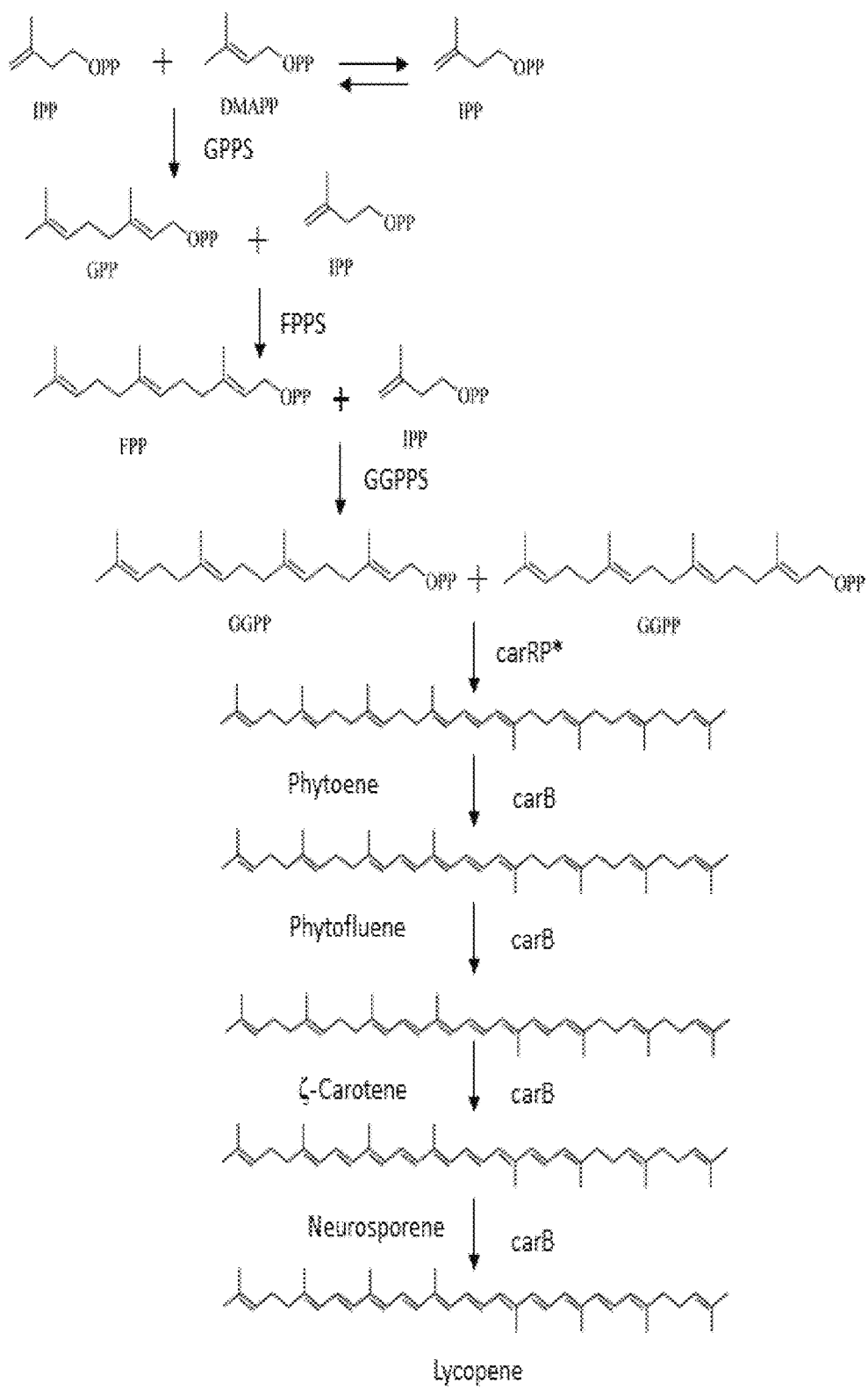
FIG. 3. Reconstruction of the lycopene pathway with the genes carRP* and carB in *Y. lipolytica*. carRP*, Mutated phytoene synthase/lycopene cyclase; carB, Phytoene dehydrogenase.

Carotenoid biosynthesis further requires geranylgeranyl diphosphate synthase (GGPPS), farnesyl diphosphate synthase (FPPS), phytoene synthase (PSases), and phytoene desaturase for the production of the C40 lycopene (FIG. 2 and FIG. 3). The condensation of two GGPP molecules forming phytoene is the first committed step in the carotenoid biosynthetic pathway. For example, the expression of mutated *Taxus canadensis* GGPPS result in an approximately 1.7-fold increase in levopimaradiene production (See, for example, Leonard et al. PNAS, 107(31): 13654-13659, 2010).

Figure 4:
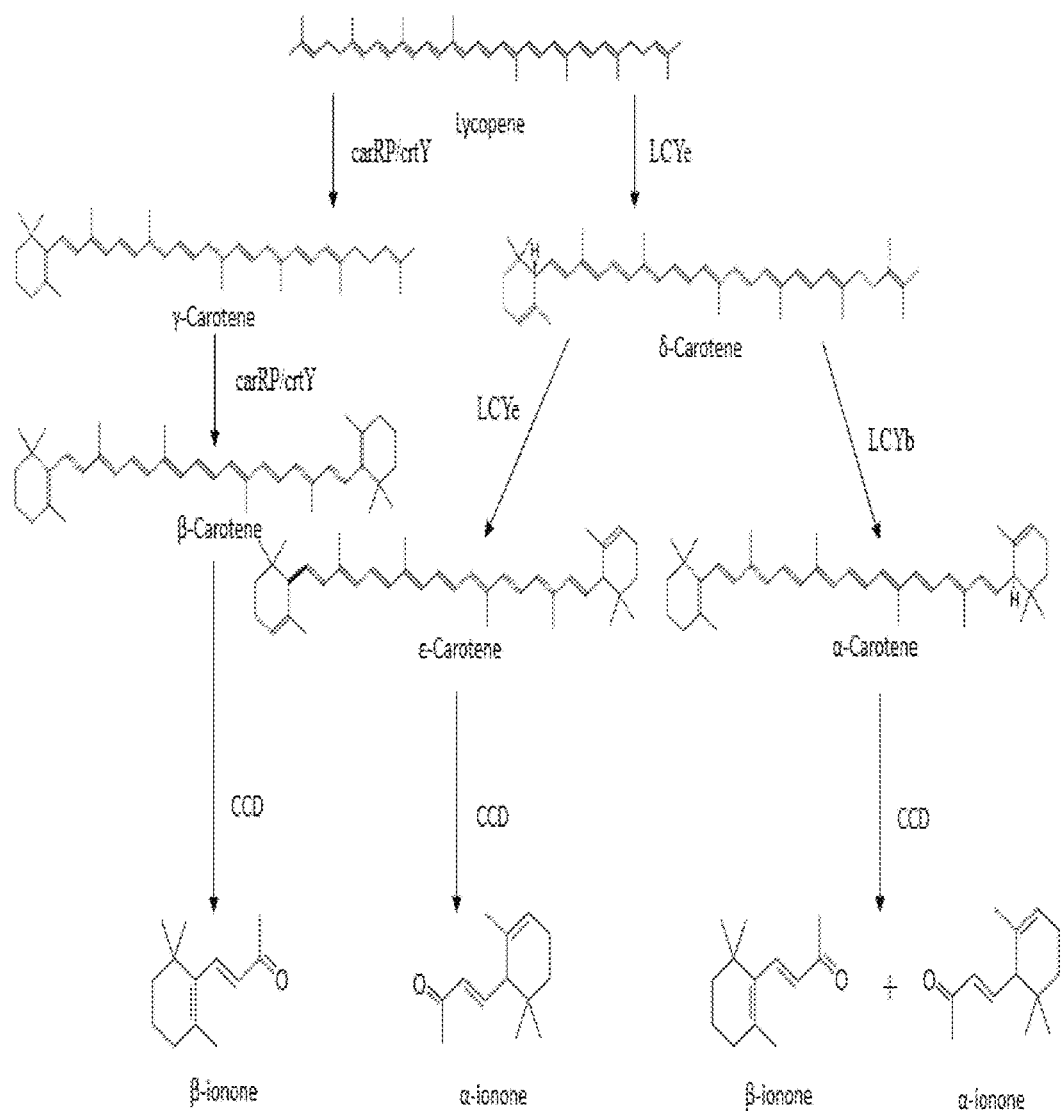
FIG. 4. Proposed pathway for α-ionone and β-ionone from lycopene. The linear lycopene is converted to β-carotene by carRP or lycopene β-cyclase (crtY); lycopene ε-cyclase (LCYe) add one ε-ring to lycopene to form the monocyclic β-carotene; LCYe and lycopene β-cyclase (LCYb) add a ε-ring and β-ring to β-carotene to form ε-carotene and α-carotene, respectively; oxidative enzymatic cleavage of β-carotene, ε-carotene, and α-carotene by carotenoid cleavage dioxygenase (CCD) yields β-ionone, α-ionone, and a mixture of β-ionone and α-ionone, respectively.

After lycopene synthesis, further cyclases, ketolases and hydroxylases result in the production of different carotenoids from lycopene (FIG. 4). Lycopene is the substrate of two competing cyclases: lycopene ε-cyclase (LCYe) and lycopene β-cyclase (LCYb). When acting together on the two ends of the molecule, LCYe and LCYb form α-carotene. The action of LCYe alone forms δ- and ε-carotene. The action of crtY/carRP alone forms γ- and β-carotene. Subsequently, the various carotenes are cleaved by carotenoid cleavage enzymes (CCDs) yielding α-ionone and β-ionone (FIG. 4).

According to the present invention, carotenoid production in a host microorganism may be adjusted by modifying the expression or activity of one or more enzymes involved in carotenoid biosynthesis and carotenoid derivative biosynthesis. Such modification comprises expression of one or more heterologous nucleic acids encoding carotenoid biosynthetic enzymes and carotenoid derivative biosynthetic enzymes into the host cell. Alternatively or additionally, modifications may be made to the expression or activity of one or more endogenous or heterologous carotenoid biosynthetic enzymes and carotenoid derivative biosynthetic enzymes. Given the considerable conservation of components of the carotenoid biosynthetic enzymes, it is expected that heterologous carotenoid biosynthetic enzymes and carotenoid derivative biosynthetic enzymes will often function even in significantly divergent organisms. Furthermore, should it be desirable to introduce more than one heterologous carotenoid biosynthetic enzyme or carotenoid derivative biosynthetic enzyme, in many cases polypeptides from different source organisms will function together. A plurality of different heterologous carotenoid biosynthetic enzymes and carotenoid derivative biosynthetic enzymes may be expressed in the same host cell. This plurality contains only polypeptides from the same source organism (e.g., two or more sequences of, or sequences derived from, the same source organism). The plurality includes polypeptides independently selected from different source organisms (e.g., two or more sequences of, or sequences derived from, at least two independent source organisms).

In general, a microorganism is genetically engineered to produce or increase production of lycopene from which all other carotenoids and carotenoid derivatives are produced, to produce or increase production of one or more carotenoids (for example, produce or increase production of ε-carotene), to shift production from one carotenoid (e.g., α-carotene) to another (e.g., ε-carotene), to produce or increase production of one or more carotenoid derivatives (for example, α-ionone), to shift production from one carotenoid derivative (e.g., β-ionone) to another (e.g., α-ionone), or combinations thereof. Introduction of one or more carotenogenic modifications (e.g., increased expression of one or more endogenous or heterologous carotenogenic polypeptides), in accordance with the present invention, can achieve these goals. For instance, a microorganism of the present disclosure may be genetically engineered to express any one or more of pyruvate decarboxylase, cytosolic acetyldehyde dehydrogenase, acetyl-CoA synthetase, ATP-citrate lyase, acetoacetyl-CoA thiolase, HMG-CoA synthase, 3-hydroxy-3-methylglutaryl-CoA reductase, Mevalonate kinase, Phosphomevalonate kinase, Mevalonate pyrophosphate decarboxylase, Isopentenyl diphosphate isomerase, farnesyl pyrophosphate synthase, geranylgeranyl pyrophosphate synthase, phytoene synthase, phytoene desaturase, lycopene β-cyclase, lycopene ε-cyclase, and one or more carotenoid cleavage dioxygenases.

The genetic modifications for producing, increasing production, or shifting production of carotenoids and carotenoid derivatives described herein are described further below. A genetically modified microorganism may encode any of the carotenoid enzymes, but with some further modifications designed to enhance production of the carotenoid or carotenoid derivative.

As described above, the selection of the organism of origin of the enzyme may be important and is preferably an organism generally regarded as safe. Non-limiting examples of organisms of origin of metabolic enzymes that may be regarded as safe include *Mucor circinelloides*, *Phycomyces* blakesleeanus, *Y. lipolytica, Saccharomyces cerevisiae, Candida utilis, Pichia pastoris*, and *Schizosaccharomyces pombe*.

A. Lycopene

A microorganism of the present disclosure may be genetically engineered to produce or increase production of lycopene. As shown in FIGS. 2 and 3, biosynthetic enzymes of lycopene synthesis starts with IPP and DMAPP and require the activity of geranyl pyrophosphate synthase (GPPS), farnesyl diphosphate synthase (FPPS), geranylgeranyl diphosphate synthase (GGPPS), phytoene synthase (PSase), and phytoene dehydrogenase enzymes. As such, a microorganism of the present disclosure may be genetically engineered to express any combination of one or more of the lycopene biosynthetic enzymes. For instance, a microorganism may be genetically engineered to express geranyl pyrophosphate synthase, farnesyl diphosphate synthase, geranylgeranyl diphosphate synthase, phytoene synthase, and phytoene dehydrogenase. Alternatively, a microorganism of the present disclosure may be genetically engineered to express any combination of one or more of geranyl pyrophosphate synthase, farnesyl diphosphate synthase, geranylgeranyl diphosphate synthase, phytoene synthase, and phytoene dehydrogenase.

The choice of lycopene biosynthetic enzyme or combination of biosynthetic enzymes that are expressed in a microorganism can and will vary depending on the specific microorganism host cell or strain, and its ability to produce lycopene. For instance, when the microorganism is *Y. lipolytica*, a recombinant *Y. lipolytica* may express geranyl pyrophosphate synthase (GPPS), farnesyl diphosphate synthase (FPPS), geranylgeranyl diphosphate synthase (GGPPS), phytoene synthase (PSase), and phytoene dehydrogenase. Preferably, when the microorganism is *Y. lipolytica*, the *Y. lipolytica* microorganism is a recombinant microorganism expressing phytoene synthase (PSase), and phytoene dehydrogenase. Also preferred when the microorganism is *Y. lipolytica*, a recombinant *Y. lipolytica* expresses farnesyl diphosphate synthase (FPPS), geranylgeranyl diphosphate synthase (GGPPS), phytoene synthase (PSase), and phytoene dehydrogenase. As explained above, a recombinant *Y. lipolytic* may further express enzymes of the MVA pathway.

Preferably, when a recombinant microorganism is *Y. lipolytica* phytoene synthase (PSase) and phytoene dehydrogenase enzymes are encoded by *M. circinelloides*, which is an organism generally regarded as safe. *M. circinelloides* is a β-carotene-producing filamentous fungus, and the biosynthetic pathway of carotenoid biosynthesis is well characterized. The *M. circinelloides* genes encoding PSase and phytoene dehydrogenase have been isolated. The carB gene of *M. circinelloides* (SEQ ID NO: 58) encodes a phytoene dehydrogenase enzyme (SEQ ID NO: 61). Preferably, the codon-optimized carB gene of *M. circinelloides* encoded by SEQ ID NO: 59 is used as a source of the phytoene dehydrogenase enzyme for producing lycopene.

The carRP gene of *M. circinelloides* (SEQ ID NO: 62) encodes an enzyme comprising two domains (SEQ ID NO: 64): the P domain determines phytoene synthase activity, and the R domain is responsible for lycopene cyclase activity which cyclizes lycopene to γ-carotene. The R domain is functional even in the absence of the P domain, while the P domain needs the proper R domain conformation to carry out its function. Preferably, when the carRP gene of *M. circinelloides* is used as a source of the PSase enzyme activity for producing lycopene, the carRP gene is modified to decrease or inhibit lycopene cyclase activity (carRP*) (SEQ ID NO: 65). As used herein, the term "decrease or inhibit" refer to a substantial or complete elimination of the activity of an enzyme such as lycopene cyclase. As such, decreasing or inhibiting the lycopene cyclase activity of the carRP gene of *M. circinelloides* prevents or substantially reduces the cyclization of the lycopene to γ-carotene, and ensures the accumulation of lycopene in the microorganism. More preferred, the codon-optimized modified carRP gene of *M. circinelloides* (carRP*) encoded by SEQ ID NO: 66 is used as a source of the PSase enzyme activity for producing lycopene.

Alternatively, the carRA gene of *Phycomyces blakesleeanus* (SEQ ID NO: 67), which is homologous to the carRP gene of *M. circinelloides*, may also be used. As with the carRP gene of *M. circinelloides*, modifying the carRA gene of *P. blakesleeanus* to express an enzyme with modifications to the amino acids 77 or 215 of the R domain produces an enzyme deficient in lycopene cyclase activity.

Also preferred, when a recombinant microorganism is *Y. lipolytica* expressing farnesyl diphosphate synthase (FPPS), a recombinant *Y. lipolytica* expresses FPPS of *Y. lipolytica*. More preferably, FPPS of *Y. lipolytica* is encoded by nucleic acid sequence of SEQ ID NO: 72.

When a recombinant microorganism is *Y. lipolytica* expressing geranylgeranyl diphosphate synthase (GGPPS), a recombinant *Y. lipolytica* preferably expresses GGPPS of *Y. lipolytica*. More preferably, GGPPS of *Y. lipolytica* is encoded by nucleic acid sequences SEQ ID NO: 70. Alternatively, a recombinant *Y. lipolytica* preferably expresses GGPPS of *Xanthophyllomyces dendrorhous*.

Also preferred, when a recombinant microorganism is *Y. lipolytica* expressing farnesyl diphosphate synthase (FPPS) and geranylgeranyl diphosphate synthase (GGPPS), a recombinant *Y. lipolytica* expresses FPPS and GGPPS enzymes of *Y. lipolytica*. More preferably, FPPS and GGPPS enzymes of *Y. lipolytica* are encoded by nucleic acid sequences SEQ ID NO: 72 and SEQ ID NO: 70, respectively.

Further modifications of genes and enzymes expressed in a microorganism designed to enhance production of the carotenoid or carotenoid derivatives may also be used. For instance, when FPPS and GGPPS are expressed in a recombinant microorganism of the disclosure, FPPS to GGPPS may be fused to increase production of geranyl geraniol, thereby enhancing production of lycopene and other carotenoids and their derivatives. As such it is preferred that when a recombinant microorganism is *Y. lipolytica* expressing farnesyl diphosphate synthase (FPPS) and geranylgeranyl diphosphate synthase (GGPPS), the recombinant *Y. lipolytica* expresses a fusion of FPPS and GGPPS. Preferably, when a recombinant microorganism is *Y. lipolytica* expressing farnesyl diphosphate synthase (FPPS) and geranylgeranyl diphosphate synthase (GGPPS), the recombinant *Y. lipolytica* expresses a fusion of FPPS and GGPPS of SEQ ID NO: 74 encoded by SEQ ID NO: 73.

When the microorganism is *S. cerevisiae*, a recombinant *S. cerevisiae* may express 3-hydroxy-3-methyl-glutaryl-CoA reductase (HMGR), geranyl pyrophosphate synthase (GPPS), farnesyl diphosphate synthase (FPPS), geranylgeranyl diphosphate synthase (GGPPS), phytoene synthase (PSase), and phytoene dehydrogenase. Preferably, when a microorganism is *S. cerevisiae*, the microorganism is a recombinant *S. cerevisiae* expressing phytoene synthase (PSase), and phytoene dehydrogenase. Also preferred when the microorganism is *S. cerevisiae*, a recombinant *S. cerevisiae* expresses geranyl pyrophosphate synthase (GPPS), farnesyl diphosphate synthase (FPPS), geranylgeranyl diphosphate synthase (GGPPS), phytoene synthase (PSase), and phytoene dehydrogenase. Most preferred when the microorganism is *S. cerevisiae*, a recombinant *S. cerevisiae* expresses geranyl pyrophosphate synthase (GPPS), farnesyl diphosphate synthase (FPPS), geranylgeranyl diphosphate synthase (GGPPS), phytoene synthase (PSase), and phytoene dehydrogenase. As explained above, a recombinant *S. cerevisiae* may further express enzymes of the MVA pathway.

Preferably, when a recombinant microorganism is *S. cerevisiae*, phytoene synthase (PSase) and phytoene dehydrogenase are the PSase and phytoene dehydrogenase enzymes of *M. circinelloides*. Preferably, the carB gene of *M. circinelloides* encoded by SEQ ID NO: 58 is used as a source of the phytoene dehydrogenase enzyme for producing lycopene. More preferred, the codon-optimized carB gene of *M. circinelloides* encoded by SEQ ID NO: 60 is used as a source of the phytoene dehydrogenase enzyme for producing lycopene.

Also preferably when a recombinant microorganism is *S. cerevisiae*, the modified carRP* gene of *M. circinelloides* encoded by SEQ ID NO: 65 is used as a source of the phytoene synthase enzyme for producing lycopene. More preferred, the codon-optimized modified carRP* gene of *M. circinelloides* encoded by SEQ ID NO: 68 is used as a source of the phytoene synthase enzyme for producing lycopene. The carRA gene of *Phycomyces blakesleeanus* (SEQ ID NO: 67) may also be used when a recombinant microorganism is *S. cerevisiae*.

Also preferred, when a recombinant microorganism is *S. cerevisiae*, the recombinant *S. cerevisiae* expresses the FPPS and GGPPS enzymes of *S. cerevisiae*. More preferably, the FPPS and GGPPS enzymes of *S. cerevisiae* are encoded by nucleic acid sequences SEQ ID NO: 75 and SEQ ID NO: 77, respectively. More preferred when a recombinant microorganism is *S. cerevisiae*, the recombinant *S. cerevisiae* expresses a fusion of FPPS and GGPPS. Preferably, when a recombinant microorganism is *S. cerevisiae* expressing farnesyl diphosphate synthase (FPPS) and geranylgeranyl diphosphate synthase (GGPPS), the recombinant *S. cerevisiae* expresses a fusion of FPPS and GGPPS of SEQ ID NO: 80 encoded by SEQ ID NO: 79.

Also preferred, when a recombinant microorganism is *S. cerevisiae*, the recombinant *S. cerevisiae* expresses the 3-hydroxy-3-methyl-glutaryl-CoA reductase (HMGR) enzyme of *S. cerevisiae*. More preferably, the HMGR enzyme of *S. cerevisiae* is a truncated 3-hydroxy-3-methyl-glutaryl-CoA reductase (tHMG1). More preferred when a recombinant microorganism is *S. cerevisiae*, the recombinant *S. cerevisiae* expresses a truncated 3-hydroxy-3-methyl-glutaryl-CoA reductase of SEQ ID NO: 82 encoded by SEQ ID NO: 81.

When a microorganism is *E. coli*, a recombinant *E. coli* capable of producing lycopene may express geranylgeranyl pyrophosphate synthase, phytoene synthase, and phytoene desaturase, and phytoene cyclase. Preferably, the geranylgeranyl pyrophosphate synthase, phytoene synthase, and phytoene desaturase, are from *Erwinia herbicola*.

B. Carotene

A microorganism of the present disclosure may be genetically engineered to produce or increase production of one or more carotenoids. Alternatively, a microorganism of the present disclosure may be genetically engineered to shift production from one carotenoid to another.

As shown in FIG. 4, lycopene is the substrate of two competing cyclases: lycopene ε-cyclase (LCYe) and lycopene β-cyclase (LCYb). When acting together on the two ends of the molecule, lycopene ε-cyclase and lycopene β-cyclase form α-carotene. The action of lycopene ε-cyclase alone forms δ- and ε-carotene. The action of lycopene β-cyclase alone forms γ- and β-carotene. As such, a microorganism of the present disclosure may be genetically engineered to express any combination of lycopene ε-cyclase and lycopene β-cyclase to produce one or a combination of carotenes. For instance, a microorganism of the present disclosure may be genetically engineered to produce β-carotene, γ-carotene, β-carotene, α-carotene, or ε-carotene. Alternatively, a microorganism may be genetically engineered to produce a combination of β-carotene, γ-carotene, β-carotene, α-carotene, or ε-carotene. As such, a microorganism of the present disclosure may be genetically engineered to express lycopene ε-cyclase, lycopene β-cyclase, or a combination of lycopene ε-cyclase and lycopene β-cyclase.

Preferably, a microorganism of the present disclosure is genetically engineered to express lycopene ε-cyclase to produce ε-carotene. A microorganism may preferably be genetically engineered to express lycopene ε-cyclase of *Lactuca sativa*. A microorganism may more preferably be genetically engineered to express lycopene ε-cyclase of *Lactuca sativa* having SEQ ID NO: 87. When a recombinant microorganism is *Y. lipolytica*, lycopene ε-cyclase of *Lactuca sativa* having SEQ ID NO: 87 is encoded by nucleic acid SEQ ID NO: 84 codon-optimized for expression in *Y. lipolytica*.

Also preferred, a recombinant microorganism of the present disclosure is genetically engineered to express lycopene β-cyclase to produce β-carotene. A recombinant microorganism may preferably express lycopene cyclase of the bifunctional lycopene cyclase/phytoene synthase of *M. circinelloides* (carRP). More preferably, a recombinant microorganism expresses lycopene cyclase of the wild-type bifunctional lycopene cyclase/phytoene synthase of *M. circinelloides* (carRP). When a recombinant microorganism is *Y. lipolytica*, lycopene cyclase of the wild-type bifunctional lycopene cyclase/phytoene synthase of *M. circinelloides* is encoded by nucleic acid SEQ ID NO: 63 codon-optimized for expression in *Y. lipolytica*.

When a microorganism is *E. coli*, a recombinant *E. coli* capable of producing ε- or β-carotene may express geranylgeranyl pyrophosphate synthase, phytoene synthase, phytoene desaturase, and phytoene cyclase. Preferably, a recombinant *E. coli* capable of producing β-carotene expresses geranylgeranyl pyrophosphate synthase, phytoene synthase, phytoene desaturase, and lycopene cyclase of *Erwinia herbicola*. Also preferred is a recombinant *E. coli* capable of producing ε-carotene expresses geranylgeranyl pyrophosphate synthase, phytoene synthase, and phytoene desaturase of *Erwinia herbicola*, and lycopene ε-cyclase of *Lactuca sativa* (SEQ ID NO:86).

It will be recognized that the genetic modifications described herein for producing the various carotenoids may be in addition to any or all of the genetic modifications described above for producing lycopene.

C. Carotene Derivatives

A microorganism of the present disclosure may be genetically engineered to produce or increase production of a carotenoid derivative. In particular, a microorganism may be genetically engineered to produce or increase production of the α- and β-ionone cleavage products of carotenes. Preferably, a microorganism is genetically engineered to produce or increase production of the α-ionone cleavage product of carotenes.

The cleavage reactions of carotenes are generally catalyzed by a class of non-heme iron enzymes known as carotenoid cleavage dioxygenases (CCDs; FIG. 4). As such, a microorganism of the present disclosure is genetically engineered to express any combination of one or more of CCD1 and CCD4 to produce α-ionone or β-ionone. Irrespective of the carotenoid cleavage dioxygenase used in a microorganism of the disclosure, it is preferred that the CCD is not able to cleave acyclic carotenoids, such as lycopene and phytoene.

FIG. 4 also shows that cleavage of γ-carotene and β-carotene by a CCD enzyme produces β-ionone, cleavage of α-carotene by a CCD enzyme produces a combination of α-ionone and β-ionone, and cleavage of ε-carotene by a CCD enzyme produces α-ionone. As such, depending on the intended use of a recombinant microorganism in producing α-ionone, β-ionone, or a combination of α-ionone and β-ionone, the microorganism may further be genetically engineered to produce the carotene that may be cleaved into α-ionone, β-ionone, or a combination of α-ionone and β-ionone.

A microorganism may further genetically engineered to produce ε-carotene that is cleaved into α-ionone. When the intended use of a microorganism of the present disclosure is genetically engineered to produce α-ionone, but not β-ionone, the microorganism may further be engineered to inhibit expression of lycopene β-cyclase, or is naturally not able to express lycopene β-cyclase, to prevent production of β-ionone.

Alternatively, a microorganism may further be genetically engineered to produce β-carotene that is cleaved into β-ionone. When the intended use of a microorganism of the present disclosure is genetically engineered to produce β-ionone, but not α-ionone, the microorganism may further be engineered to inhibit expression of lycopene α-cyclase, or is naturally not able to express lycopene α-cyclase, to prevent production of α-ionone.

CCDs constitute a large enzyme family and typically exhibit a high degree of region-specificity to the double bond positions of their carotenoid substrates. The CCD enzymes are grouped in CCD1, CCD4, CCD7, and CCD8 classes and can cleave multiple carotenoid substrates while producing various volatile compounds. In general, CCD1 and CCD4 are able to cleave the 5,6 (5,6'), 7,8 (7',8') and 9,10 (9',10') double bonds of a wide range of carotenoids. In comparison, CCD7 and CCD8 are involved in the biosynthesis of strigolactone growth regulators. The 9', 10' bond of β-carotene is cleaved by CCD7, yielding β-ionone ($C_{13}$) and 10'-apo-β-carotenal. The latter compound is subsequently cleaved and cyclized by CCD8 into a bioactive strigolactone precursor named carlactone. α-ionone is the proposed reaction product of the cleavage of the 9,10 (9'10') double bond of α-carotene. As such, a microorganism of the present disclosure may be genetically engineered to express any combination of one or more carotenoid cleavage dioxygenase enzymes. Preferably, a microorganism of the present disclosure is genetically engineered to express any combination of one or more carotenoid cleavage dioxygenase enzymes capable of cleaving a carotenoid to produce α-ionone, β-ionone, or a combination of α-ionone and β-ionone.

Preferably, a microorganism of the present disclosure is genetically engineered to express CCD1 from *Daucus carota* (SEQ ID NO: 88). When a recombinant microorganism is *Y. lipolytica*, CCD1 from *Daucus carota* is encoded by nucleic acid SEQ ID NO: 89 codon-optimized for expression in *Y. lipolytica*. When a recombinant microorganism is *S. cerevisiae*, CCD1 from *Daucus carota* is encoded by nucleic acid SEQ ID NO: 90 codon-optimized for expression in *S. cerevisiae*.

It will further be recognized that the genetic modifications described herein for producing the various carotenoid derivatives may be in addition to any or all of the genetic modifications described above for producing lycopene and carotenoids.

(c) Genetic Engineering

According to the present invention, carotenoid production in a host organism may be adjusted by expressing or modifying the expression or activity of one or more proteins involved in carotenoid biosynthesis. Such modification may involve introduction of at least one nucleic acid construct comprising one or more nucleic acid sequences encoding heterologous carotenoid biosynthesis polypeptides into the host microorganism. Alternatively or additionally, modifications may be made to the expression or activity of one or more endogenous or heterologous carotenoid biosynthesis polypeptides. Given the considerable conservation of components of the carotenoid biosynthesis polypeptides, it is expected that heterologous carotenoid biosynthesis polypeptides will often function even in significantly divergent organisms. Furthermore, should it be desirable to introduce more than one heterologous carotenoid biosynthesis polypeptide, in many cases polypeptides from different source organisms will function together.

At least one nucleic acid construct encoding a plurality of different heterologous carotenoid biosynthesis polypeptides may be introduced into the same host cell. A plurality of different heterologous carotenoid biosynthesis polypeptides may comprise only polypeptides from the same source organism (e.g., two or more sequences of, or sequences derived from the same source organism). Alternatively, a plurality of different heterologous carotenoid biosynthesis polypeptides may comprise polypeptides independently selected from different source organisms (e.g., two or more sequences of, or sequences derived from, at least two independent source organisms).

Those of ordinary skill in the art will appreciate that the selection of a particular microorganism for use in accordance with the present invention will also affect, for example, the selection of expression sequences utilized with any heterologous polypeptide to be introduced into the cell, and will also influence various aspects of culture conditions, etc. Much is known about the different gene regulatory requirements, protein targeting sequence requirements, and cultivation requirements of different host cells to be utilized in accordance with the present invention (see, for example, with respect to *Yarrowia*, Barth et al. *FEMS, Microbiol Rev.* 19:219, 1997; Madzak et al., *J. Biotechnol.* 109:63, 2004; see, for example, with respect to *Xanthophyllomyces*, Verdoes et al., *Appl Environ Microbiol* 69: 3728-38, 2003; Visser et al. *FEMS Yeast Res* 4: 221-31, 2003; Martinez et al., *Antonie Van Leeuwenhoek.* 73(2):147-53, 1998; Kim et al. *Appl Environ Microbiol.* 64(5):1947-9, 1998; Wery et al., *Gene* 184(1):89-97, 1997; see, for example, with respect to *Saccharomyces*, Guthrie and Fink, *Methods in Enzymology* 194:1-933, 1991). In certain aspects, for example, targeting sequences of the host cell (or closely related analogs) may be useful to include for directing heterologous proteins to subcellular localization. Thus, such useful targeting sequences can be added to heterologous sequences for proper intracellular localization of activity. In other aspects (e.g., addition of mitochondrial targeting sequences), heterologous targeting sequences may be eliminated or altered in the selected heterologous sequences (e.g., alteration or removal of source organism plant chloroplast targeting sequences).

As described above, a recombinant microorganism of the present disclosure comprises at least one nucleic acid construct comprising one or more nucleic acid sequences encoding a carotenoid biosynthesis enzyme. A nucleic acid sequence of the present disclosure may be operably linked to one or more expression control sequences for expressing a carotenoid biosynthesis enzyme. "Expression control sequences" are regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, that have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

A recombinant microorganism may synthesize one, two, three, four, five, or more carotenoid biosynthetic enzymes. A one or more nucleic acid encoding any of the enzymes disclosed herein may be chromosomally integrated, or may be expressed on an extrachromosomal vector. Suitable vectors are known in the art. Similarly, methods of chromosomally inserting a nucleic acid are known in the art. For additional details, see the Examples.

A large number of promoters, including constitutive, promoters for high-level expression (overexpression), inducible and repressible promoters, from a variety of different sources are well known in the art. Representative sources include, for example, viral, mammalian, insect, plant, yeast, and bacterial cell types, and suitable promoters from these sources are readily available, or can be made synthetically based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction).

Non-limiting examples of suitable promoters may include an intron-containing transcriptional elongation factor TEF promoter (TEFIN), GPAT (glycerol-3-phosphate o-acyl transferase), YAT1 (ammonium transporter), EXP1 (export protein), and GPD (glyceraldehyde-3-phosphate dehydrogenase), FBA1 (fructose 1,6-bisphosphate aldolase), GPM1 (phosphoglycerate mutase), FBA1IN (FBA1 containing an intron), the GAL promoters of yeast, and hp4d (Four tandem copies of upstream activator sequences (UAS1B) fragment from pXPR2 and a minimal pLEU2 fragment. Preferably, a promoter suitable for overexpression of proteins is used to overexpress one or more carotenoid biosynthesis enzymes of the disclosure. Non-limiting examples of suitable promoters for overexpression of proteins include intron-containing transcriptional elongation factor TEF promoter (TEFIN) and EXP1 (export protein).

A nucleic acid may be modified for high-level expression (overexpression) in a microorganism of the invention. As used herein, "modified" refers to an alteration of a nucleic acid sequence that results in a change in the level of transcription of a nucleic acid sequence, or that results in a change in the level of synthesis of an encoded protein. For instance, the term "modify" may refer to altering the start codon of a nucleic acid sequence. Modify may also refer to fusing two enzymes to increase the activity of each enzyme. Alternatively, modify may refer to optimizing the codons of the nucleic acid sequence to alter the level of translation of the mRNA. For instance, non-A rich codons initially after the start codon of a nucleic acid sequence may not maximize translation of the corresponding mRNA. Modify may refer to altering the GC content of the nucleic acid sequence to change the level of translation of the corresponding mRNA. Additionally, modify may refer to alterations in the DNA sequence of a gene so that the transcribed mRNA is stabilized with a reduced rate of degradation but still able to specify a protein of the original amino acid sequence. Alternatively, a nucleic acid may be optimized by altering the nucleic acid such that the ability of the encoded protein to form efficient enzyme complexes is affected. Preferably, the codons of the nucleic acid sequence are altered so as to mimic the codons in genes encoding highly synthesized proteins of a particular organism.

A nucleic acid of the invention may further comprise at least one marker. Generally speaking, a marker encodes a product that the host cell cannot make, such that the cell acquires resistance to a specific compound, is able to survive under specific conditions, or is otherwise differentiable from cells that do not carry the marker. Markers may be positive or negative markers. A nucleic acid of the invention may comprise both a positive marker and a negative marker. The marker may code for an antibiotic resistance factor, or a nutritional requirement. Additionally, fluorescent proteins may be used as visually identifiable markers. Generally speaking, markers may be present during construction of the strains, but are typically removed from the final constructs. Proteins can also be marked by adding a sequence such as FLAG, HA, His tag, that can be recognized by a monoclonal antibody using immunological methods.

Nucleic acid constructs of the invention may also comprise flanking sequences. The phrase "flanking sequence" as used herein, refers to a nucleic acid sequence homologous to a chromosomal sequence. A construct comprising a flanking sequence on either side of a construct (i.e., a left flanking sequence and a right flanking sequence) may homologously recombine with the homologous chromosome, thereby integrating the construct between the flanking sequences into the chromosome. Generally speaking, flanking sequences may be of variable length. Preferably, the flanking sequences may be between about 300 and about 500 bp. Alternatively, the left flanking sequence and the right flanking sequence may be substantially the same length. For more details, see the Examples.

As such, the present disclosure provides in part a nucleic acid construct comprising a nucleic acid sequence encoding a lycopene cyclase enzyme selected from lycopene ε-cyclase and lycopene β-cyclase, and a nucleic acid sequence encoding a carotenoid cleavage dioxygenase enzyme. The lycopene ε-cyclase enzyme may be from *Lactuca sativa*. The lycopene β-cyclase enzyme is lycopene cyclase of a bifunctional lycopene cyclase/phytoene synthase of *M. circinelloides*. Alternatively, the lycopene β-cyclase enzyme may be lycopene cyclase of bifunctional lycopene cyclase/phytoene synthase of *Phycomyces blakesleeanus*. The carotenoid cleavage dioxygenase enzyme may be CCD1 from *Daucus carota*. The nucleic acid construct may further comprise a nucleic acid sequence encoding a phytoene dehydrogenase enzyme. The phytoene dehydrogenase enzyme may be from *Mucor circinelloides*. The phytoene dehydrogenase enzyme may also be from *Phycomyces blakesleeanus*. The nucleic acid construct may further comprise a nucleic acid sequence encoding a phytoene synthase enzyme. The phytoene synthase enzyme may be phytoene synthase of lycopene cyclase/phytoene synthase from *Mucor circinelloides*. Alternatively, the phytoene synthase enzyme may be phytoene synthase of lycopene cyclase/phytoene synthase from *Phy-*

*comyces blakesleeanus*. When the phytoene synthase enzyme is phytoene synthase of lycopene cyclase/phytoene synthase enzyme, the lycopene cyclase/phytoene synthase enzyme is modified to decrease lycopene cyclase activity. The phytoene synthase enzyme may also be from *Erwinia herbicola*. The nucleic acid construct may further comprise a nucleic acid sequence encoding a phytoene desaturase enzyme from *Erwinia herbicola*. The nucleic acid construct may further comprise a nucleic acid sequence encoding a lycopene cyclase enzyme from *Erwinia herbicola*. The nucleic acid construct may further comprise a nucleic acid sequence encoding a farnesyl diphosphate synthase enzyme. The nucleic acid construct may further comprise a nucleic acid sequence encoding a farnesyl diphosphate synthase enzyme from *Yarrowia lipolytica*. The nucleic acid construct may further comprise a nucleic acid sequence encoding a farnesyl diphosphate synthase enzyme from *S. cerevisiae*. The nucleic acid construct may further comprise a nucleic acid sequence encoding a geranylgeranyl diphosphate synthase enzyme. The nucleic acid construct may further comprise a nucleic acid sequence encoding a geranylgeranyl diphosphate synthase enzyme from *Yarrowia lipolytica*. The nucleic acid construct may further comprise a nucleic acid sequence encoding a geranylgeranyl diphosphate synthase enzyme from *Xanthophyllomyces dendrorhous*. The nucleic acid construct may further comprise a nucleic acid sequence encoding a geranylgeranyl diphosphate synthase enzyme from *S. cerevisiae*. The nucleic acid construct may further comprise a nucleic acid sequence encoding a geranylgeranyl diphosphate synthase enzyme from *Erwinia herbicola*. The nucleic acid construct may further comprise a nucleic acid sequence encoding a farnesyl diphosphate synthase enzyme and a geranylgeranyl diphosphate synthase enzyme. The nucleic acid construct may further comprise a nucleic acid sequence encoding a geranylgeranyl diphosphate synthase enzyme fused in frame with a farnesyl diphosphate synthase enzyme. The nucleic acid construct may further comprise a nucleic acid sequence encoding an acetyl-coA acetyltransferase enzyme. The nucleic acid construct may further comprise a nucleic acid sequence encoding a 3-hydroxy-3-methyl-glutaryl-CoA reductase enzyme. The nucleic acid construct may further comprise a nucleic acid sequence encoding a truncated 3-hydroxy-3-methyl-glutaryl-CoA reductase enzyme. The nucleic acid construct may further comprise a nucleic acid sequence encoding an isopentenyl diphosphate isomerase. The nucleic acid construct may further comprise a nucleic acid sequence encoding a geranyl pyrophosphate synthase enzyme.

The nucleic acid sequences are operably linked to one or more expression control sequences. One or more of the nucleic acid sequences may be operably linked to an intron-containing transcriptional elongation factor TEF promoter (TEFIN). Alternatively, one or more of the nucleic acid sequences may be operably linked to an export protein promoter (EXP1). The nucleic acid construct may be codon-optimized for expression in a heterologous microorganism.

A nucleic acid construct of the invention may comprise a plasmid suitable for use in a microorganism of choice. Such a plasmid may contain multiple cloning sites for ease in manipulating nucleic acid sequences. Numerous suitable plasmids are known in the art.

II. Methods

In another aspect, the present disclosure provides a method of producing carotenoids and carotenoid derivatives. Preferably, a method of the present disclosure is capable of producing lycopene, carotene, and ionones. Most preferred are methods of producing α-ionone and β-ionone.

A method of the disclosure comprises cultivating a recombinant microorganism expressing carotenoid biosynthesis enzymes under conditions sufficient for the production of the carotenoid or carotenoid derivative. A recombinant microorganism may be as described in Section I above.

As discussed above, production of carotenoids and carotenoid derivatives in a recombinant microorganism of the present disclosure generally comprises cultivating the relevant organism under conditions sufficient to accumulate a carotenoid or carotenoid derivative, harvesting the modified microorganism, and isolating the carotenoid or carotenoid microorganism from the harvested microorganism.

Methods of cultivating a microorganism are well known in the art and may be similar to conventional fermentation methods. As will be appreciated by a skilled artisan, the culture conditions sufficient to accumulate a carotenoid or carotenoid derivative can and will vary depending on the specific microorganism host cell or strain and the carotenoid or carotenoid derivative produced by the microorganism. A recombinant microorganism may be cultured in a medium comprising a carbon source, a nitrogen source, and minerals, and if necessary, appropriate amounts of nutrients which the microorganism requires for growth. As the carbon source, saccharides such as glucose, fructose, sucrose, molasses and starch hydrolysate, organic acids such as fumaric acid, citric acid and succinic acid, or alcohol such as ethanol and glycerol may be used. As the nitrogen source, various ammonium salts such as ammonia and ammonium sulfate, other nitrogen compounds such as amines, a natural nitrogen source such as peptone, soybean-hydrolysate, or digested fermentative microorganism may be used. As minerals, potassium monophosphate, magnesium sulfate, sodium chloride, ferrous sulfate, manganese sulfate, calcium chloride, and the like may be used. As vitamins, thiamine, yeast extract, and the like, may be used. The pH of the medium may be between about 5 and about 9. When the microorganism comprises a mutation that limits the production of an essential nutrient, the medium may be supplemented with the essential nutrient to maintain growth of the microorganism.

When the microorganism is *Y. lipolytica* or *S. cerevisiae*, the recombinant microorganism may be cultivated in YPD medium (10 g/L yeast extract, 20 g/L peptone and 20 g/L glucose) to produce a carotenoid or carotenoid derivative of the disclosure. *Y. lipolytica* or *S. cerevisiae* may also be cultivated in SD-dropout medium containing 1.7 g/L yeast nitrogen base without amino acids and ammonium sulphate, 20 g/L D-glucose, 5 g/L ammonium sulphate, 2 g/L yeast synthetic drop-out medium supplements and other nutrients that may vary depending on the nutrient requirement of the *Y. lipolytica* or *S. cerevisiae* strain.

Various temperature and duration of cultivation may also be used and will vary depending on the specific microorganism host cell or strain, the carotenoid or carotenoid derivative produced by the microorganism, and its culture conditions. The cultivation may be performed under aerobic conditions, such as by shaking and/or stirring with aeration. When the microorganism is *Y. lipolytica* or *S. cerevisiae*, a recombinant microorganism may be cultivated at a temperature of about 20 to about 40° C., preferably at a temperature of about 20, 21, 22, 23, 24, 25, 26, 27, 28, 29, 30, 31, 32, 33, 34, 35, 36, 37, 38, 39, and about 40° C. More preferably, a recombinant *Y. lipolytica* or *S. cerevisiae* may be cultivated at a temperature of about 28° C.

A recombinant microorganism of the present disclosure may be cultivated for about 1, 2, 3, 4, 5, 6, 7, 8, 9, 10 or more days before isolating carotenoids and carotenoid derivatives.

Preferably, when a recombinant microorganism is *Y. lipolytica*, the recombinant microorganism is cultivated for about 1, 2, or 3 days before isolating carotenoids and carotenoid derivatives, preferably, 1 day.

When a recombinant microorganism is *E. coli*, the microorganism may be cultivated in LB medium in a shaker at a temperature of about 25 to about 40° C., preferably at a temperature of about 37° C. If carotenogenic enzymes expressed in *E. coli* are under the control of an inducible promoter, the enzymes may be induced at a temperature of about 25 to 35° C., preferably at a temperature of about 30° C.

Methods and systems for isolating carotenoids and carotenoid derivatives have been established for a wide variety of carotenoids and carotenoid derivatives (see, for example, Perrut M, Ind Eng Chem Res, 39: 4531-4535, 2000, the disclosure of which is incorporated herein in its entirety). In brief, cells are typically recovered from culture, often by spray drying, filtering or centrifugation. In some instances, cells are homogenized and then subjected to supercritical liquid extraction or solvent extraction (e.g., with solvents such as chloroform, hexane, methylene chloride, methanol, isopropanol, ethyl acetate, etc.) using conventional techniques.

Given the sensitivity of carotenoids generally to oxidation, the disclosure may employ oxidative stabilizers (e.g., tocopherols, vitamin C; ethoxyquin; vitamin E, BHT, BHA, TBHQ, etc, or combinations thereof) during and/or after carotenoid isolation. Alternatively or additionally, microencapsulation, for example with proteins, may be employed to add a physical barrier to oxidation and/or to improve handling (see, for example, U.S. Patent Application 2004/0191365).

In general, a recombinant microorganism accumulate carotenoids and carotenoid de rivatives to levels that are greater than at least about 0.1% of the dry weight of the cells. The total carotenoid accumulation in a recombinant microorganism may be to a level at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20% or more of the total dry weight of the cells.

Definitions

When introducing elements of the present disclosure, the articles "a," "an," "the," and "said" are intended to mean that there are one or more of the elements. The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The terms "about" or "approximately" means within an acceptable error range for the particular value as determined by one of ordinary skill in the art, which will depend in part on how the value is measured or determined, i.e., the limitations of the measurement system. For example, "about" can mean within 1 or 2 standard deviations, from the mean value. Alternatively, "about" can mean plus or minus a range of up to 20%, preferably up to 10%, more preferably up to 5%.

The term "carotenogenic modification", as used herein, refers to a modification of a host organism that adjusts production of one or more carotenoids or their derivatives, as described herein. For example, a carotenogenic modification may increase the production level of one or more carotenoids or their derivatives, and/or may alter relative production levels of different carotenoids or their derivatives. In principle, an inventive carotenogenic modification may be any chemical, physiological, genetic, or other modification that appropriately alters production of one or more carotenoids or their derivatives in a host organism produced by that organism as compared with the level produced in an otherwise identical organism not subject to the same modification. However, the carotenogenic modification may comprise a genetic modification, typically resulting in increased production of one or more selected carotenoids or their derivatives.

The term "carotenogenic polypeptide", as used herein, refers to any polypeptide that is involved in the process of producing carotenoids or their derivatives in a cell, and may include polypeptides that are involved in processes other than carotenoid production but whose activities affect the extent or level of production of one or more carotenoids or their derivatives, for example by scavenging a substrate or reactant utilized by a carotenoid polypeptide that is directly involved in carotenoid production. Carotenogenic polypeptides include isoprenoid biosynthesis polypeptides, carotenoid biosynthesis polypeptides, and isoprenoid biosynthesis competitor polypeptides.

The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls.

The term "isoprenoid biosynthesis polypeptide" refers to any polypeptide that is involved in the synthesis of isoprenoids. For example, as discussed herein, acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase, are all involved in the mevalonate pathway for isoprenoid biosynthesis. Each of these proteins is also an isoprenoid biosynthesis polypeptide for purposes of the present invention.

The "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP, the "mevalonate pathway" and the "non-mevalonate pathway".

As used herein, the terms "cell," "cells," "cell line," "host cell," and "host cells," are used interchangeably and encompass a variety of yeast or fungal strains that may be utilized as host strains to produce carotenoids and their derivatives. Thus, the terms "transformants" and "transfectants" include the primary subject cell and cell lines derived therefrom without regard for the number of transfers.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantified by Northern blot hybridization, ribonuclease RNA protection, in situ hybridization to cellular RNA or by PCR. Proteins encoded by a selected sequence can be quantified by various methods including, but not limited to, e.g., ELISA, Western blotting, radioimmunoassays, immunoprecipitation, assaying for the biological activity of the protein, or by immunostaining of the protein followed by FACS analysis.

The term "expression cassette" refers to a nucleic acid comprising the coding sequence of a selected gene and regulatory sequences preceding (expression control sequences) and following (non-coding sequences) the coding sequence that are required for expression of the selected gene product. Thus, an expression cassette is typically composed of: (1) a promoter sequence; (2) a coding sequence (i.e., ORF); and (3) a 3' untranslated region (i.e., a terminator) that, in eukaryotes, usually contains a polyadenylation site. The expression cassette(s) is usually included within a vector to facilitate cloning and transformation. Different expression cassettes can be transformed into different organisms including bacteria, yeast, plants and mammalian cells, as long as the correct regulatory sequences are used for each host.

"Expression control sequences" are regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, that have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

A "gene" is a sequence of nucleotides which code for a functional gene product. Generally, a gene product is a functional protein. However, a gene product can also be another type of molecule in a cell, such as RNA (e.g., a tRNA or an rRNA). A gene may also comprise expression control sequences (i.e., non-coding) as well as coding sequences and introns. The transcribed region of the gene may also include untranslated regions including introns, a 5'-untranslated region (5'-UTR) and a 3'-untranslated region (3'-UTR).

The term "heterologous" refers to a nucleic acid or protein which has been introduced into an organism (such as a plant, animal, or prokaryotic cell), or a nucleic acid molecule (such as chromosome, vector, or nucleic acid construct), which is derived from another source, or which is from the same source but is located in a different (i.e., non-native) context.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention.

To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., (1987) Cell, 50:667). Such proteins (and their encoding nucleic acids) have sequence homology, as reflected by their sequence similarity, whether in terms of percent identity or by the presence of specific residues or motifs and conserved positions.

As used herein, the term "increase" or the related terms "increased", "enhance" or "enhanced" refers to a statistically significant increase. For the avoidance of doubt, the terms generally refer to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control value.

The term "isolated," when used to describe a protein or nucleic acid, means that the material has been identified and separated and/or recovered from a component of its natural environment. Contaminant components of its natural environment are materials that would typically interfere with research, diagnostic or therapeutic uses for the protein or nucleic acid, and may include enzymes, hormones, and other proteinaceous or non-proteinaceous solutes. The protein or nucleic acid may be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated proteins and nucleic acids will be prepared by at least one purification step.

The terms "operably linked", "operatively linked," or "operatively coupled" as used interchangeably herein, refer to the positioning of two or more nucleotide sequences or sequence elements in a manner which permits them to function in their intended manner. A nucleic acid molecule according to the invention may include one or more DNA elements capable of opening chromatin and/or maintaining chromatin in an open state operably linked to a nucleotide sequence encoding a recombinant protein. A nucleic acid molecule may additionally include one or more DNA or RNA nucleotide sequences chosen from: (a) a nucleotide sequence capable of increasing translation; (b) a nucleotide sequence capable of increasing secretion of the recombinant protein outside a cell; (c) a nucleotide sequence capable of increasing the mRNA stability, and (d) a nucleotide sequence capable of binding a trans-acting factor to modulate transcription or translation, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein, it is not necessarily contiguous with it. Operable linking of various nucleotide sequences is accomplished by recombinant methods well known in the art, e.g., using PCR methodology, by ligation at suitable restriction sites, or by annealing. Synthetic oligonucleotide linkers or adaptors can be used in accord with conventional practice if suitable restriction sites are not present.

The terms "polynucleotide," "nucleotide sequence" and "nucleic acid" are used interchangeably herein, and refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, a polynucleotide includes not only naturally occurring bases such as A, T, U, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Prokaryotic promoters contain Shine-Dalgarno sequences in addition to the −10 and −35 consensus sequences.

The term "transformation" or "transfection" refers to the transfer of one or more nucleic acid molecules into a host cell or organism. Methods of introducing nucleic acid molecules into host cells include, for instance, calcium phosphate transfection, DEAE-dextran mediated transfection, microinjection, cationic lipid-mediated transfection, electroporation, scrape loading, ballistic introduction, or infection with viruses or other infectious agents.

"Transformed", "transduced", or "transgenic" in the context of a cell, refers to a host cell or organism into which a recombinant or heterologous nucleic acid molecule (e.g., one or more DNA constructs or RNA, or siRNA counterparts) has been introduced. The nucleic acid molecule can be stably expressed (i.e. maintained in a functional form in the cell for longer than about three months) or non-stably maintained in a functional form in the cell for less than three months (i.e. is transiently expressed). For example, "transformed," "transformant," and "transgenic" cells have been through the transformation process and contain foreign nucleic acid. The term "untransformed" refers to cells that have not been through the transformation process.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Buchanan et al., Biochemistry and Molecular Biology of Plants, Courier Companies, USA, 2000; Miki and Iyer, Plant Metabolism, $2^{nd}$ Ed. D. T. Dennis, D H Turpin, D D Lefebrve, D G Layzell (eds) Addison Wesly, Langgmans Ltd. London (1997); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein.

The publications discussed above are provided solely for their disclosure before the filing date of the present application. Nothing herein is to be construed as an admission that the invention is not entitled to antedate such disclosure by virtue of prior invention.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Construction of Y. lipolytica Expression Vectors

NEB Turbo Competent E. coli (F' proA+B+ laclq ΔlacZM15/fhuA2 Δ(lac-proAB) glnV galK16 galE15 R(zgb-210::Tn10) Tet$^S$ endA1 thi-1 Δ(hsdS-mcrB)5) for cloning was purchased from New England Biolabs (Ipswich, Mass.). Cells were grown on LB medium with carbenicillin (100 mg/L) for plasmid selection. The Yarrowia lipolytica strain, CLIB138 (MatB, leu2-35, lys5-12, ura3-18, xpr2LYS5), was purchased from CIRM-Levures (Thiverval-grignon, France) and used as host cells in the following exemplifications. The strain Po1g of Yarrowia lipolytica (MatA, leu2-270, ura3-302::URA3, xpr2-332, axp-2) was used for genomic DNA extraction.

All DNA manipulations were performed according to standard procedures. Restriction enzymes and T4 DNA Ligase were purchased from New England Biolabs (Ipswich, Mass.). All PCR amplification and cloning reactions were performed using Phusion® High-Fidelity DNA Polymerase from New England Biolabs (Ipswich, Mass.).

Genomic DNA of Y. lipolytica Po1g was extracted as follows: a single colony was isolated and grown in 3 ml liquid YPD culture overnight at 30° C., then pelleted by centrifugation. The resulting pellet was washed once with 1 ml sterile water and suspended in 500 μl of lysis buffer (100 mM Tris, pH 8.0, 50 mM EDTA, 1% SDS). Cells were disrupted by adding 200 μl of glass beads (425-600 μm diameter) and vortexing for 2 minutes. The liquid phase was recovered into a fresh tube, and 275 μl of 7 M Ammonium acetate (pH 7.0) was added. The sample was incubated for 5 minutes at 65° C., put on ice for 5 min, then extracted with 500 μl of chloroform, vortexed, centrifuged for 5 min. The resulting supernatant was transferred to a new tube, and nucleic acid was precipitated with 1 ml of isopropanol and incubated at room temperature for 5 min. DNA was pelleted with centrifugation (15,000 g) for 5 minutes. Supernatant was then removed, and the pellet washed once with 70% ethanol, then dried and dissolved in 200 μl of water. 1 μl of the DNA was used for PCR.

Y. lipolytica expression vector was constructed as follows: Marker gene orotidine 5'-phosphate decarboxylase (URA3) containing LOXP site was obtained by PCR amplification with primers LOXP-URA3-NdeI-sphIF (SEQ ID NO: 1) and LOXP-URA3-AflIII-EcoRIR (SEQ ID NO: 2) using Y. lipolytica genomic DNA as template. The resulting 1.2 kb URA3 fragment was cloned into the NdeI and AflII restriction sites of the pUC57 vector to generate the YAL-URA3 construct.

A TEF promoter-XPR2 terminator cassette was constructed by stitching two nucleic acid fragments by PCR amplification. First, a 406 bp nucleic acid fragment comprising the TEF promoter was amplified using Y. lipolytica genomic DNA as a template, and the primers TEF-EcoRI-PmeIF (SEQ ID NO: 3) and TEF::XPR2-R (SEQ ID NO: 4). A 134 pb nucleic acid fragment comprising the XPR2 terminator was also amplified using Y. lipolytica genomic DNA as a template, and the primers TEF::XPR2-F (SEQ ID NO: 5) and XPR2-AflIII-SalIR (SEQ ID NO: 6). The amplified fragments comprising the TEFpromoter and the XPR2 terminator were then stitched by combining the amplified fragments, and using the combined amplified fragments as templates for amplification of the TEF-XPR2 cassette with oligonucleotide primers TEF-EcoRI-PmeIF (SEQ ID NO: 3) and XPR2-AflIII-SalIR (SEQ ID NO: 6). The cassette was then cloned into the EcoRI/AflIII restriction sites of the YAL-URA3 vector to generate the YAL-URA3-TEF-XPR2 construct.

A nucleic acid fragment comprising the LEU2 marker gene encoding 3-isopropylmalate dehydrogenase activity was amplified from the pYLEX1 vector with primers LEU2-SphIF (SEQ ID NO: 7) and LEU2-PmeIR (SEQ ID NO: 8). The LEU2 fragment was then cloned into the SphI and PmeI restriction sites of the YAL-URA3-TEF-XPR2 vector to yield the YAL-LEU2-TEF-XPR2 vector. The Y. lipolytica autonomously replicating sequence 18 (ARS18) was amplified using primers ARS18-NdeIF (SEQ ID NO: 9) and ARS19-SphIR (SEQ ID NO: 10), and cloned into the NdeI/SphI sites of the YAL-LEU2-TEF-XPR2 vector, to generate vector YAL-LEU2-TEF-XPR2-ARS. The Cre Recombinase gene (Cre) was amplified by primers Cre-BclIF (SEQ ID NO: 11) and Cre-XmaIR (SEQ ID NO: 12) using Cre-LOXP mice genomic DNA as template, then digested with BclI and XmaIR, and cloned into BamHI/XmaI sites of YAL-LEU2-TEF-XPR2-ARS vector, to yield the YAL-LEU2-Cre vector.

A 572 bp nucleic acid fragment comprising the recombination site rDNA1 and a 822 bp nucleic acid fragment comprising the recombination site rDAN2 were amplified using primers rDNA-NdeI-NotI-SacIIF (SEQ ID NO: 13) and rDNA-SphIR (SEQ ID NO: 14), and rDNA-SalI-ASCIIF (SEQ ID NO: 15) and rDNA-AflIII-NotI-SacIIR (SEQ ID NO: 16), respectively, using Y. lipolytica genomic DNA as a template. The nucleic acid fragment comprising rDNA1 was then cloned into the NdeI/SphI restriction sites of the YAL-URA3-TEF-XPR2 construct to yield YAL-rDNA1-URA3-TEF-XPR2, and the nucleic acid fragment comprising rDNA2 was cloned into the SalI and AflII restriction sites of YAL-rDNA1-URA3-TEF-XPR2 to form the YAL-rDNA-URA3-TEF-XPR2 construct.

Example 2: Production of Lycopene in Genetically Modified Y. lipolytica Expressing Phytoene Dehydrogenase (carB) and Modified Lycopene Cyclase/Phytoene Synthase (carRP*)

The Y. lipolytica strains were grown at 28° C. in a shaker at 250 rpm in YPD medium (10 g/L yeast extract, 20 g/L peptone and 20 g/L glucose) or in SD-dropout medium containing 1.7 g/L yeast nitrogen base without amino acids & ammonium sulphate, 20 g/L D-glucose, 5 g/L ammonium sulphate, 2 g/L yeast synthetic drop-out medium supplements (US biological, Swampscott, Mass.). Depending on the nutrient requirement of the *Y. lipolytica* strain, 20 mg/L histidine, 100 mg/L leucine, 50 mg/L tryptophan, or 40 mg/L uracil were added into the growth medium. Culture plates comprised 20 g/L agar.

Transformation of *Y. lipolytica*

Carrier DNA was purchased from Clontech, Inc. (Mountain View, Calif.) and boiled 5 minutes before using. Transformation of *Y. lipolytica* was performed using a modified *Yarrowia* transformation method (Chen, 1997). In brief, a single *Yarrowia* colony was spread on a YPD or SD-dropout selection plate and incubated for 12-16 hrs at room temperature. Cells were scraped from the surface of the agar and dispersed in 100 μl transformation buffer (45% PEG 4000, 100 mM lithium acetate pH 6.0, 100 mM DTT). Then about 20-100 ng plasmid (1-5 μl) and 25 μg single-stranded carrier DNA (10 mg/ml) were added. The transformation solution was thoroughly mixed and incubated at 39° C. for 60 min. The mixture was then spread on a SD-dropout selective plate and incubated at 28° C. The transformed colonies appeared after 24 hrs.

Generation of a Modified Bifunctional Enzyme Lycopene Cyclase/Phytoene Synthase (carRP*)

A nucleotide fragment (SEQ ID NO: 62) encoding a bifunctional lycopene cyclase/phytoene synthase (SEQ ID NO: 64) from *Mucor circinelloides* (carRP) codon-optimized for expression in *Y. lipolytica* was generated. The codon-optimized *Mucor circinelloides* carRP (SEQ ID NO: 63) was referred to as OptcarRP-. OptcarRP was cloned into the pUC57 vector to generate the pUC57-carRP plasmid. Site-directed mutagenesis was then used to introduce two mutations into OptcarRP.

The 78$^{th}$ amino acid was mutated from lysine (K) to glutamate (E) using primers OptcarRP-78F (SEQ ID NO: 35) and OptcarRP-78R (SEQ ID NO: 36). In short, a PCR reaction mixture containing (10 μl) composed of Phusion HF buffer containing 20 ng pUC57-carRP template, 200 μM dNTPS, 0.5 μM forward primers, 0.5 μM reverse primers, and 0.1 μl polymerase was prepared. The PCR was performed by denaturing at 98° C. for 10 sec, annealing at 60° C. for 30 sec, and followed by elongation at 72 C for 2 min for 22 cycles. The PCR product was digested with 1 μl DpnI at 37° C. for 5 hrs to remove the template plasmid, and an aliquot of (2 μl) digested products was added to 50 μl NEB Turbo competent cells and incubated on ice for 15 min. The cell/nucleic acid mixture was then heat shocked at 42° C. for 30 sec, followed by incubation on ice for 1 min. Then, 250 μl LB medium was added and the cells were incubated at 37° C. for 1 hr, then spread on LB agar plates containing carbenicillin (100 mg/l). The identity of the mutation was confirmed by sequencing, and the resulting construct was referred to as pUC57-carRP-78. The proline (P) at amino acid 216 of mutant OptcarRP in pUC57-carRP-78 plasmid was also mutated to serine (S) using the method described here and primers OptcarRP-216F (SEQ ID NO: 37) and OptcarRP-216R (SEQ ID NO: 38). The double mutated gene was named carRP* (SEQ ID NO: 66) and encoded a lycopene cyclase/phytoene synthase enzyme comprising the K78E and P216S amino acid changes (SEQ ID NO: 69) to reduce lycopene cyclase activity.

Construction of Lycopene Biosynthetic Pathway Plasmids

The pathway of lycopene biosynthesis was reconstituted in *Y. lipolytica* by over-expressing three enzymes: phytoene dehydrogenase (SEQ ID NO: 61) from the carB gene of *Mucor circinelloides* (SEQ ID NO: 58), modified bifunctional lycopene cyclase/phytoene synthase (SEQ ID NO: 69) (carRP*) from *Mucor circinelloides* (SEQ ID NO: 65), and geranylgeranyl diphosphate synthase (GGPPS) from *Y. lipolytica* (SEQ ID NO: 71). Codon-optimized nucleic acid fragments encoding OptcarB (SEQ ID NO: 59) and OptcarRP* (SEQ ID NO: 66) were cloned and expressed in *Y. lipolytica*. The three genes, OptcarB (SEQ ID NO: 59), OptcaRP* (SEQ ID NO: 66), and YLGGPPS (SEQ ID NO: 70), flanked with BamHI and AvrII, were amplified by PCR using the primers, optcarB-BamHIF (SEQ ID NO: 17) and OptcarB-AvrIIR (SEQ ID NO: 18), OptcarRP*-BamHIF (SEQ ID NO: 19) and OptcarRP*-AvrIIR (SEQ ID NO: 20), and YLGGPPS-BamHIF (SEQ ID NO: 21) and YLGGPPS-AvrIIR (SEQ ID NO: 23), respectively. The three nucleotide fragments were then digested with BamHI/AvrII and ligated to the BamHI/AvrII-digested YAL-rDNA-URA3-TEF-XPR2 vector to form the plasmids YAL-rDNA-URA3-TEF-OptcarB, YAL-rDNA-URA3-TEF-OptcarRP*, and YAL-rDNA-URA3-TEF-YLGGPPS, respectively.

TEF-OptcarRP*-XPR2 and TEF-YLGGPPS-XPR2 cassettes were obtained by PCR amplification with primers PromTEF-SalIF (SEQ ID NO: 24) and TermXPR2-ASCIR (SEQ ID NO: 26) and PromTEF-ASCIF (SEQ ID NO: 25) and TermXPR2-ASCIR (SEQ ID NO: 26), respectively. First, the TEF-OptcarRP*-XPR2 was cloned into the SalI/AscI restriction sites of the YAL-rDNA-URA3-TEF-OptcarB vector to generate the YAL-rDNA-URA3-TEF-OptcarB-TEF-OptcarRP* plasmid. Second, YAL-rDNA-URA3-TEF-OptcarB-TEF-OptcarRP* was digested using AscI and treated with Antarctic Phosphatase following the manufacturer's manual (New England Biolabs, Ipswich, Mass.). The amplified AscI-digested TEF-YLGGPPS-XPR2 cassette was then cloned into the AscI-digested YAL-rDNA-URA3-TEF-OptcarB-TEF-OptcarRP* to generate YAL-rDNA-URA3-TEF-OptcarB-TEF-OptcarRP*-TEF-YLGGPPS.

Expression of Lycopene Biosynthetic Pathway Genes and Marker Excision

*Y. lipolytica* CLIB138 was transformed with YAL-rDNA-URA3-TEF-OptcarB-TEF-OptcarRP*-TEF-YLGGPPS that had been linearized with NotI. The Ura+ transformants were identified by colour screening and HPLC analysis. The strain was subsequently transformed with YAL-LEU-Cre for URA3 marker excision. The transformants were then selected for Leu$^+$ phenotypes on YNB SD minus Leucine medium (SD-LEU) plate. Single colonies were grown in 2 ml YPD medium for 24 hrs at 28° C., then 3 μl cells were grown in 3 ml YPD medium for 12 h at 28° C. The YAL-LEU-Cre-transformed cells were then streaked on YPD plates and incubated for 48 hrs at 28° C. The loss of YAL-LEU-Cre and the URA3 marker gene was confirmed on SD plates lacking leucine (SD-LEU), SD minus uracil (SD-URA), and YPD plates. After 24 hrs, pink colonies which didn't grow on both SD-LEU and SD-URA were used for subsequent transformation.

Extraction of Lycopene from *Y. lipolytica*

*Y. lipolytica* cultures were grown in 5 ml YPD medium in 50 ml test tube at 28° C. for 4 days. Cells were harvested by centrifugation at 4000 rpm for 10 min, and then suspended in extraction solution (methyl-t-butyl ether:methanol:ethyl acetate (40:50:10)). Cells were lysed by vortexing for 3 min in the presence of 300 μl glass beads. The extract was collected after centrifugation, and the extraction procedure was repeated three times.

HPLC Analysis of Lycopene

The HPLC analysis of lycopene was carried out using an Alliance 2996 HPLC (Waters) equipped with a 2476 photodiode array detector. Samples were separated by reverse-phase chromatography on a YMC carotenoid column (particle size 5 μm; 250×4.6 mm) isocratically using a mobile phase of methyl-t-butyl ether:methanol:ethyl acetate (40:50:10, v/v/v) at a flow rate of 1.5 ml/min for 35 min. Peaks were measured at a wavelength from 250-600 nm to facilitate the detection of lycopene.

Figure 5A:
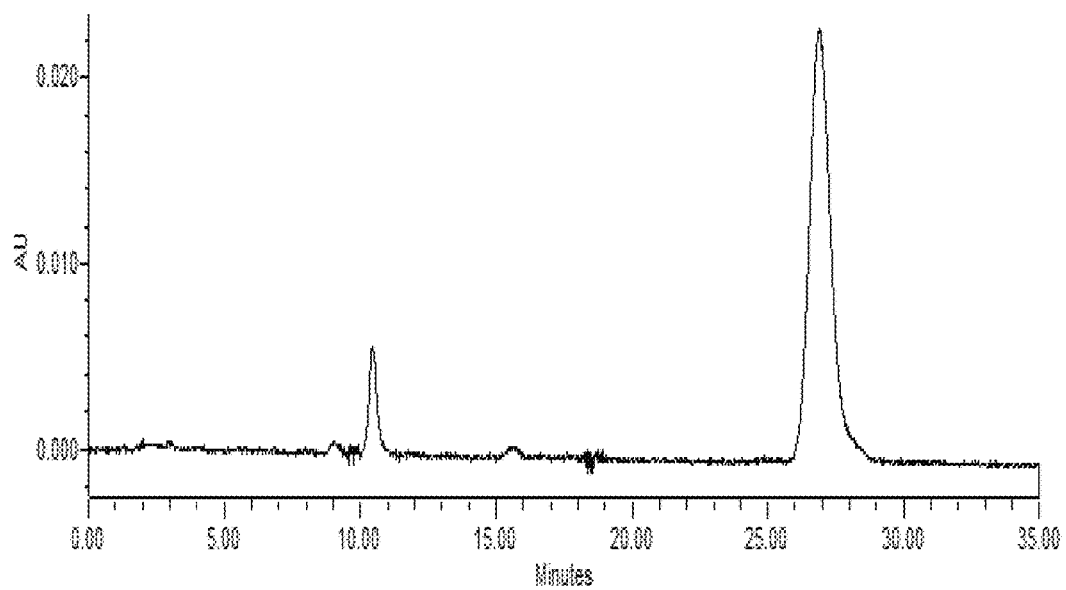
FIG. 5. depicts HPLC profiles of (A) authentic lycopene (>90%; Sigma (Saint Louis, Mo.; CAT No L9879) and (B) extracts from *Y. lipolytica* with exogenous expression of carRP* and carB.
Figure 5B:
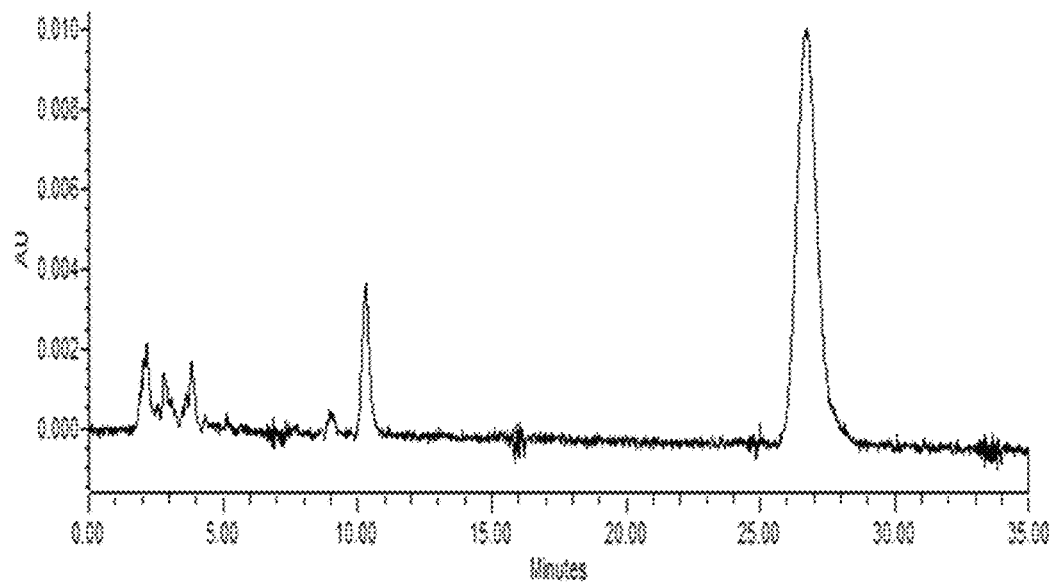
Figure 6A:
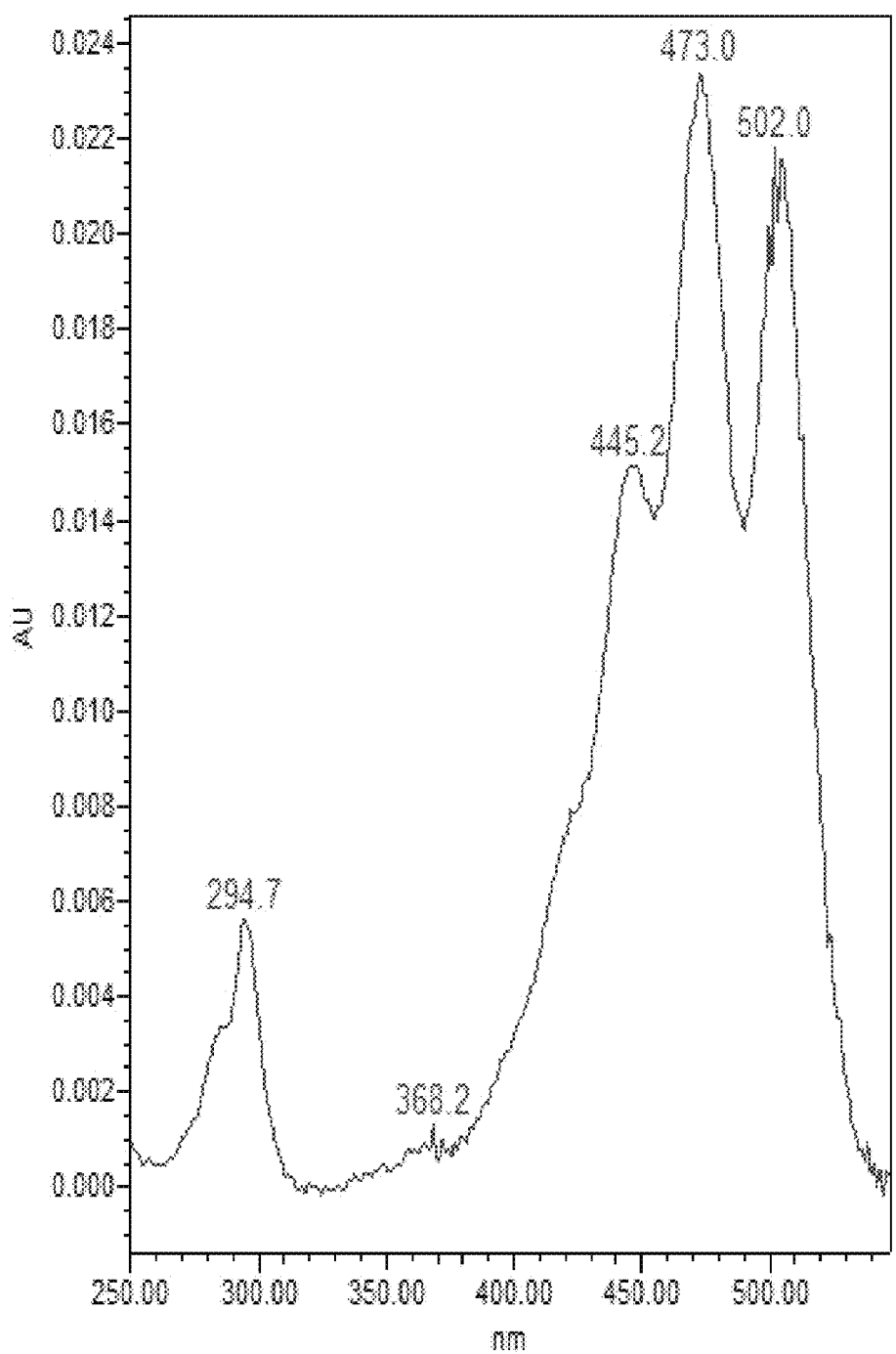
FIG. 6. depicts UV spectra of authentic lycopene (A) and of samples extracted from *Y. lipolytica* (B).
Figure 6B:
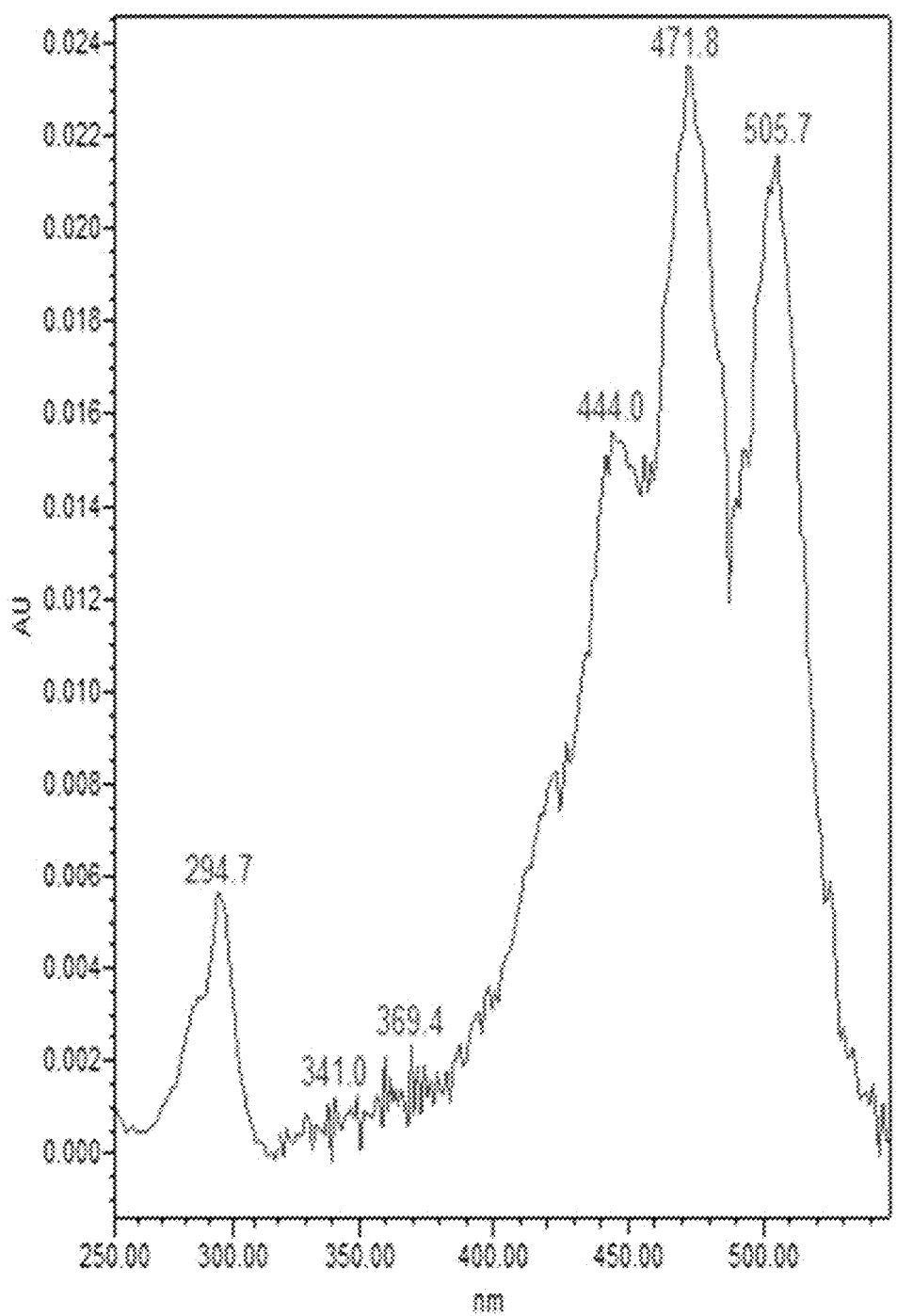

Production of Lycopene in *Y. lipolytica* by Expressing the Modified carRP* Genes For heterologous expressions in *Y. lipolytica*, two foreign biosynthetic genes (carB and carRP*) and the geranylgeranyl diphosphate synthase (GGPPS) from *Y. lipolytica* were cloned into *Y. lipolytica* expression vectors and placed under the control of the strong constitutive promoter TEF as described above. When the three genes were co-expressed in *Y. lipolytica*, colonies that appeared after 24 hrs incubation were pink. After 4 days growth at 28° C. in YPD liquid medium, HPLC analysis revealed a major peak at 26.6 min (FIG. 5). The peak was identified as lycopene by comparison of retention time and UV spectrum with authentic lycopene (FIG. 5, FIG. 6A and FIG. 6B). The lycopene-producing *Y. lipolytica* strain carrying the YAL-rDNA-URA3-TEF-OptcarB-TEF-OptcarRP*-TEF-YLGGPPS construct was designated AI-001.

Marker Excision

The AI-001 strain was transformed with a YAL-LEU-Cre plasmid to excise the selectable marker URA3. The cells were cured of the Cre-expressing plasmid by two successive rounds of culturing in YPD medium, and then selected on SD-LEU and SD-URA medium plate to check the loss of URA3 selection marker and YAL-LEU-Cre plasmid. Transformants were also replica plated on YPD plates for isolation. The results showed that more than 80% of the colonies could not grow in the absence of LEU, and 50% colonies could not grow in the absence of URA. The resulting lycopene-producing strain without URA3 marker gene was designated AI-002.

Example 3: Reconstruction of ε-Carotene Biosynthetic Pathway in *Y. lipolytica*

Expression of Lycopene &Cyclase (LCYe) in Lycopene-Producing *Y. lipolytica*

Carotenoids with two ε-rings are not commonly found in plants. Romaine lettuce (*Lactuca sativa* var. romaine) is one of the few plants known to accumulate large amounts of lactucaxanthin, a carotenoid with two ε-rings. A cDNA encoding lycopene ε-cyclase (SEQ ID NO: 75) from romaine lettuce (LsLCYe; SEQ ID NO: 72) was shown to efficiently convert lycopene into ε-carotene in E. *co/i*. (Cunningham and Gant, 2000).

A lycopene ε-cyclase from *Lactuca sativa* (LsLCYE; SEQ ID NO: 83) codon-optimized for expression in *Y. lipolytica* (SEQ ID NO: 84) was synthesized and amplified using primers LsLCYe-BamHIF (SEQ ID NO: 27) and LsLCYE-KpnIR (SEQ ID NO: 28), and cloned into the BamHI and KpnI restriction sites of the YAL-rDNA-URA3-TEF-XPR2 vector, to generate YAL-rDNA-URA3-TEF-LsLCYE. AI-002 was transformed with the YAL-rDNA-URA3-TEF-LsLCYE plasmid cleaved by NotI, and Ura$^+$ colonies were select on SD-URA plates. The resulting strain was designated AI-003. The URA3 marker was then excised using the same procedure described above for the AI-001 strain. The resulting strain lacking the URA3 marker gene was designated AI-004. After 4 days of growth in liquid YPD medium, cells were extracted and analyzed by HPLC.

Extraction and HPLC Analysis of ε-Carotene

Extraction of ε-carotene was as described above for lycopene extraction, except the extraction solution was a mixture of dichloromethane/methanol at a ratio of 25:75 v/v. Cells were lysed by vortexing for 3 min in the presence of 300 μl glass beads. The extract was collected after centrifugation, and the extraction procedure was repeated three times. The HPLC analysis of ε-carotene was performing the same as described for lycopene analysis, except a flow rate of 0.5 ml/min was used.

Figure 7A:
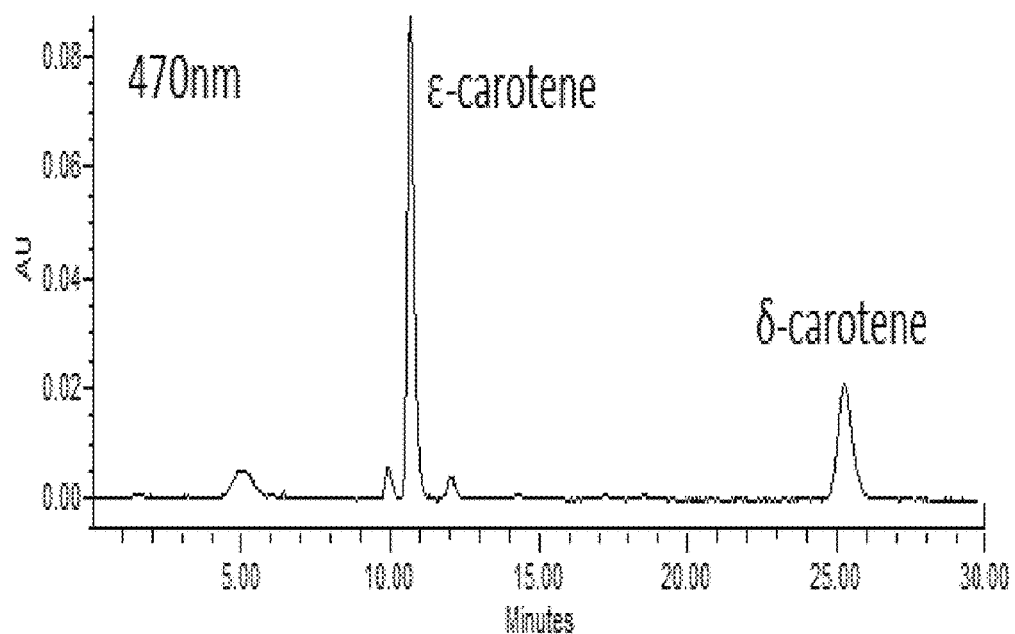
FIG. 7. depicts HPLC profiles showing the production of ε-carotene and β-carotene in lycopene-producing *Y. lipolytica* expressing lycopene ε-cyclase of *Lactuca sativa* (LsLCYe) at different absorption spectra, 470 nm (A), 440 nm (B) and 420 nm (C).
Figure 7B:
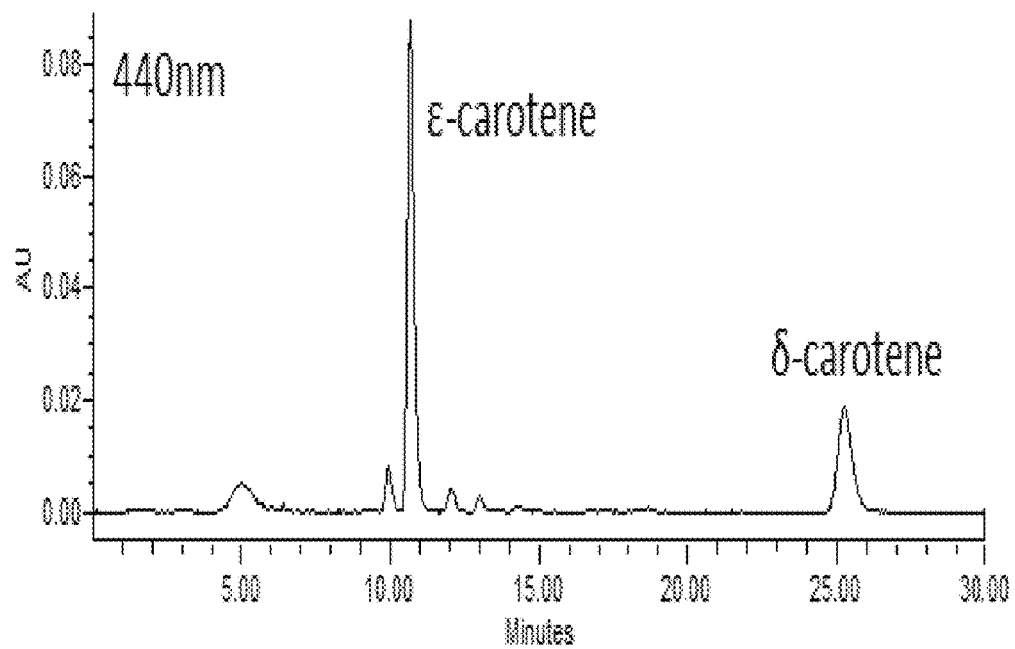
Figure 7C:
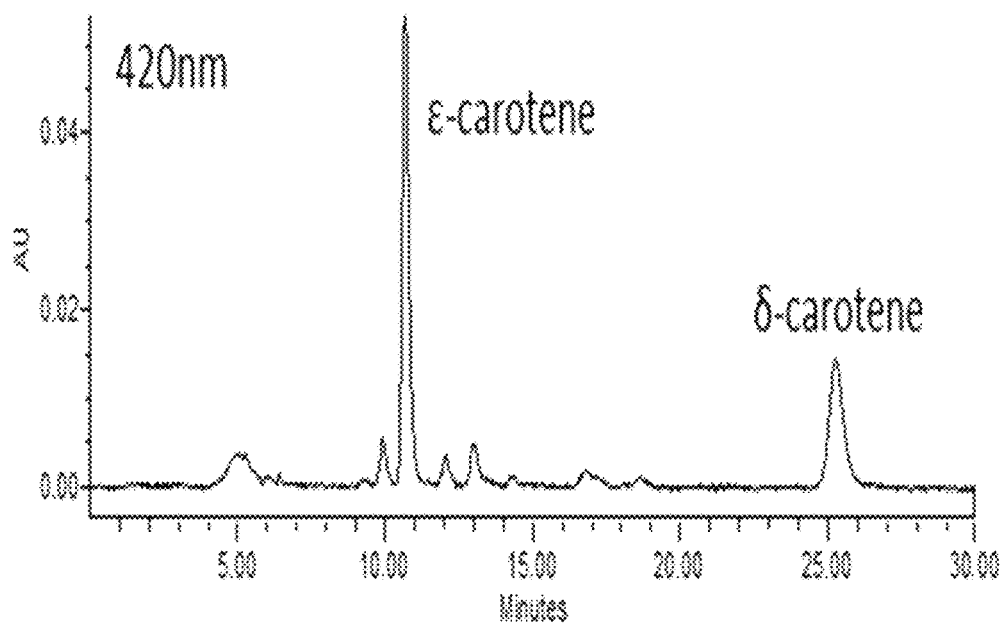
Figure 8A:
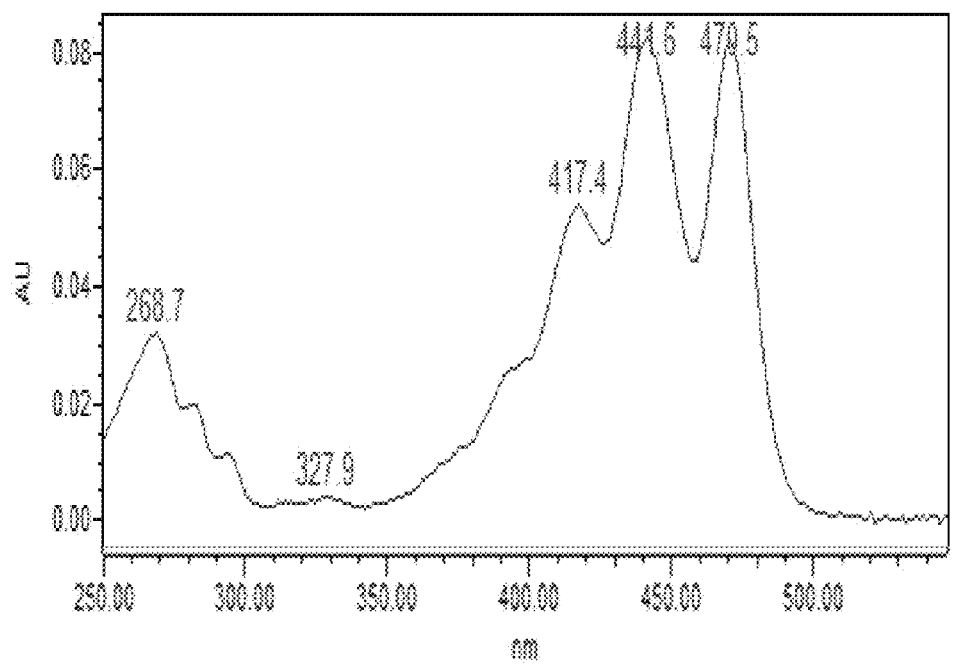
FIG. 8. depicts putative UV absorption spectra of ε-carotene (A), and β-carotene (B).
Figure 8B:
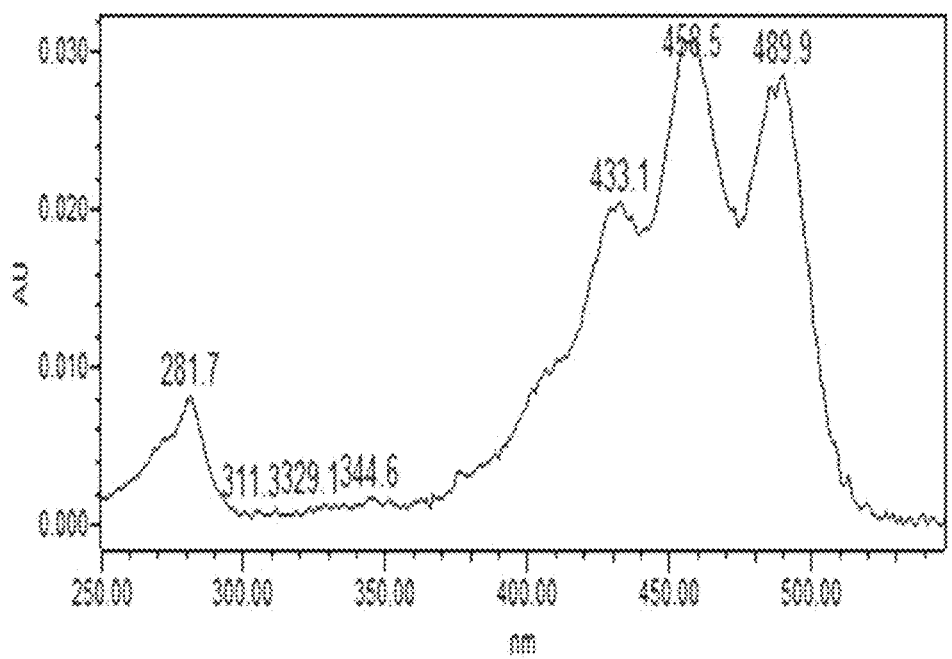

As shown in FIG. 7, FIG. 8A and FIG. 8B, HPLC analysis indicates that strain AI-004 produced two major peaks at 10.9 min and 21.6 min. The two peaks were identified as ε-carotene and β-carotene by comparing retention times and the corresponding spectra with published data. The maximum absorption spectrum of ε-carotene is 417 nm, 441 nm and 470 nm, and β-carotene is 433 nm, 458 nm and 489 nm. In this *Y. lipolytica* system, all lycopene was converted into ε-carotene and β-carotene with the expression of LsLCYe. The ratio of ε-carotene and β-carotene was 8:2 based on area under the peak in expression system.

Example 4: Reconstruction of α-Ionone Biosynthetic Pathway in *Y. lipolytica*

Carotenoids are cleaved into norisoprenoids by carotenoid cleavage dioxygenases (CCDs) targeting different double bounds on the carotenoid backbone. In plants, CCD1 and CCD4 biosynthesize norisoprenoids that contribute to the flavor and aroma of fruits. In order to produce α-ionone in a *Y. lipolytica* system, a CCD must have the following characteristics. First, the CCD must be able to cleave ε-carotene. And second, the CCD should not be able to cleave acyclic carotenoids, such as lycopene and phytoene.

A cDNA (DcCCD1; SEQ ID NO: 88) encoding a protein with carotenoid cleavage dioxygenase activity (SEQ ID NO: 92) and capable of cleaving cyclic carotenes to generate α-ionone and β-ionone was identified in carrots. The recombinant DcCCD1 enzyme also does not cleave non-cyclic carotenoids. In order to demonstrate if the enzyme can cleave ε-carotene, an expression construct comprising a codon-optimized nucleic acid fragment (SEQ ID NO: 89) capable of expressing DcCCD1 (SEQ ID NO: 92) was constructed and introduced into the AI-004 strain engineered to accumulate ε-carotene.

Plasmids Construction and Transformation

A cDNA (SEQ ID NO: 89) encoding a protein with carotenoid cleavage dioxygenase activity from carrot, DcCCD1 (SEQ ID NO: 92), was synthesized, codon-optimized for expression in *Y. lipolytica*, and amplified with primers DcCCD1-BamHIF (SEQ ID NO: 29) and DcCCD1-KpnIR (SEQ ID NO: 30). The amplified product was cloned into the BamHI/KpnI restriction sites of the YAL-rDNA-URA3-TEF-XPR2 vector, to generate YAL-rDNA-URA3-TEF-DcCCD1. The YAL-rDNA-URA3-TEF-DcCCD1 construct was linearized with NotI, and used to transform AI-004. Ura$^+$ colonies were selected on SD-URA plate, and were designated AI-005. Single colonies were selected and were used to inoculate 3 ml YPD liquid medium, and were incubated at 28° C. with shaking at 250 rpm. An overnight culture (1 ml) was used to inoculate 50 ml YPD medium in 250 ml tightly closed rubber stopper flask for HS-SPME.

Solid Phase Microextraction (SPME), HPLC and GC-MS Analysis

The headspace from the overnight cultures above was sampled with a 75-μm Carboxen/Polydimethylsiloxane (CAR/PDMS) fiber for one hour at room temperature (Cat No. 57344-U Sigma, St Louis, Mo., USA). Samples were analyzed on a DB-1 column (12.5 m, 0.2-mm inner diameter, 0.33-μm methyl silicone film coating, from P. J. Cobert, St. Louis, Mo.). After 4 days of growth in liquid YPD medium, a SPME fiber was pulled into the needle sheath and introduced into the flask, and headspace volatiles were allowed to absorb to the fiber at room temperature for 30 min. Subsequently, the SPME device was removed from the flask and inserted into the injection port of the GC system. The volatile compounds collected from the headspace were analyzed using gas chromatography-mass spectrometry (GC-MS; Agilent Technologies 6890N capillary GC and 5973N Network Mass Selection Detector, Foster City, USA) at the Washington University Biomedical Mass Spectrometry Research Resource. Identification of α-ionone was performed by comparison of mass spectra and retention time data to authentic standard and supplemented with GC-MS library.

Figure 9:
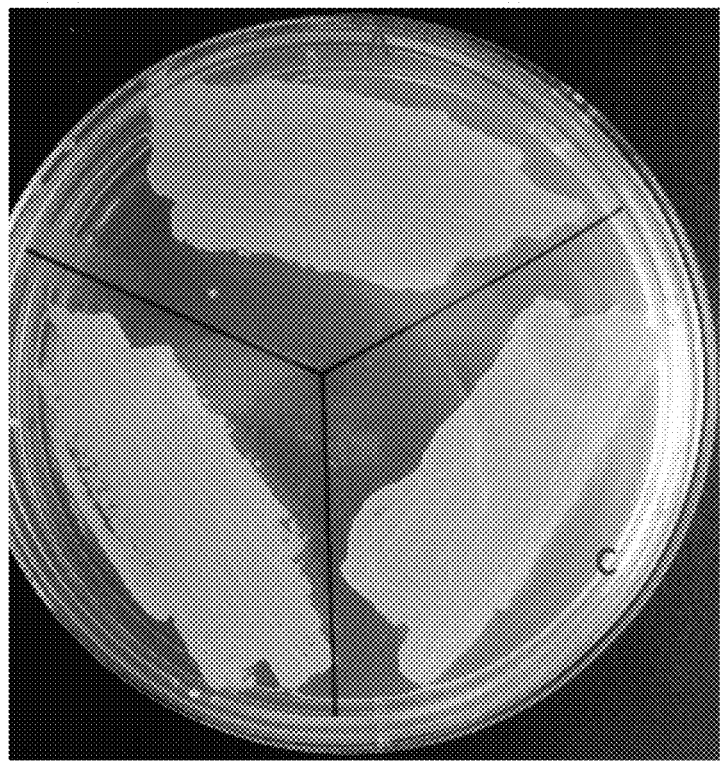
FIG. 9. depicts a photograph depicting the orange coloration of ε-carotene produced in the *Y. lipolytica* strain AI-004. (A) The absence of the orange color in ε-carotene-producing *Y. lipolytica* strain expressing the empty vector. (B) and (C) The disappearance of the orange color in ε-carotene-producing *Y. lipolytica* strain expressing of DcCCD1.
Figure 10A:
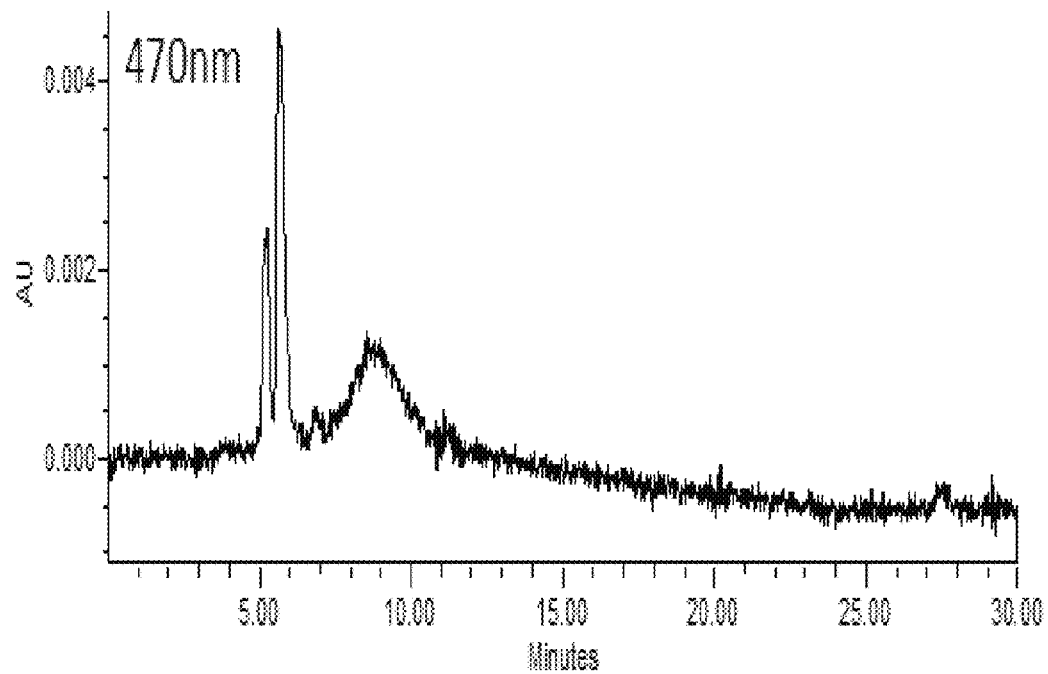
FIG. 10. depicts HPLC profiles showing the production of new compounds (C14 aldehyde) in lycopene-producing *Y. lipolytica* expressing carotenoid cleavage dioxygenases of carrot (DcCCD1) at different absorption spectra, 470 nm (A), 440 nm (B), and 420 nm (C).
Figure 10B:
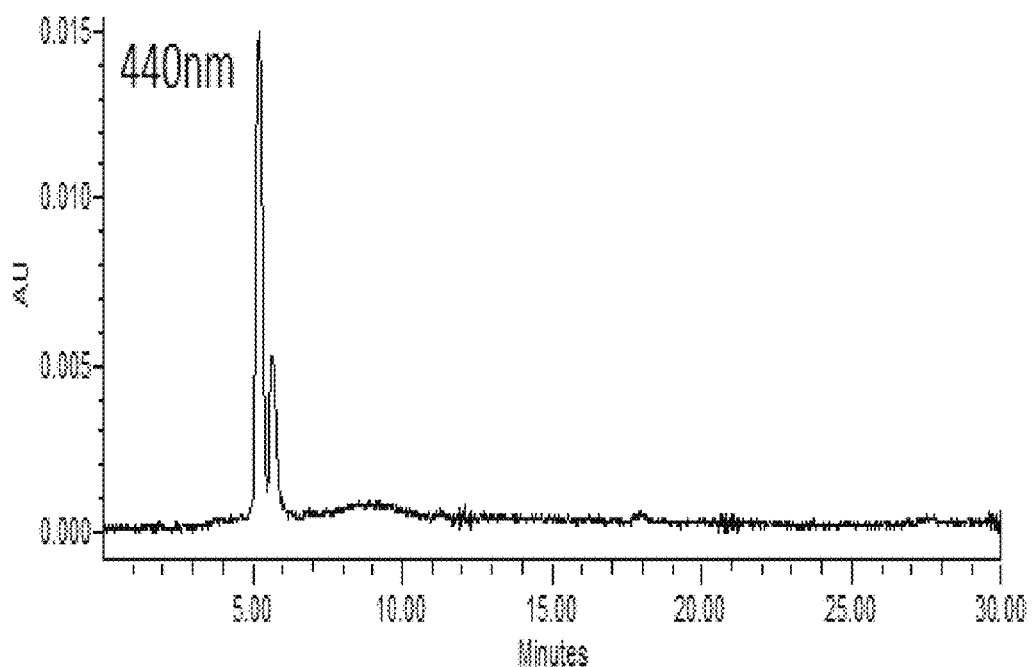
Figure 10C:
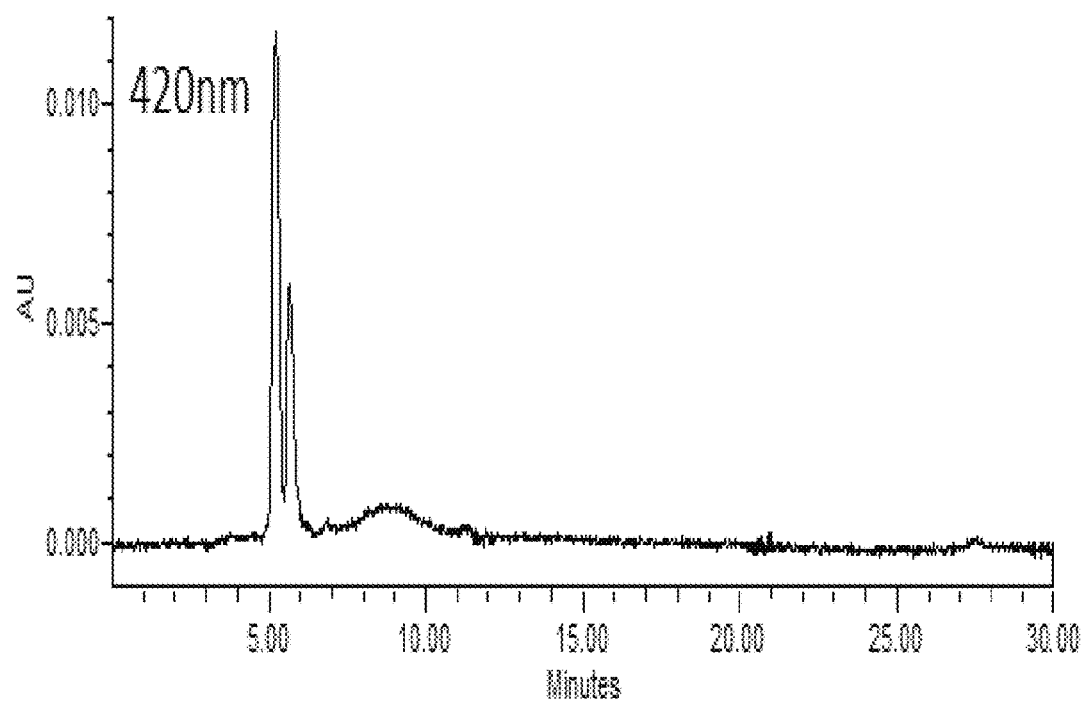
Figure 11:
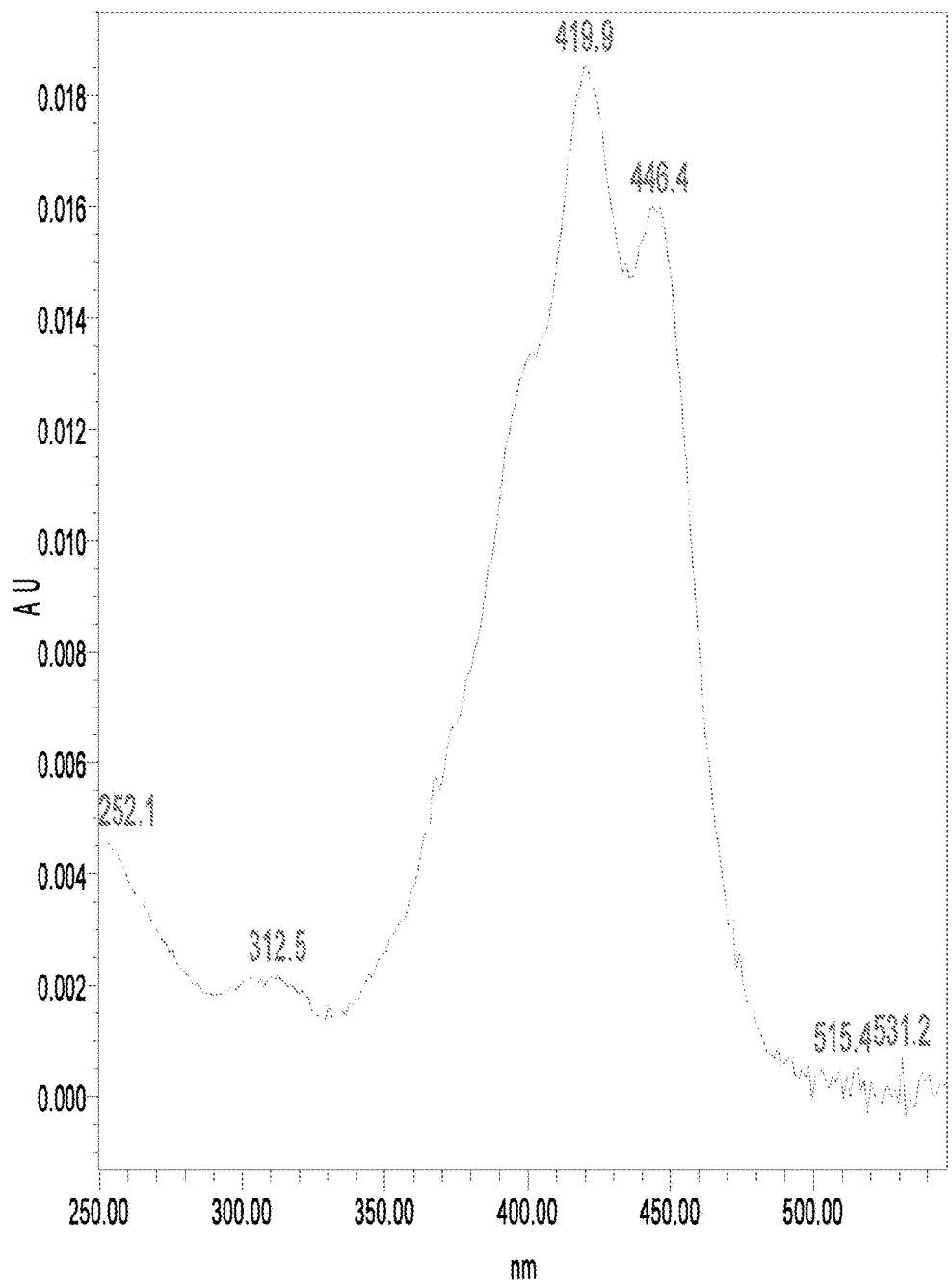
FIG. 11. depicts an HPLC profile of putative UV absorption spectrum of C14 aldehyde.

As shown in FIG. 9, the expression of DcCCD1 led to the expected de-coloration of the orange *Y. lipolytica* strain having accumulated ε-carotene. Loss of color indicated that ε-carotene was metabolized to colorless compounds. HPLC analysis indicated that the ε-carotene and β-carotene peaks were disappeared, and were replaced with two new peaks at 5.2 min and 5.8 min (FIG. 10). The UV spectra of the compound at the 5.2 min peak exhibited absorption maxima at 395 nm, 419 nm and 446 nm (FIG. 11). The spectrum of the peak labeled as C14-dialdehyde (rosafluene dialdehyde) was consistent with the previously described C14-dialdehyde. The peak at 5.8 min is the product of β-carotene cleavage, and due to the instability of C14 dialdehyde, it may be a degradation product of C14-dialdehyde.

Figure 12A:
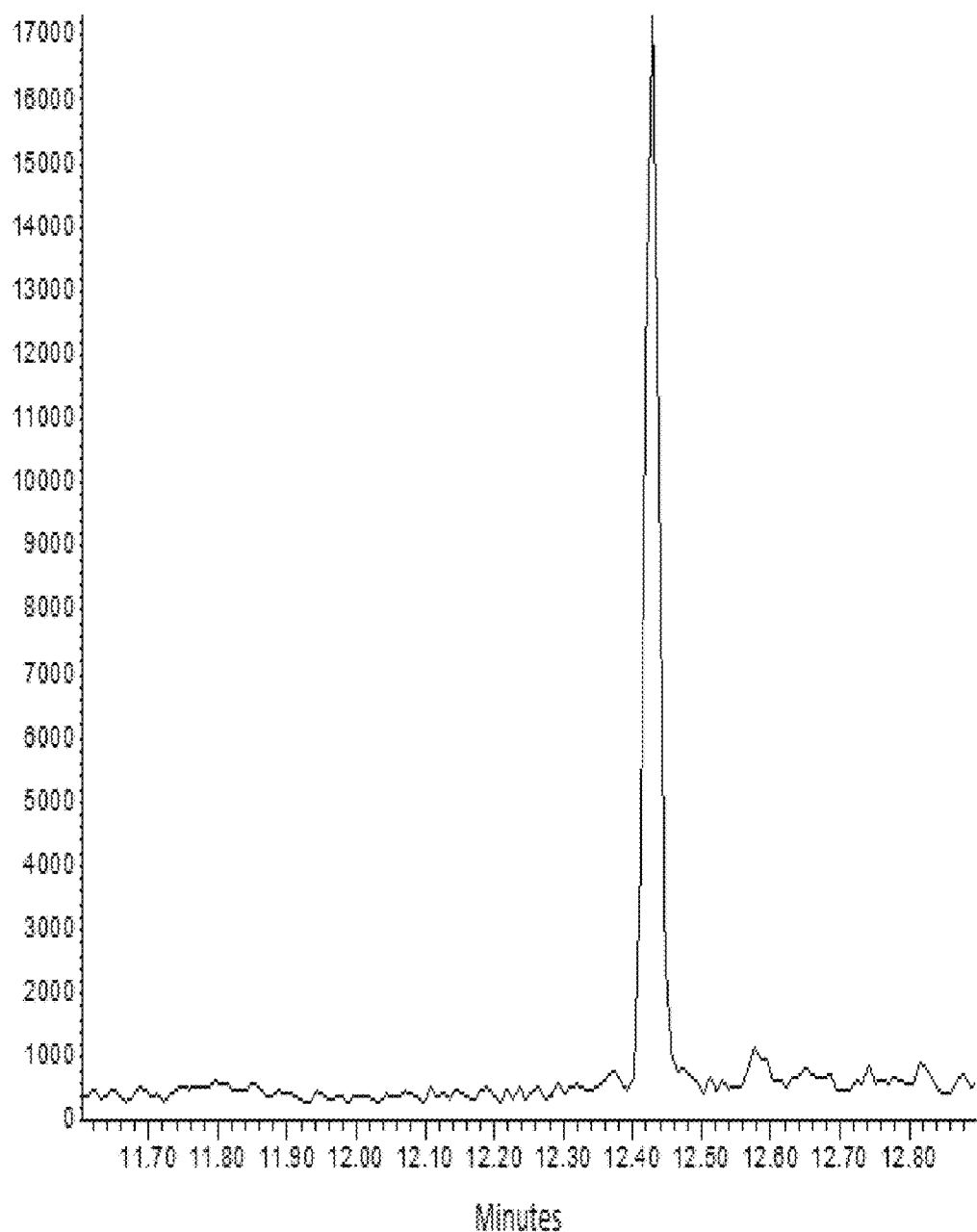
FIG. 12. depicts GC-chromatogram (A) and mass spectrum (B) for SPME-GC-MS analysis of α-ionone formed in *Y. lipolytica* engineered to accumulate ε-carotene with the expression of DcCCD1.
Figure 12B:
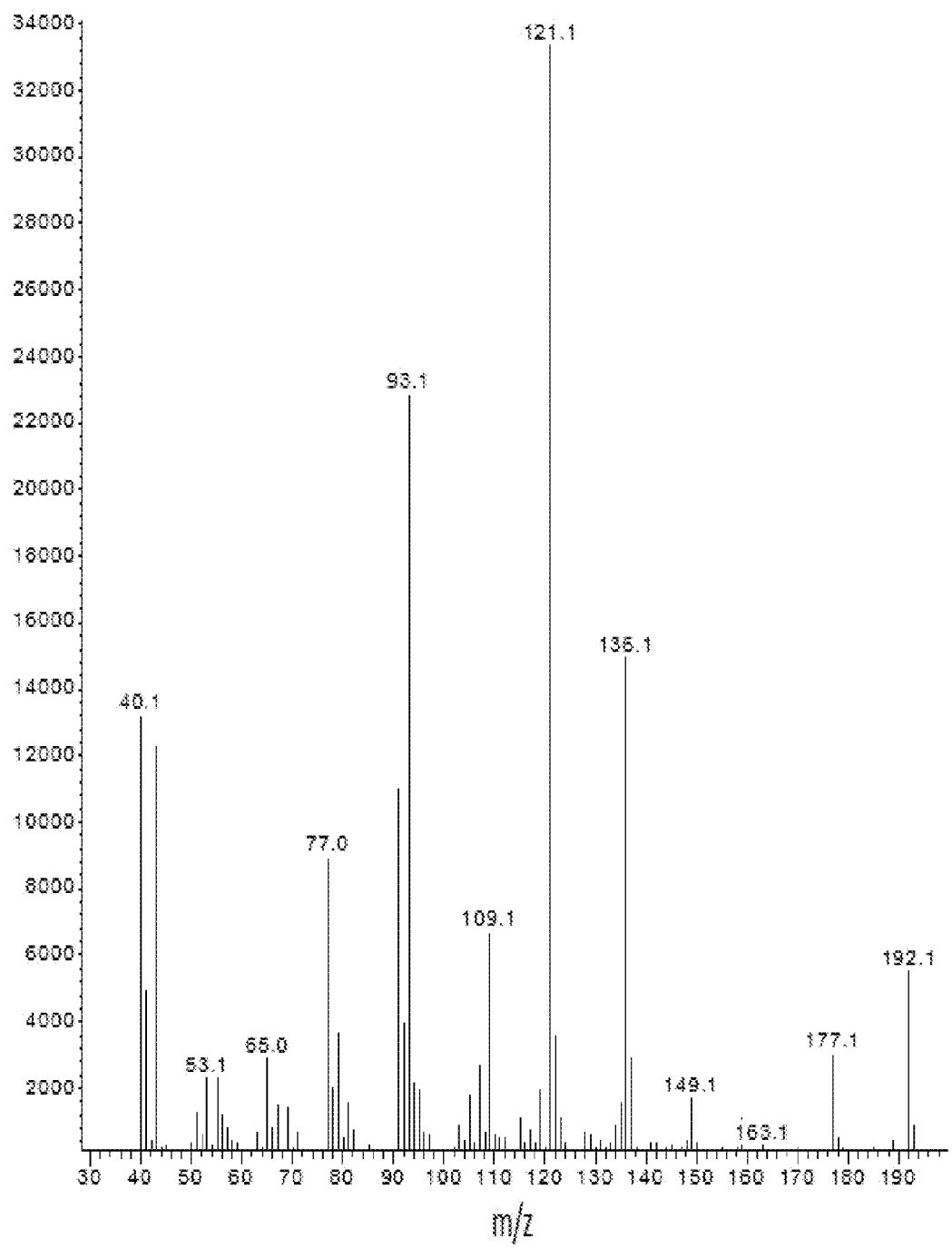
Figure 13A:
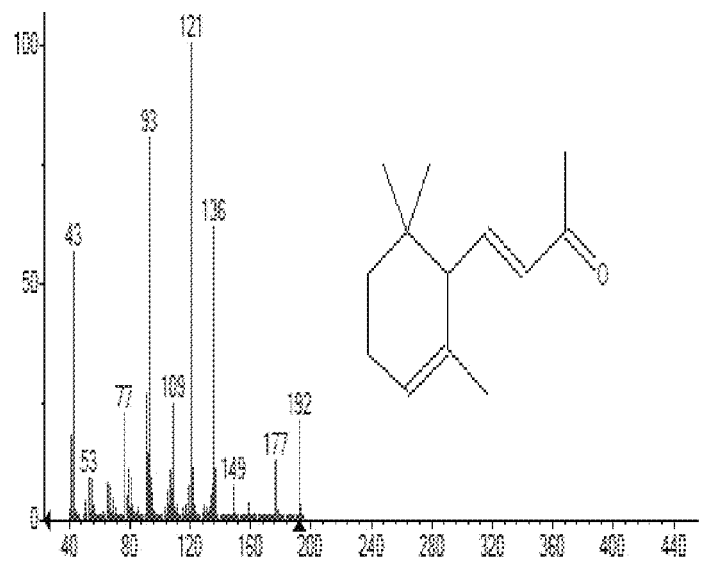
FIG. 13. depicts mass spectra of authentic α-ionone (A), and of compounds in the headspace of *Y. lipolytica* cultures expressing DcCCD1 (B), and the comparison of authentic α-ionone and sample (C).
Figure 13B:
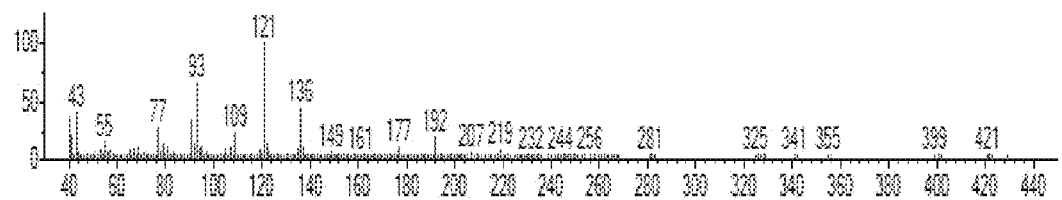
Figure 13C:
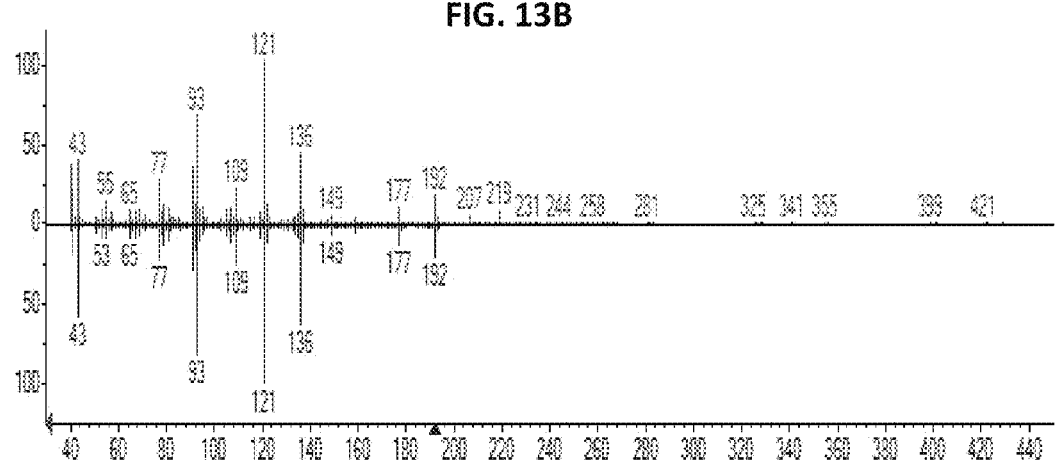

SPME-GC-MS analysis of the headspace of cultures *Y. lipolytica* cultures expressing DcCCD1 revealed the presence of α-ionone (FIG. 12), as evidenced by its retention time and a mass spectrum identical to that of authentic α-ionone (FIG. 13).

Example 5: Intron-Containing TEF Promoter (TEFIN) Increases α-Carotene and Lycopene Production in *Y. lipolytica*

The XPR2 promoter (pXPR2) has been identified as one of the strongest promoters in *Y. lipolytica*. However, its complex regulation hindered its industrial applications. The functional dissection of pXPR2 revealed that one of its upstream activating sequences (UAS) can increase the expression levels of promoters. Four tandem UAS1B copies were fused to a minimal LEU2 promoter to obtain a strong constitutive promoter independent from environmental conditions that normally regulate the XPR2 promoter. Subsequently, a series of strong constitutive promoters for translation elongation factor-1α (pTEF1), ribosomal protein S7 (pRPS7), export protein (pEXP1) were identified. The hrGFP reporter gene was used to evaluate the promoter strengths of endogenous *Y. lipolytica*. The results showed that pEXP1 was the strongest, followed by pTEF1 promoter among seven tested endogenous promoters in yeast synthetic complete medium (YSC) containing 20 g/l glucose. Recently, it has been reported that an intron-containing TEF1 promoter increased gene expression 17-fold over the intron-less TEF1 promoter (for example, see Tai et al., (2013) Metabolic Engineering, 15:1-9).

Construction of Intron-Containing TEF Promoter (TEF1N)

TEFIN promoter was amplified by PCR with primers TEF-EcoRI-PmeIF (SEQ ID NO: 3) and TEFIN-BamHI-SnaBIR (SEQ ID NO: 57), and the amplification product was cloned into the EcoRI/BamHI restriction sites of the YAL-rDNA-URA3-TEF-XPR2 plasmid, resulting in the YAL-rDNA-URA3-TEFIN-XPR2 vector.

For lycopene biosynthesis, three genes, OptcarB, OptcarRP*, and GGPPS, were amplified with primers OptcarB-SnaBIF (SEQ ID NO: 39)/OptcarB-AvrIIR (SEQ ID NO: 18), OptcarRP*-SnaBIF (SEQ ID NO: 40)/OptcarRP*-AvrII (SEQ ID NO: 20), and YLGGPPS-SnaBIF (SEQ ID NO: 22)/YLGGPPS-AvrIIR (SEQ ID NO: 23), respectively. The digested amplification products were then cloned into the SnaBI/AvrII restriction sites of the YAL-rDNA-URA3-TEFIN-XPR2 vector to form the plasmids YAL-rDNA-URA3-TEFIN-OptcarB, YAL-rDNA-URA3-TEFIN-OptcarRP* and YAL-rDNA-URA3-TEFIN-YLGGPPS, respectively. Finally, the three-gene expression cassette vector, YAL-rDNA-URA3-TEFIN-OptcarB-TEFIN-OptcarRP*-TEFIN-YLGGPPS, was generated using the same strategy used for generating the YAL-rDNA-URA3-TEF-OptcarB-TEF-OptcarRP*-TEF-YLGGPPS vector described above. For β-carotene biosynthesis, the same YAL-rDNA-URA3-TEFIN-OptcarB-TEFIN-OptcarRP*-TEFIN-YLGGPPS vector was used, with the exception that the OptcarRP* gene was replaced with the OptcarRP gene. The YAL-rDNA-URA3-TEFIN-OptcarB-TEFIN-OptcarRP*-TEFIN-YLGGPPS for lycopene production and YAL-rDNA-URA3-TEFIN-OptcarB-TEFIN-OptcarRP-TEFIN-YLGGPPS for β-carotene production were transformed into *Y. lipolytica* to generate AI-005 and AI-006 strains, respectively. The two strains with the URA3 marker gene removed were designated AI-007 and AI-008.

Measurement of β-carotene and lycopene using spectroscopy analysis

Relative concentration of β-carotene and lycopene was measured with a simple and rapid UV-Vis spectrometric method using a NanoDrop 2000 UV-Vis spectrophotometer (Thermo Scientific, Wilmington, Del.). The spectra of β-carotene and lycopene were set at 460 nm and 502 nm, respectively.

Figure 14:
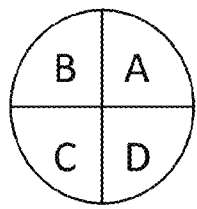
FIG. 14 depicts a photographic image of an agar plate showing that intron-containing promoter and FPPS::GGPPS fusion protein increases lycopene production in *Y. lipolytica*. Strains in the image were grown on the YPD plate for two days. (A) *Y. lipolytica* containing YAL-rDNA-URA3-TEF-OptcarB-TEF-OptcarRP*-TEF-YLGGPPS vector (AI-002); (B) *Y. lipolytica* containing YAL-rDNA-URA3-TEFIN-OptcarB-TEFIN-OptcarRP*-TEFIN-YLGGPPS (AI-007); (C) Strain (AI-007) containing FPPS::GGPPS fusion gene; (D) Strain (AI-002) containing FPPS::GGPPS fusion gene.
Figure 14:
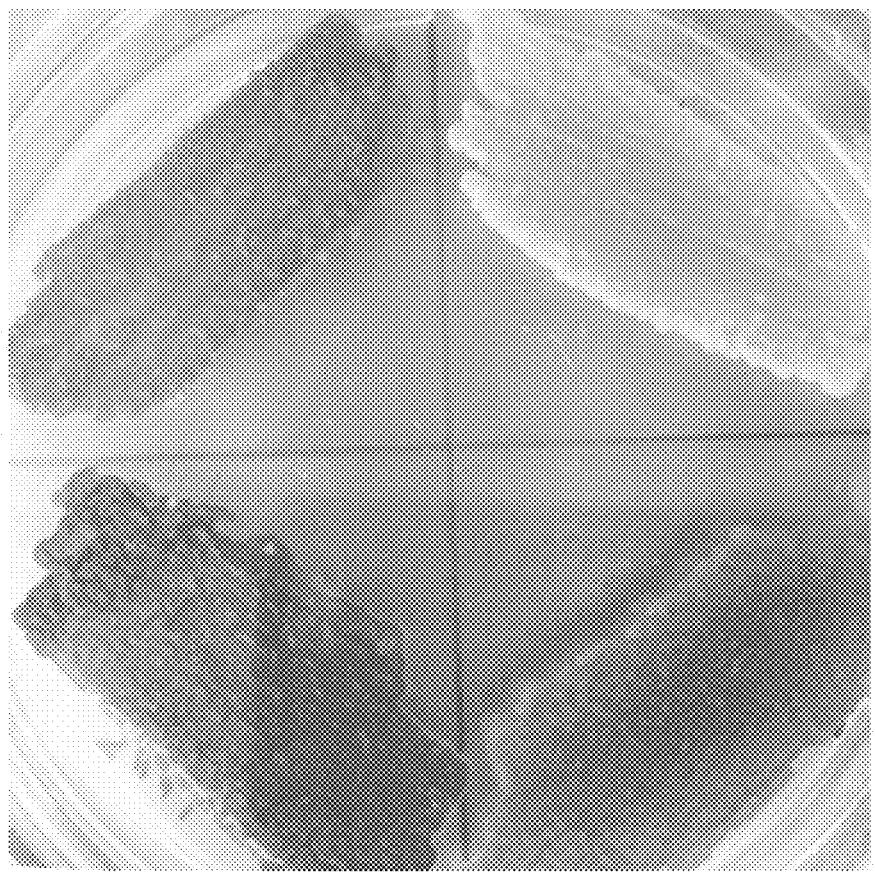
Figure 15:
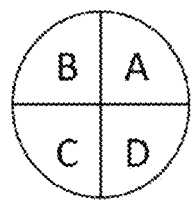
FIG. 15. depicts a photographic image of an agar plate showing that intron-containing promoter and FPPS::GGPPS fusion protein increases β-carotene production in *Y. lipolytica*. Strains in the image were grown on the YPD plate for two days. (A) *Y. lipolytica* containing YAL-rDNA-URA3-TEF-OptcarB-TEF-OptcarRP-TEF-YLGGPPS vector (AI-010); (B) *Y. lipolytica* containing YAL-rDNA-URA3-TEFIN-OptcarB-TEFIN-OptcarRP-TEFIN-YLGGPPS (AI-008); (C) Strain (AI-008) containing FPPS::GGPPS fusion gene; and (D) Strain (AI-010) containing FPPS::GGPPS fusion gene.
Figure 15:

As shown in FIG. 14 and FIG. 15, intron-containing TEFIN promoter increased the accumulation of lycopene and β-carotene in *Y. lipolytica*. Spectrometric analysis indicated that the production was increased by 3-fold for lycopene (UV-Vis absorbance value of 0.153±0.024 vs 0.472±0.032) and 1.6-fold (0.358±0.051 vs 0.583±0.061) for β-carotene.

Example 6: Expression of FPPS::GGPPS Fusion Protein Increases α-Carotene and Lycopene Production in *Y. lipolytica*

It has been reported that fusing FPPS to GGPPS increases geranyl geraniol and bisabolene production in *Saccharomyces cerevisiae*. However, *Y. lipolytica* is a dimorphic yeast, phylogenetically very distant from the model yeast *S. cerevisiae*. Additionally, *Y. lipolytica* possesses a larger genome (20 Mbp vs. 10 Mbp) with a lower overall gene density than *S. cerevisiae*. In order to determine if fused FPPS to GGPPS of *Y. lipolytica* also increases the production of carotenoid, precursors of ionones, FPPS to GGPPS of *Y. lipolytica* were fused, separated by a four amino acid linker.

Reconstruction of β-Carotene Biosynthetic Pathway in *Y. lipolytica*

The β-carotene biosynthetic pathway was reconstructed using the same strategy described above, wherein the wild-type bifunctional lycopene cyclase/phytoene synthase (carRP; SEQ ID NO: 63) replaces the modified carRP* (SEQ ID NO: 66). The resulting plasmid YAL-rDNA-URA3-TEF-OptcarB-TEF-OptcarRP-TEF-YLGGPPS was transformed into *Y. lipolytica*, to generate the β-carotene-producing strain designated AI-009. The strain with the URA3 marker gene removed was designated AI-010. Extraction of β-carotene was as described above for ε-carotene.

Fusion of FPPS and GGPPS with PCR

To construct the FPPS::GGPPS fusion gene, the stop codon of FPPS (SEQ ID NO: 72) was removed and a nine amino acid linker (Gly-Gly-Gly-Ser) was introduced between the open reading frame of FPPS and GGPPS via two-rounds PCR strategy yielding the fusion gene of FPPS::GGPPS (SEQ ID NO: 73). One PCR was carried out with forward primer of YlFPPS-BamHIF (SEQ ID NO: 31) and reverse primer of YlFPPS-GGPPS-R (SEQ ID NO: 33), and another PCR was performed with primers YlFPPS-GGPPS-F (SEQ ID NO: 34) and YlGGPPS-AvrIIR (SEQ ID NO: 23). The genomic DNA of *Y. lipolytica* was used as a template. Each PCR product was purified and used as a template for stitching the amplification fragments in a second round of PCR amplification, using primers YlFPPS-BamHIF (SEQ ID NO: 31)/YlGGPPS-AvrIIR (SEQ ID NO: 23) and YlFPPS-SnaBIF (SEQ ID NO: 32)/YlGGPPS-AvrIIR (SEQ ID NO: 23). This resulting 2.04 kb fusion product was inserted into the expression vector YAL-rDNA-URA3-TEF-XPR2 at the BamHI and AvrII sites and YAL-rDNA-URA3-TEFIN-XPR2, yielding YAL-rDNA-URA3-TEF-FPPS::GGPPS and YAL-rDNA-URA3-TEFIN-FPPS::GGPPS. The resultant plasmid was confirmed using restriction enzyme digestion and sequencing. The YAL-rDNA-URA3-TEF-FPPS::GGPPS vector was transformed into lycopene and β-carotene-producing strains AI-002 and AI-010, and the YAL-rDNA-URA3-TEFIN-FPPS::GGPPS vector was introduced into lycopene and β-carotene-producing strains AI-007 and AI-008.

As shown in FIG. 14 and FIG. 15, the expression of the FPPS::GGPPS fusion protein (SEQ ID NO: 74) increased the accumulation of lycopene and β-carotene in *Y. lipolytica*. Spectrometric analysis indicated that expression of FPPS::GGPPS fusion gene increased lycopene and β-carotene production in *Y. lipolytica* by up to 4-fold (UV-Vis absorbance value of 0.153±0.024 vs 0.608±0.046) for lycopene, and 2-fold (0.358±0.051 vs 0.721±0.082) for β-carotene.

Example 7: Reconstruction of β-Ionone Biosynthetic Pathway in *Y. lipolytica*

Figure 16:
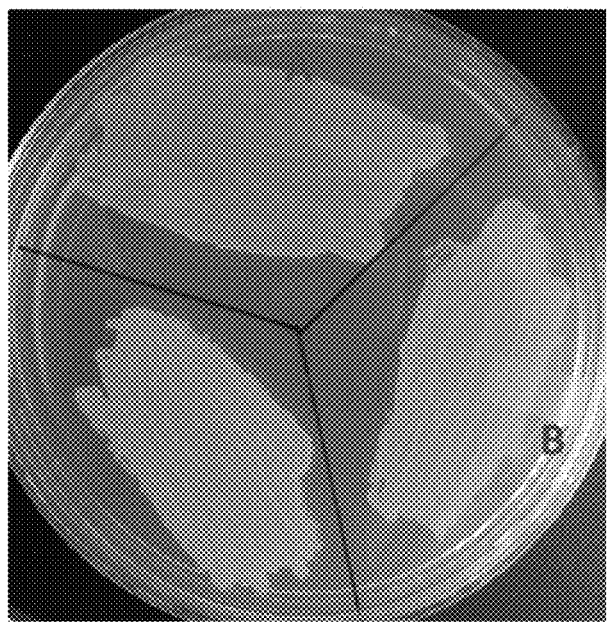
FIG. 16 depicts a photographic image of an agar plate showing the expression of DcCCD1 in β-carotene-producing *Y. lipolytica* strain (AI-010). (A) AI-010 strain transformed with empty vector, and AI-010 strain transformed with vector expressing DcCCD1 (B) and (C).

As described above, the cleavage reactions of carotenoids are generally catalyzed by a class of non-heme iron enzymes known as carotenoid cleavage dioxygenases (CCDs). In plants, CCDs are generically grouped into five subfamilies according to cleavage position and substrate preference. The carotenoid cleavage dioxygenase family 1 (CCD1) cleaves β-carotene at 9, 10 and 9'10' double bonds, generating β-ionone. Many CCD1 genes have been cloned and characterized from different plants, such as *Arabidopsis*, tomato, *crocus, petunia*, and carrot. As mentioned above, a nucleic acid sequence (SEQ ID NO: 88) encoding a protein with carotenoid cleavage dioxygenase activity, DcCCD1 (SEQ ID NO: 92), was identified in carrot. DcCCD1 cleaves cyclic carotenes to generate α-ionone and β-ionone. In order to demonstrate if the enzyme can cleave β-carotene, the DcCCD1 expression vector (YAL-rDNA-URA3-TEF-DcCCD1) was constructed and introduced into the *Y. lipolytica* strain engineered to accumulate β-carotene (AI-010). As shown in FIG. 16, the expression of DcCCD1 led to the expected decoloration of the accumulated orange β-carotene *Y. lipolytica* strain (AI-010), which was absent in control expressing the empty vector.

Example 8: Production of Lycopene in *Saccharomyces cerevisiae*

The *S. cerevisiae* strain WAT11 (MATa; ade2-1; his3-11, -15; leu2-3, -112; ura3-1; canR; cyr+) was grown at 28° C. with shaking at 250 rpm in YPD medium (10 g/L yeast extract, 20 g/L peptone and 20 g/L glucose) or in SD-dropout medium containing 1.7 g/L yeast nitrogen base without amino acids and ammonium sulfate, 20 g/L D-glucose, 5 g/L ammonium sulfate, 2 g/L yeast synthetic drop-out medium supplements (US biological, Swampscott, Mass.). Depending on the nutrient requirement of strains, 20 mg/L histidine, 100 mg/L leucine, 50 mg/L tryptophan or 40 mg/L uracil may be added to the medium. 20 g/L agar may be used for plates.

Construction of Lycopene Biosynthetic Pathway Plasmids

The pathway of lycopene biosynthesis in *S. cerevisiae* was reconstituted by over-expressing three enzymes: phytoene dehydrogenase (SEQ ID NO: 61) from *Mucor circinelloides* (carB; SEQ ID NO: 60) and modified bi-functional lycopene cyclase/phytoene synthase (SEQ ID NO: 69) from *Mucor circinelloides* (carRP*; SEQ ID NO: 68), the genes of both of which were codon-optimized for expression in *S. cerevisiae*, truncated 3-hydroxy-3-methyl-glutaryl-CoA reductase (tHMG1; SEQ ID NO: 82) encoded by SEQ ID NO: 81, and farnesyl pyrophosphate synthase (SeERG20; SEQ ID NO: 76 encoded by SEQ ID NO: 75)::geranylgeranyl diphosphate synthase (SeGGPPS; SEQ ID NO: 78 encoded by SEQ ID NO: 77) fusion gene (SeERG20::SeGGPPS SEQ ID NO: 80) from *S. cerevisiae* encoded by SEQ ID NO: 79. The carB and carRP* genes codon-optimized for expression in *S. cerevisiae* were cloned and expressed in *S. cerevisiae*. The four genes, carB, caRP*, SeERG20::SeGGPPS and tHMG1, were amplified by PCR using the primers, ScarB-EcoRIF (SEQ ID NO: 41)/SecarB-BglIIR (SEQ ID NO: 42), SecarRP*-BamHIF (SEQ ID NO: 43)/SecarRP*-XhoIR (SEQ ID NO: 44), SetHMG1-EcoRIF (SEQ ID NO: 45)/SetHMG1-SpeIR (SEQ ID NO: 46), and SeERG20::SeGGPPS-BamHIF (SEQ ID NO: 47), SeERG20::SeGGPPS-XhoIR (SEQ ID NO: 48), respectively. The carB and carRP* genes were placed under the control of the GAL10 and GAL1 promoters in the pESC-TRP yeast expression vector, respectively, to form the plasmid pESC-TRP-carB-carRP*. The tHMG1 gene was cloned into the EcoRI/SpeI sites of the pESC-HIS to yield pESC-HIS-tHMG1. Then the SeERG20::SeGGPPS was cloned into the BamHI/XhoI site of pESC-HIS-tHMG1 to yield pESC-tHMG1-SeERG20::SeGGPPS.

Expression of Lycopene Biosynthetic Pathway Genes in *S. cerevisiae*

*S. cerevisiae* Wat11 was transformed with pESC-TRP-carB-carRP* and pESC-HIS-tHMG1-SeERG20::SeGGPPS, and the transformants were screened on SD-Trp-His agar plate. Single colonies were cultured in SR medium (0.67% yeast nitrogen base, 2% raffinose, 0.2% complete supplement mixture) that lacked tryptophan and histidine. The medium further included 2% galactose for inducing expression of genes introduced downstream of GAL1 and GAL10 promoters. The cultured cells were collected by centrifugation, and the cell pellets were re-suspended in extraction solution (methyl-t-butyl ether:methanol:ethyl acetate (40:50:10)). The cell suspension was lysed using 300 µl of 425-600 µm diameter glass beads for 3 min with a vortex mixer. The extract was collected after centrifugation, and the supernatant was analyzed by HPLC.

Example 9: Reconstruction of ε-Carotene Biosynthetic Pathway in S. cerevisiae The codon-optimized lycopene ε-cyclase from *Lactuca sativa* (LsLCYE; SEQ ID NO: 85) was synthesized and amplified with primers, Se-LsLCYe-BamHIF (SEQ ID NO: 49)/Se-LsLCYE-XhoIR (SEQ ID NO: 50) and cut by BamHI and XhoI. Then, the digested fragment was cloned into BamHI/XhoI-digested vector pESC-LEU, to form pESC-LEU-LsLCYE. Strain carrying plasmid pESC-TRP-carB-carRP* and pESC-HIS-tHMG1-SeERG20::SeGGPPS were transformed with pESC-LEU-LsLCYE plasmid, and Trp+ His+ Leu+ colonies were selected on SD-Trp-His-Leu plate. After incubation in liquid SD medium, the pellets were suspended in extraction solution (dichloromethane/methanol, 25:75, v/v) and analyzed by HPLC.

Example 10. Reconstruction of α-Ionone Biosynthetic Pathway in S. cerevisiae Plasmids Construction DcCCD1, carotenoid cleavage dioxygenase of carrot was codon-optimized (SEQ ID NO: 90) for expression in *S. cerevisiae*, and amplified with primers SeDcCCD1-EcoRIF (SEQ ID NO: 53) and SeDcCCD1-BglIIR (SEQ ID NO: 54). The amplification product was then cloned into the EcoRI/BglII restriction sites of the pESC-URA vector, to form pESC-URA-DcCCD1. The *S. cerevisiae* strain harboring pESC-TRP-carB-carRP*, pESC-HIS-tHMG1-SeERG20:: SeGGPPS and pESC-LEU-LsLCYE was transformed with pESC-URA-DcCCD1, and Trp+, His+, Leu+ and Ura+ colonies selected on SD minus four amino acids plate.

Solid Phase Microextraction (SPME), HPLC and GC-MS Analysis

The same procedures was applied to grow and induce gene expression as described above. The headspace was sampled with a Carboxen/Polydimethylsiloxane (CAR/PDMS) fiber for one hour at room temperature. The volatile compounds collected from the headspace were analyzed using gas chromatography-mass spectrometry. Identification of α-ionone was performed by comparison of mass spectra and retention time data to authentic standard and was supplemented with GC-MS library.

Example 11. Production of α-Ionone and β-Ionone in E. coli

Bacterial Strains and Plasmids

*E. coli* C2984 and BL21 (DE3) (New England Biolabs, Ipswich, Mass.) were used for cloning and recombinant protein expression. Plasmid pETDuet-1, and pCOLADuet-1 were used for recombinant protein expression purposes.

Construction of Plasmid for β-Carotene and ε-Carotene Synthesis

The pAC-BETA and pAC-LYC plasmids was used to produce β-carotene and lycopene, respectively. The pAC-BETA plasmid contains all of the genes required for the synthesis of β-carotene, including crtE [GGPP (geranylgeranyl pyrophosphate) synthase], crtB (phytoene synthase), crtI (phytoene desaturase) and crtY (lycopene cyclase) from *Erwinia herbicola*], and retains a chloramphenicol resistance gene (Cunningham et al., Plant Cell, 8: 1613-1626, 1996). Plasmid pAC-LYC is a pACYC184 derived vector containing functional carotenoid biosynthesis genes for geranylgeranyl pyrophosphate synthase (crtE), phytoene synthase (crtB), and phytoene desaturase (crtI) from *Erwinia herbicola*, and also contains a chloramphenicol resistance gene (Cunningham et al., Plant Cell, 6: 1107-1121, 1994). *E. coli* colonies containing pAC-LYC accumulate lycopene.

The LsLCYE gene fragment was synthesized and amplified by PCR using the primers EcLsLCYE-BamHIF (SEQ ID NO: 51) and EcLsLCYE-PstIR (SEQ ID NO: 52). The purified LsLCYE gene fragment was excised using BamHI and PstI, followed by insertion into the corresponding sites of the vector pETDuet-1 to create pETDuet-LsLCYE. The plasmid pETDuet-LsLCYE, extracted from the colony with the positive insert and confirmed by sequencing, was transformed into *E. coli* BL21 (DE3) containing the plasmid pAC-LYC for protein expression and production of ε-carotene.

Construction of plasmid for α-ionone and β-ionone synthesis

The DcCCD1 gene fragment was synthesized and obtained by PCR using the primers EcDcCCD1-EcoRIF (SEQ ID NO: 55) and EcDcCCD1-PstIR (SEQ ID NO: 56). The purified DcCCD1 gene fragment was digested by EcoRI and PstI, followed by insertion into the corresponding sites of the vector pCOLADuet-1 to create pCOLADuet-DcCCD1. Subsequently, the plasmid pCOLADuet-DcCCD1 was transformed into BL21 (DE3) containing pAC-BETA for production of β-ionone and transformed into BL21 (DE3) harboring pAC-LYC and pETDuet-LsLCYE for production of α-ionone.

Shake Flask Cultures and Growth Conditions

*E. coli* BL21 (DE3) containing pAC-BETA and pCOLADuet-DcCCD1 was grown in the LB medium with 34 mg/L chloramphenicol and 50 mg/L kanamycin to OD600=0.6 in a shaker at 37° C., and then changed to 30° C. with addition of lactose to a final concentration of 1.5% (w/v) to induce the expression of DcCCD1 and further incubated at 30° C. *E. coli* BL21 (DE3) containing pAC-LYC, pETDuet-LsLCYE and pCOLADuet-DcCCD1 was grown in the LB medium with 34 mg/L chloramphenicol, 100 mg/L ampicillin, and 50 mg/L kanamycin to OD600=0.6 in a shaker at 37° C., and then changed to 30° C. with the addition of lactose to final concentration of 1.5% (w/v) to induce the expression of LsCYE and DcCCD1. The culture was kept shaking under the same culture condition, and samples were taken at intervals for GC-MS analysis as mentioned above.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Although the disclosure described herein is susceptible to various modifications and alternative iterations, specific embodiments thereof have been described in greater detail above. It should be understood, however, that the detailed description is not intended to limit the disclosure to the specific embodiments disclosed. Rather, it should be understood that the disclosure is intended to cover all modifications, equivalents, and alternatives falling within the spirit and scope of the disclosure as defined by the claim language.

What is claimed:

1. A recombinant microorganism comprising a nucleic acid construct comprising:
   a) a nucleic acid sequence encoding a lycopene s-cyclase enzyme encoded by LCYe from *Lactuca sativa*; and
   b) a nucleic acid sequence encoding a carotenoid cleavage dioxygenase enzyme encoded by CCD1 from *Daucus carota*:
   wherein the nucleic add sequences are operably linked to one or more expression control sequences, and wherein the microorganism further comprises lycopene.

2. The microorganism of claim 1, wherein the microorganism is selected from a microorganism genetically engineered to inhibit the expression of lycopene β-cyclase and a microorganism naturally not capable of expressing lycopene β-cyclase.

3. The microorganism of claim 1, wherein the microorganism is selected from *Yarrowia lipolytica, Saccharomyces cerevisiae*, and *E. coli*.

4. The microorganism of claim 1, wherein the nucleic acid construct is codon optimized for expression in the microorganism.

5. The microorganism of claim 1 where said microorganism produces pure R(+)-α-ionone.

6. The recombinant microorganism of claim 1, wherein the nucleic acid expression construct comprises a nucleic acid sequence encoding a lycopene ε-cyclase enzyme with at least 80% sequence identity to the amino acid sequence of SEQ ID NO: 87.

7. The recombinant microorganism of claim 1, wherein the nucleic acid expression construct comprises a nucleic acid sequence encoding a carotenoid cleavage dioxygenase enzyme with at least 80% sequence identity to the amino acid sequence of SEQ ID NO: 92.

* * * * *

UNITED STATES PATENT AND TRADEMARK OFFICE
CERTIFICATE OF CORRECTION

Page 1 of 1

PATENT NO. : 10,364,434 B2
APPLICATION NO. : 15/560951
DATED : July 30, 2019
INVENTOR(S) : Yechun Wang It is certified that error appears in the above-identified patent and that said Letters Patent is hereby corrected as shown below:

On the Title Page

Items (71), (72), and (73) should read:

(71) Applicant: Arch Innotek, LLC, St. Louis, MO (US)
Conagen, Inc., Bedford, MA (US)

(72) Inventor: Yechun Wang, St. Louis, MO (US)
Oliver Yu, Lexington, MA (US)

(73) Assignee: Arch Innotek, LLC, St. Louis, MO (US)
Conagen, Inc., Bedford, MA (US)

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*